US007186825B2

(12) United States Patent
Frydman et al.

(10) Patent No.: US 7,186,825 B2
(45) Date of Patent: Mar. 6, 2007

(54) CONFORMATIONALLY RESTRICTED POLYAMINE ANALOGS AS DISEASE THERAPIES

(75) Inventors: Benjamin Frydman, Madison, WI (US); Laurence J. Marton, Fitchburg, WI (US); Venodhar K. Reddy, Madison, WI (US); Aldonia L. Valasinas, Madison, WI (US); Andrei V. Blokhin, Madison, WI (US); Hirak S. Basu, Madison, WI (US)

(73) Assignee: Cellgate, Inc., Redwood City, CA (US)

( * ) Notice: Subject to any disclaimer, the term of this patent is extended or adjusted under 35 U.S.C. 154(b) by 0 days.

(21) Appl. No.: 10/873,100

(22) Filed: Jun. 21, 2004

(65) Prior Publication Data
US 2004/0235962 A1 Nov. 25, 2004

Related U.S. Application Data

(62) Division of application No. 09/560,711, filed on Apr. 27, 2000, now Pat. No. 6,794,545.

(60) Provisional application No. 60/131,779, filed on Apr. 30, 1999.

(51) Int. Cl.
C07C 47/00 (2006.01)
(52) U.S. Cl. ................... 540/145; 548/518; 514/427
(58) Field of Classification Search ............... 540/145
See application file for complete search history.

(56) References Cited

U.S. PATENT DOCUMENTS

| 2,440,724 A | 5/1948 | Morey |
| 3,008,993 A | 11/1961 | Lesslie et al. |
| 3,397,223 A | 8/1968 | Payne |
| 3,773,833 A | 11/1973 | Henrici et al. |
| 4,035,174 A | 7/1977 | Grier et al. |
| 4,092,432 A | 5/1978 | Björklund et al. |
| 4,153,567 A | 5/1979 | Kluger et al. |
| 4,443,604 A | 4/1984 | Lee |
| 4,491,651 A | 1/1985 | Naiman |
| 4,537,601 A | 8/1985 | Naiman |
| 4,551,550 A | 11/1985 | Bey |
| 4,590,288 A | 5/1986 | Klemann |
| 4,642,344 A | 2/1987 | Hajek et al. |
| 4,658,023 A * | 4/1987 | Shudo ............. 540/145 |
| 4,661,509 A | 4/1987 | Gordon et al. |
| 4,698,446 A | 10/1987 | Lai et al. |
| 4,784,736 A | 11/1988 | Lonsdale et al. |
| 4,868,219 A | 9/1989 | Thornfeldt |
| 4,935,449 A | 6/1990 | Bey et al. |
| 5,021,409 A | 6/1991 | Murrer et al. |
| 5,021,571 A | 6/1991 | Mease et al. |
| 5,132,425 A | 7/1992 | Sotoya et al. |
| 5,217,964 A | 6/1993 | Edwards et al. |
| 5,242,684 A | 9/1993 | Merianos |
| 5,274,090 A * | 12/1993 | Zhang et al. ......... 540/145 |
| 5,275,801 A | 1/1994 | Niedballa et al. |
| 5,283,367 A | 2/1994 | Babiarz et al. |
| 5,354,782 A | 10/1994 | Edwards et al. |
| 5,374,658 A | 12/1994 | Lau |
| 5,401,443 A | 3/1995 | Nagano et al. |
| 5,413,719 A | 5/1995 | Sivakumar et al. |
| 5,434,145 A | 7/1995 | Edwards et al. |
| 5,498,522 A | 3/1996 | Porter |
| 5,512,597 A | 4/1996 | Kyba et al. |
| 5,516,807 A | 5/1996 | Hupe et al. |
| 5,541,230 A | 7/1996 | Basu et al. |
| H1633 H | 2/1997 | Hiebert et al. |
| 5,599,847 A | 2/1997 | Robins et al. |
| 5,606,053 A | 2/1997 | Prashad et al. |
| 5,607,574 A | 3/1997 | Hart |
| 5,608,061 A | 3/1997 | Ciszewski et al. |
| 5,608,086 A | 3/1997 | Hemmerle |
| 5,612,478 A | 3/1997 | Xu et al. |
| 5,627,215 A | 5/1997 | Frei et al. |
| 5,646,188 A | 7/1997 | Gilad et al. |
| 5,650,099 A | 7/1997 | Akhavan-Tafti et al. |
| 5,654,287 A | 8/1997 | Prakash et al. |
| 5,654,484 A | 8/1997 | Prakash et al. |
| 5,672,202 A | 9/1997 | Stirling et al. |
| 5,677,349 A | 10/1997 | Gilad et al. |

(Continued)

FOREIGN PATENT DOCUMENTS

| DE | 1295826 | 5/1969 |
| EP | 0 335 539 A2 | 10/1989 |
| EP | 0723772 A1 | 7/1996 |
| JP | 62-167783 A | 7/1987 |
| JP | 05-032902 A2 | 2/1993 |
| JP | 07-277964 A2 | 10/1995 |

(Continued)

OTHER PUBLICATIONS

Database CAPLUS on STN, Acc. No. 1991:665287, Wamser et al., Report (1989), DOE/ER/13389-3 from Energy Res. Abstr. 1991, 16(5), Abstr. No. 13112.*
Alfonso, I. et al., (1996) "Sequential Biocatalytic Resolution of (+)-trans-cyclohexane-1,2-diamine. Chemoenzymic Synthesis of an Optically Active Polyamine," *Chem. Commun.* 21:2471-2472.
Ando, A. et al. (Aug. 1990). "Synthesis of Fluorine Analogues of Protoporphyrin Potentially Useful for Diagnosis and Therapy of Tumors," *Chemical and Pharmaceutical Bulletin* 38(8):2175-2178.
Ashton, W.T. et al. (1988). "Synthesis and Antiherpetic Activity of (±)-9-[[(Z)-2-(Hydroxymethyl)cyclopropyl]methyl]guanine and Related Compounds," *J. Med. Chem.* 31(12):2304-2315.

(Continued)

*Primary Examiner*—Brian Davis
(74) *Attorney, Agent, or Firm*—Morrison & Foerster, LLP

(57) ABSTRACT

Novel conformationally restricted polyamine analogs are provided, as well as compositions comprising these novel polyamine analogs. Methods of using the novel polyamine analogs in treatment of diseases such as cancer are also provided. Also provided is a method of delivering these analogs specifically to tumor cells by covalently attaching polyamine analogs to porphyrin compounds, along with novel polyamine-porphyrin covalent conjugates.

20 Claims, 56 Drawing Sheets

U.S. PATENT DOCUMENTS

| | | |
|---|---|---|
| 5,677,350 A | 10/1997 | Frydman |
| 5,677,351 A | 10/1997 | Bergeron, Jr. |
| 5,681,837 A | 10/1997 | Bergeron |
| 5,707,532 A | 1/1998 | Guerro et al. |
| 5,719,193 A | 2/1998 | Bowlin et al. |
| 5,744,453 A | 4/1998 | Mintz et al. |
| 5,763,388 A | 6/1998 | Lightsey et al. |
| 5,824,812 A | 10/1998 | Nantz et al. |
| 5,843,865 A | 12/1998 | Del Corral et al. |
| 5,843,959 A | 12/1998 | Bergeron, Jr. |
| 5,849,259 A | 12/1998 | Hilger et al. |
| 5,880,161 A | 3/1999 | Basu et al. |
| 5,886,050 A | 3/1999 | Bergeron, Jr. |
| 5,886,051 A | 3/1999 | Bergeron, Jr. et al. |
| 5,889,061 A | 3/1999 | Frydman et al. |
| 5,906,996 A | 5/1999 | Murphy |
| 5,912,341 A | 6/1999 | Hoffman et al. |
| 5,958,397 A | 9/1999 | Smerbeck et al. |
| 5,962,533 A | 10/1999 | Bergeron, Jr. |
| 6,034,129 A | 3/2000 | Mandeville, III et al. |
| 6,051,611 A | 4/2000 | Kyba et al. |
| 6,100,430 A | 8/2000 | Yamamoto et al. |
| 6,103,666 A | 8/2000 | Del Corral et al. |
| 6,114,321 A | 9/2000 | Platzek et al. |
| 6,184,232 B1 | 2/2001 | Bergeron, Jr. |
| 6,207,660 B1 | 3/2001 | Sessler et al. |
| 6,235,794 B1 | 5/2001 | Bergeron, Jr. |
| 6,274,630 B1 | 8/2001 | Bergeron, Jr. |
| 6,307,102 B1 | 10/2001 | Tokumoto et al. |
| 6,319,956 B1 | 11/2001 | Iwata |
| 6,342,534 B1 | 1/2002 | Bergeron, Jr. |
| 6,384,097 B1 | 5/2002 | Tokumoto et al. |
| 6,384,177 B1 | 5/2002 | Tokumoto et al. |
| 6,392,098 B1 | 5/2002 | Frydman et al. |
| 6,395,257 B1 | 5/2002 | Achilefu et al. |
| 6,399,662 B1 | 6/2002 | Bergeron |
| 6,444,707 B1 | 9/2002 | Lampe et al. |
| 6,528,048 B1 | 3/2003 | Koike et al. |
| 6,531,512 B1 | 3/2003 | Kramer et al. |
| 6,605,645 B2 | 8/2003 | Iwata |
| 6,641,655 B1 | 11/2003 | McElhinney et al. |
| 6,649,587 B1 | 11/2003 | Frydman et al. |
| 6,664,270 B2 | 12/2003 | Bergeron, Jr. |
| 6,673,890 B1 | 1/2004 | Boeckh et al. |
| 6,706,922 B2 | 3/2004 | Wolff et al. |
| 6,794,545 B1 | 9/2004 | Frydman et al. |
| 6,906,050 B2 | 6/2005 | Robinson |
| 2002/0045780 A1 | 4/2002 | Bergeron, Jr. |
| 2002/0061287 A1 | 5/2002 | Wolff et al. |
| 2002/0061926 A1 | 5/2002 | Phillips |
| 2002/0094990 A1 | 7/2002 | Bergeron |
| 2002/0143068 A1 | 10/2002 | Bergeron, Jr. |
| 2002/0155999 A1 | 10/2002 | Han |
| 2003/0036576 A1 | 2/2003 | Rajagopalan et al. |
| 2003/0045674 A1 | 3/2003 | Higley |
| 2003/0055113 A1 | 3/2003 | Wang et al. |
| 2003/0100615 A1 | 5/2003 | Bergeron, Jr. |
| 2003/0100752 A1 | 5/2003 | Robinson |
| 2003/0130356 A1 | 7/2003 | Frydman et al. |
| 2003/0130534 A1 | 7/2003 | Golden |
| 2003/0143713 A1 | 7/2003 | Aghajari et al. |
| 2003/0158262 A1 | 8/2003 | Ramesh et al. |
| 2003/0185778 A1 | 10/2003 | Fahl et al. |
| 2003/0195377 A1 | 10/2003 | Frydman et al. |
| 2003/0232799 A1 | 12/2003 | Wang et al. |
| 2004/0006055 A1 | 1/2004 | Winchell |
| 2004/0019043 A1 | 1/2004 | Coucouvanis et al. |
| 2004/0019087 A1 | 1/2004 | Temansky et al. |
| 2004/0039057 A1 | 2/2004 | Perlmutter et al. |
| 2004/0047844 A1 | 3/2004 | Shepard |
| 2004/0152687 A1 | 8/2004 | Frydman et al. |
| 2004/0192665 A1 | 9/2004 | Frydman et al. |

FOREIGN PATENT DOCUMENTS

| | | |
|---|---|---|
| WO | WO-89/02269 A1 | 3/1989 |
| WO | WO-94/07480 A1 | 4/1994 |
| WO | WO-94/07894 A1 | 4/1994 |
| WO | WO-95-18091 A1 | 7/1995 |
| WO | WO-96/22962 A1 | 8/1996 |
| WO | WO-96/40096 A1 | 12/1996 |
| WO | WO-97/02027 A1 | 1/1997 |
| WO | WO-97/31611 A1 | 9/1997 |
| WO | WO-98/14190 A1 | 4/1998 |
| WO | WO-98/17624 A1 | 4/1998 |
| WO | WO-98/32729 A1 | 7/1998 |
| WO | WO-99/21542 A2 | 5/1999 |
| WO | WO-99/21542 A3 | 5/1999 |
| WO | WO-99/54283 A1 | 10/1999 |
| WO | WO-00/66175 A2 | 11/2000 |
| WO | WO-00/66528 A2 | 11/2000 |
| WO | WO-00/66528 A3 | 11/2000 |
| WO | WO-02/10142 A1 | 2/2002 |
| WO | WO-02/062341 A1 | 8/2002 |
| WO | WO-03/004091 A2 | 1/2003 |
| WO | WO-03/004091 A3 | 1/2003 |
| WO | WO-03/004466 A2 | 1/2003 |
| WO | WO-03/004466 A3 | 1/2003 |
| WO | WO-03/033455 A1 | 4/2003 |
| WO | WO-03/050072 A1 | 6/2003 |
| WO | WO-03/051348 A2 | 6/2003 |
| WO | WO-2004/002991 A1 | 1/2004 |
| WO | WO-2004/012774 A1 | 2/2004 |
| WO | WO-2004/041828 A1 | 5/2004 |

OTHER PUBLICATIONS

Bachmann, S. et al. (2001). "Cis-Selective Asymmetric Cyclopropanation of Olefins Catalyzed by Five-Coordinate [RuCl(PNNP)]+ Complexes," *Organometallics* 20(10):2102-2108.

Bachrach, U. et al. (1971) "Antivirus Action of Acrolein, Glutaraldehyde and Oxidized Spermine," *J. Gen. Virol.* 13(3):415-422.

Bachrach, U. et al. (1971). "Inactivation of Myxoviruses by Oxidized Polyamines," *J. Gen. Virol.* 11(1):1-9.

Bachrach, U. et al. (1972). "Effect of Oxidized Spermine and Other Aldehydes on the Infectivity of Vaccinia Virus," *Appl. Microbiol.* 23(2):232-235.

Barluenga, J. et al. (2000). "Diastereoselective Intermolecular Cyclopropanation of Simple Alkenes by Fischer Alkenyl and Heteroaryl Carbene Complexes of Chromium: Scope and Limitations," *J. Am. Chem. Soc.* 122(34):8145-8154.

Basu, H.S. et al. (1990). "Effects of Variation in the Structure of Spermine on the Association with DNA and the Induction of DNA Conformational Changes," *Biochem. J.* 269(2):329-334.

Behe, M. et al. (1981). "Effects of Methylation on a Synthetic Polynucleotide: the B-Z Transition in Poly(dG-m5dC).Poly(dG-m5dC)." *Proc. Natl. Acad. Sci. USA* 78(3):1619-1623.

Berchtold, C.M. et al. (1998). "Inhibition of Cell Growth in CaCO2 Cells by the Polyamine Analogue N1,N12-Bis(Ethyl)Spermine is Preceded by a Reduction in MYC Oncoprotein Levels," *Journal of Cellular Physiology* 174(3):380-386.

Bergeron, R.J. et al. (1994). "Antiproliferative Properties of Polyamine Analogues: A Structure-Activity Study," *J. Med. Chem.* 37(21):3464-3476.

Bernacki, R.J. et al. (1992). "Antitumor Activity of N,N'-Bis(Ethyl)Spermine Homologues Against Human MALME-3 Melanoma Xenografts," *Cancer Research* 52(9):2424-2430.

Bloomfield, V.A. et al. (1981). "Chapter 10: Interactions of Polyamine with Polynucleotide" in vol 8: *Polyamines in Biology and Medicine*. Morris et al., eds., Dekker, New York, pp. 184-206.

Brunner, H. et al. (1994). "Platinum(II) Complexes With Porphyrin Ligands—Additive Cytotoxic and Photodynamic Effect," *Angewandte Chemie* 33(21):2214-2215.

Byers, T.L. et al. (1990). "Regulation of Polyamine Transport in Chinese Hamster Ovary Cells," *Journal of Cellular Physiology* 143(3):460-467.

Casero, R.A. Jr. et al. (1995). "Growth and Biochemical Effects of Unsymmetrically Substituted Polyamine Analogues in Human Lung Tumor Cells," *Cancer Chemother. Pharmacol.* 36:69-74.

Casero, R.A. Jr. et al. (Jan. 4, 2001). "Terminally Alkylated Polyamine Analogues as Chemotherapeutic Agents," *Journal of Medicinal Chemistry* 44(1):1-26.

Chang, B.K. et al. (1992). "Antitumor Effects of N-Alkylated Polyamine Analogues in Human Pancreatic Adenocarcinoma Models," *Cancer Chemother. Pharmacol.* 30(3):179-182.

Chang, B.K. et al. (1992). "Regulatory and Antiproliferative Effects of N-Alkylated Polyamine Analogues in Human and Hamster Pancreatic Adenocarcinoma Cell Lines," *Cancer Chemother. Pharmacol.* 30(3):183-188.

Chang, B.K. et al., (1993). "Effects of Diethyl Spermine Analogues in Human Bladder Cancer Cell Lines in Culture," *Journal of Urology* 150(4):1293-1297.

Davidson, N.E. et al. (1993). "Growth Inhibition of Hormone-Responsive and -Resistant Human Breast Cnacer Cells in Culture by $N^1$, $N^{12}$-Bis(Ethyl)Spermine[1]," *Cancer Research* 53(9):2071-2075.

Doyle, M.P. et al. (1993). "Tetrakis[(4S)-4-phenyloxazolidin-2-one]dirhodium(II) and Its Catalytic Applications for Metal Carbene Transformations," *Helv. Chim. Acta.* 76:2227-2235.

Fernandez, C.O. et al. (1994). "Interactions Between Polyamine Analogs with Antiproliferative Effects and tRNA: a $^{15}$N NMR Analysis," *Cell Mol. Biol.* 40(7): 933-944.

Feuerstein, B.G. et al. (1991). "Implications and Concepts of Polyamine-Nucleic Acid Interactions," *Journal of Cellular Biochemistry* 46(1):37-47.

Fischer, H.A., (1975) "Synthesis of $^3$H-spermine," *J. Labelled Compd.* 11(1):141-143.

Frydman, B. et al. (1999). "Polyamine-based chemotherapy of cancer," *Opin. Ther. Patents.* 9(8):1055-1068.

Frydman, L. et al. (1992). "Interactions Between Natural Polyamines and tRNA: an $^{15}$N NMR Analysis," *Proc. Natl. Acad. Sci. USA* 89(19):9186-9190.

Gosule, L.C. et al. (1978). "DNA Condensation with Polyamines I. Spectroscopic Studies," *J. Mol. Biol.* 121(3):311-326.

Goto, M. et al., (1969) "Stereochemical Studies Of Metal Chelates. III. Preparation And Stereochemistry Of Cobalt (III) Complexes With C-Substituted Triethylenetetramines At The Central Ethylenediamine Bridge," *Inorg. Chem.* 8(2):358-366.

Ha, H.C. et al. (Jul. 1, 1998). "Unsymmetrically Substituted Polyamine Analogue Induces Caspase-Independent Programmed Cell Death in Bcl-2-Overexpressing Cells," *Cancer Research* 58:2711-2714.

Hafner, E.W. et al. (1979). "Mutants of *Escherichia coli* that do not Contain 1,4-Diaminobutane (Putrescine) or Spermidine," *J. Biol. Chem.* 254(24):12419-12426.

Herr, H.W. et al. (1984). "Potentiation of Methylglyoxal-Bis-Guanylhydrazone by Alpha-Difluoromethylornithine in Rat Prostate Cancer," *Cancer* 53(6):1294-1298.

Horoszewicz, J.S. et al. (1983). "LNCaP Model of Human Prostatic Carcinoma," *Cancer Res.* 43(4):1809-1818.

Igarashi, K. et al. (1990). "Spermine-Like Functions of $N^1$, $N^{12}$-Bis(Ethyl)Spermine: Stimulation of Protein Synthesis and Cell Growth and Inhibition of Gastric Ulceration," *Biochemical and Biophysical Research Communications* 172(2):715-720.

Jain, S. et al. (1989). "Base Only Binding of Spermine in the Deep Groove of the A-DNA Octamer d(GTGTACAC)," *Biochemistry* 28(6):2360-2364.

Jänne, J. et al. (1978). "Polyamines in Rapid Growth and Cancer," *Biochimica et Biophysica Acta.* 473(3-4):241-293.

Jeffers, L. et al. (1997). "Effects of the Polyamine Analogues BE-4-4-4-4, BE-3-7-3, and BE-3-3-3 on the Proliferation of Three Prostate Cancer Cell Lines," *Cancer Chemother Pharmacol* 40(2):172-179.

Kobiro, K. et al., (1992) "Synthesis And Molecular Structures Of Nickel (II) Alkyl-Substituted Cyclam Complexes," *Inorg. Chem.* 31(4):676-685.

Kramer, D. et al. (1995). "Stable Amplification of the S-Adenosylmethionine Decarboxylase Gene in Chinese Hamster Ovary Cells," *Journal of Biological Chemistry* 270(5):2124-2132.

Kramer, D.L. et al. (1993). "Regulation of Polyamine Transport by Polyamines and Polyamine Analogs," *Journal of Cellular Physiology* 155(2):399-407.

Kramer, D.L. et al. (1997). "Effects of Novel Spermine Analogues on Cell Cycle Progression and Apoptosis in MALME-3M Human Melanoma Cells," *Cancer Research* 57:5521-5527.

Lovaas, E. (1997). "Antioxidative and Metal-Chelating Effects of Polyamines," *Advances in Pharmacology* 38:119-149.

Mamont, P.S. et al. (1978). "Anti-Proliferative Properties of DL-Alpha-Difluoromethyl Ornithine in Cultured Cells. A Consequence of the Irreversible Inhibition of Ornithine Decarboxylase," *Biochem. Biophys. Res. Commun.* 81(1):58-66.

Marton, L.J. and Pegg A. E. (1995). "Polyamines as Targets for Therapeutic Intervention," *Annu. Rev. Pharm. Toxicol.* 35:55-91.

McCloskey, D.E. et al. (Jan. 2000). "Effects of the Polyamine Analogues $N^1$-Ethyl-$N^{11}$-((cyclopropyl)methyl-4,8-diazaundecane and $N^1$-Ethyl-$N^{11}$-((cycloheptyl)methyl)-4,8-diazaundecane in Human Prostate Cancer Cells," *Clinical Cancer Research* 6:17-23.

Mi et al. (1988) "Human Prostatic Carcinoma Cell Lines Display Altered Regulation Of Polyamine Transport In Response To Polyamine Analogs And Inhibitors," *The Prostate* 34:51-60.

Morgan, D.M. (1998). "Chapter 1: Polyamines. An Introduction" in *Methods. Mol. Biol.*, Morgan D., ed., Humana Press Inc., New Jersey, vol. 79, pp. 3-30.

Morgan, D.M. et al. (1986). "The Effect of Purified Aminoaldehydes Produced by Polyamine Oxidation on the Development in Vitro of Plasmodium Falciparum in Normal and Glucose-6-Phosphate-Dehydrogenase-Deficient Erythrocytes," *Biochem. J.* 236(1):97-101.

Morgan, D.M.L. et al. (1983) "Polyamine Oxidation and the Killing of Intracellular Parasites," *Adv. Polyamine Res.* 4: 169-174.

Nagarajan, S. et al., (1987) "Chemistry Of Naturally Occurring Polyamines. 11. Unsaturated Spermidine And Spermine Derivatives," *J. Org. Chem.* 52(22):5044-5046.

Nguyen, S.T. et al. (1999). "Diastereo—And Enantioselective Cyclopropanation of Alkenes Catalyzed by Ruthenium-Schiff-Base Complexes," *Abstracts of Papers, Part 1, 218th ACS National Meeting*, New Orleans, LA, Aug. 22-26, 1999, Abstract No. INOR-104, two pages.

Nishimura, K. et al. (1971). "Phagocidal Effects of Acrolein," *Biochim. Biophys. Acta* 247(1):153-156.

Payne, G.B. (Nov. 1967). "Cyclopropanes from Reactions of Ethyl(Dimethylsulfuranylidene)acetate with α,β—Unsaturated Compounds," *Journal of Organic Chemistry* 32(11):3351-3355.

Pegg, A.E. et al. (1982). "Polyamine Metabolism and Function," *Am. J. Cell. Physiol.* 243(5):C212-C221.

Pohjanpelto et al. (1981). "Polyamine Starvation Causes Disappearance Of Actin Filaments And Microtubules In Polyamine-Auxotrophic CHO Cells," *Nature* 293:475-477.

Porter, C.W. et al. (1988). "Regulation of Polyamine Biosynthetic Activity by Spermidine and Spermine Analogs—A Novel Antiproliferative Strategy," *Adv. Exp. Med. Biol.* 250:677-690.

Porter, C.W. et al. (1987). "Relative Abilities of Bis(ethyl) Derivatives of Putrescine, Spermidine, and Spermine to Regulate Polyamine Biosynthesis and Inhibit L1210 Leukemia Cell Growth," *Cancer Res.* 47(11):2821-2825.

Porter, C.W. et al. (1988). "Enzyme Regulation as an Approach to Interference with Polyamine Biosynthesis-An Alternative to Enzyme Inhibition," *Advances in Enzyme Regulation* 27:57-79.

Porter, C.W. et al. (1991). "Correlations Between Polyamine Analogue-induced Increases in Spermidine/Spermine $N^1$-Acetyltransferase Activity, Polyamine Pool Depletion, and Growth Inhibition in Human Melanoma Cell Lines," *Cancer Res.* 51(14):3715-3720.

Reddy, V. K. (1998). "Conformationally Restricted Analogues of $^1$N, $^{12}$N-bisethylspermine: Synthesis And Growth Inhibitory Effects On Human Tumor Cell Lines," *J. Med. Chem.* 41:4723-4732.

Reddy, V.K. et al. (2001). "*Cis*-Unsaturated Analogues of 3,8,13,18,23-Pentaazapentacosane (BE-4-4-4-4): Synthesis and Growth Inhibitory Effects on Human Prostate Cancer Cell Lines," *J. Med. Chem.* 44(3):404-417.

Redgate, E.S. et al. (1995). "Polyamines in Brain Tumor Therapy," *J. Neuro-Oncol.* 25(2):167-179.

Salaün, J. (1997). "Synthetic Potential and Bioactivity of Cyclopropanes," *Russian Journal of Organic Chemistry* 33(6):742-780.

Salaün, J. (2000). "Cyclopropane Derivatives and Their Diverse Biological Activities," *Topics in Current Chemistry* 207:1-67.

Salaün, J. et al. (1995). "Biologically Active Cyclopropanes and Cyclopropenes," *Current Medicinal Chemistry* 2(1):511-542.

Shappell, N.W. et al. (1992). "Differential Effects of the Spermine Analog, $N^1$, $N^{12}$-Bis(ethyl)-spermine, on Polyamine Metabolism and Cell Growth in Human Melanoma Cell Lines and Melanocytes," *Anticancer Research* 12(4):1083-1089.

Sharma, A. et al. (Aug. 1997). "Antitumor Efficacy of $N^1$, $N^{11}$-Diethylnorspermine on a Human Bladder Tumor Xenograft in Nude Athymic Mice," *Clinical Cancer Research* 3:1239-1244.

Snyder, R. D. et al., (1991) "Effects Of Polyamine Analogs On The Extent And Fidelity Of In Vitro Polypeptide Synthesis," *Biochem. Biophys. Res. Commun.* 176(3):1383-1392.

Snyder, R.D. et al. (1994). "Anti-Mitochondrial Effects of Bisethyl Polyamines in Mammalian Cells," *Anticancer Res.* 14(2A):347-356.

Sternberg, E. et al. (1996). "Pyrrolic Photosensitizers," *Current Medicinal Chemistry* 3(4):239-272.

Valasinas, A. et al. (2001). "Conformationally Restricted Analogues of $^1N$, $^{14}N$-Bisethylhomospermine (BE-4-4-4): Synthesis and Growth Inhibitory Effects on Human Prostate Cancer Cells," *J. Med. Chem.* 44(3):390-403.

Valasinas, A. et al. (2003). "Long-Chain Polyamines (Oligoamines) Exhibit Strong Cytotoxicities Against Human Prostate Cancer Cells," *Bioorganic and Medicinal Chemistry* 11:4121-4131.

Wamser, C.C. et al. (1989). "Thin-Film Composite Membranes for Artificial Photosynthesis. Final Report, Jul. 15, 1985-Mar. 31, 1989," *National Technical Information Service*, 41 pages.

Webb, H.K. et al. (1999). "1-(*N*-Alkylamino)-11-(*N*-ethylamino)-4,8-diazaundecanes: Simple Synthetic Polyamine Analogues That Differentially Alter Tubulin Polymerization," *J. Med. Chem.* 42(8):1415-1421.

Wunz, T.P. et al., (1987) "New Antitumor Agents Containing the Anthracene Nucleus," *J. Med. Chem.* 30(8):1313-1321.

Yuan, Z.M. et al. (1994). "Cytotoxic Activity of N1- and N8-Aziridinyl Analogs of Spermidine," *Biochemical Pharmacology* 47(9):1587-1592.

Zagaja, G.P. et al. (1998). "Effects of Polyamine Analogues on Prostatic Adenocarcinoma Cells in Vitro and in Vivo," *Cancer Chem. Pharm.* 41(6):505-512.

Cells in Vitro and in Vivo, *Cancer Chem. Pharm.* 41(6):505-512.

Amo-Ochoa, P. et al. (1996). "Cytotoxicity, DNA Binding, and Reactivity Against Nucleosides of Platinum (II) and (IV) Spermine Compounds," *Journal of Inorganic Biochemistry* 64:287-299.

Battaglia, Arturo et al. (2006). "Synthesis of 7- and 10-spermine conjugates of paclitaxel and 10-deacetyl-paclitaxel as potential prodrugs," *Tetrahedron Letters* 47:2667-2670.

Burns, M. R. et al. (2001). "Amino Acid/Spermine Conjugates: Polyamine Amides as Potent Spermidine Uptake Inhibitors," *J. Med. Chem.* 44(22):3682-3644.

Gardner, R. A. et al. (2004). "$N^1$-Substituent Effects in the Selective Delivery of Polyamine Conjugates into Cells Containing Active Polyamine Transporters," *J. Med. Chem.* 47(24):6055-6069.

Jakobs, A. et al. (1997). "Preparation of Tetracationic Metalloporphyrin-Spermine Conjugates," *J. Org. Chem.* 62(11):3505-3510.

Rauter, H. et al. (1997). "Selective Platination of Biologically Relevant Polyamines. Linear Coordinating Spermidine and Spermine as Amplifying Linkers in Dinuclear Platinum Complexes," *Inorg. Chem.* 36(18):3919-3927.

Siddiqui, A. Q. et al. (1999). "The Synthesis of Novel Polyamine-Nitroimidazole Conjugates Designed to Probe the Structural Specificities of the Polyamine Uptake System in A549 Lung Carcinoma Cells," *J. Chem. Soc. Perkin. Trans.* 1:3243-3252.

Notice of Allowability mailed Oct. 31, 2005 and Amendment filed Jul. 11, 2005 in U.S. Appl. No. 10/606,016.

Partial European Search Report mailed Aug. 3, 2006 for European Patent Application No. 06 00 9339, five pages.

* cited by examiner

SCHEME 1

SCHEME 2

SCHEME 3

SCHEME 4

SCHEME 5

SCHEME 6

SCHEME 7

SCHEME 8

SCHEME 9

SCHEME 10

SCHEME 11

SCHEME 12

SCHEME 13

SCHEME 14

SCHEME 15

SCHEME 16

SCHEME 17

SCHEME 18

SCHEME 19

SCHEME 20

SCHEME 21

SCHEME 24 (continued)

SCHEME 25

SCHEME 26

SCHEME 27

112 (SL-11161)

SCHEME 28

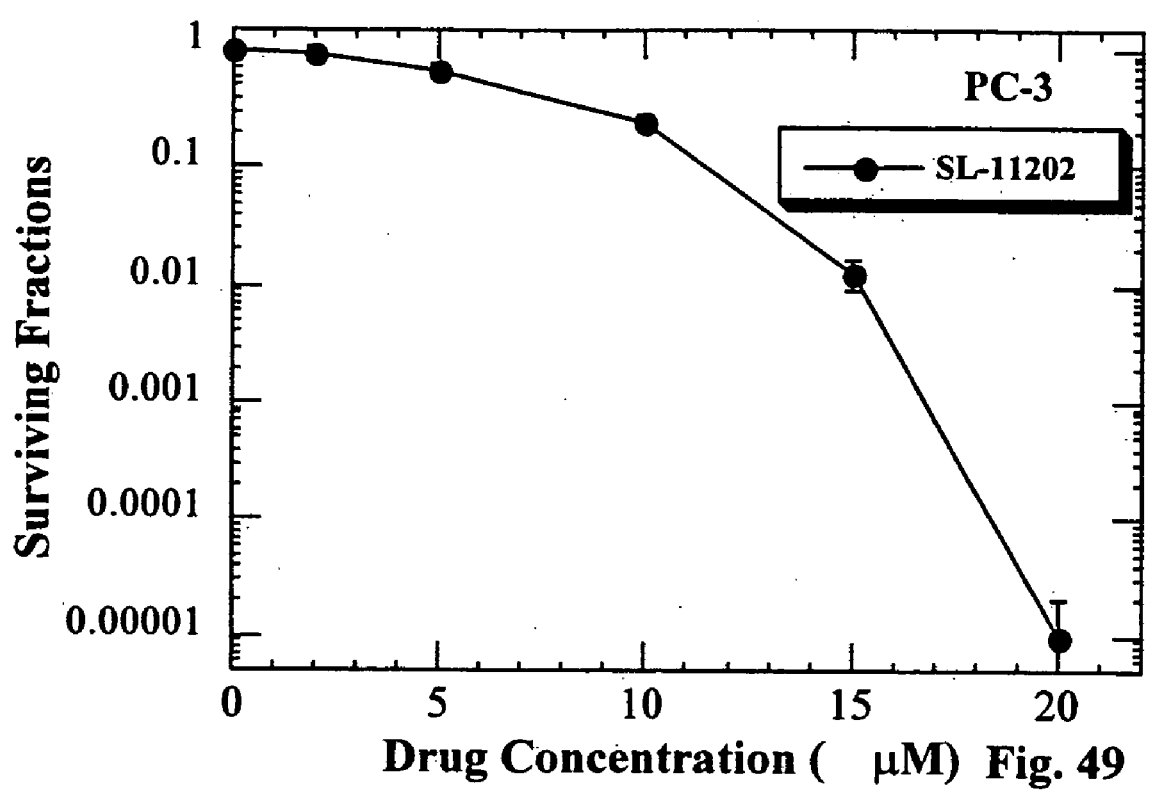

CONFORMATIONALLY RESTRICTED POLYAMINE ANALOGS AS DISEASE THERAPIES

CROSS-REFERENCE TO RELATED APPLICATIONS

This application is a divisional of and claims priority benefit of U.S. Patent application Ser. No. 09/560,711, filed Apr. 27, 2000 now U.S. Pat. No. 6,794,545, which claimed priority benefit of provisional patent application U.S. Ser. No. 60/131,779, filed on Apr. 30, 1999, now abandoned. The contents of those applications are hereby incorporated by reference herein in their entireties.

STATEMENT OF RIGHTS TO INVENTIONS MADE UNDER FEDERALLY SPONSORED RESEARCH

Not applicable.

TECHNICAL FIELD

This invention relates to conformationally restricted polyamine analogs, and to porphyrin-polyamine conjugates. This invention also relates to uses of these analogs or conjugates in various medicinal applications, including suppressing cell proliferation and treating various diseases, including cancer.

BACKGROUND OF THE INVENTION

Natural polyamines, e.g., spermidine, norspermidine, homospermidine, 1,4-diaminobutane (putrescine), and spermine, are simple aliphatic amines produced in eukaryotic cells by a highly regulated metabolic apparatus. Polyamine levels and the activity of the polyamine biosynthetic apparatus tend to be high in dividing mammalian cells and low in quiescent cells. Populations of cells depleted of their polyamine content stop growing and may die. Janne et al. (1978) *A. Biochim. Biophys. Acta.* 473:241 and Pegg et al. (1982) *Am. J. Cell. Physiol.* 243:212–221. Polyamines are reviewed in Morgan (1998) *Methods. Mol. Biol.* 79:3–30.

Several lines of evidence indicate that polyamines, particularly spermidine, are required for cell proliferation: (i) they are found in greater amounts in growing than in non-growing tissues; (ii) prokaryotic and eukaryotic mutants deficient in polyamine biosynthesis are auxotrophic for polyamines; and (iii) inhibitors specific for polyamine biosynthesis also inhibit cell growth. Despite this evidence, the precise biological role of polyamines in cell proliferation is uncertain. It has been suggested that polyamines, by virtue of their charged nature under physiological conditions and their conformational flexibility, might serve to stabilize macromolecules, such as nucleic acids, by anion neutralization. Hafner et al. (1979) *J. Biol. Chem.* 254:12419; Pohjatipelto et al. (1981) *Nature* 293:475; Mamont et al. (1978) *Biochem. Biophys. Res. Commun.* 81:58; Bloomfield et al. (1981) in *Polyamines in Biology and Medicine*, Morris et al., Eds., Dekker, New York, pp. 183–205.

A treatment approach has been devised based on the observation that increases in the polyamine pool suppress polyamine biosynthesis. Porter et al. (1988) in *Advances in Enzyme Regulation*, Pergamon Press, pp. 57–79. This approach attempts to identify polyamine analogs which down-regulate polyamine biosynthesis, but which do not perform the polyamine functions required for cell growth. BESPM, a N-bis(ethyl) analog of spermine, has served as a model compound for this strategy. BESPM rapidly suppresses polyamine biosynthetic enzymes, depletes natural polyamine pools, and inhibits cell growth in vitro. Porter et al. (1987) *Cancer Res.* 47:2821–2825. In addition, BESPM suppresses polyamine uptake (Byers et al. (1990) *J. Physiol.* 142:460–467; and Kramer et al. (1993) *J. Cell. Physiol.* 115:399–407), and thus minimizes the ability of tumor cells to meet their polyamine requirement by taking them up from their environment. BESPM and related analogs also induce the polyamine metabolizing enzyme spermidine/spermine $N^1$-acetyltransferase (SSAT) in certain human carcinoma cell lines.

BESPM and other polyamine analogs have been used, or proposed for use, in treating a large variety of diseases, including a number of different cancers. U.S. Pat. No. 5,541,230. Polyamine analogs demonstrated, for example, potent antitumor activity against several melanoma cell lines and tumors in vitro (Porter et al. (1991) *Cancer Res.* 51:3715–3720; Shappell et al. (1992) *Anticancer Res.* 12:1083–1090) and in vivo using tumors growing as xenografts in athymic mice (Bernacki et al. (1992) *Cancer Res.* 52:2424–2430; Porter et al. (1993) *Cancer Res.* 53:581–586). Potent antitumor activity of bis-ethyl spermine analogs has also been demonstrated for pancreatic cancer cell lines in vitro (Chang et al. (1992) *Cancer Chemother. Pharmacol.* 30:183–188) and in vivo (Chang et al. (1992) *Cancer Chemother. Pharmacol.* 30:179–182). Polyamine analogs have also been suggested for use in treating brain tumor therapy. Redgate et al. (1995) *J. Neurooncol.* 25:167–79. In addition to being useful against cancers of the brain, pancreas, and skin, polyamine analogs are also useful against cancers of the bladder, bone, breast, colon, digestive tract, lung and ovaries. Chang et al. (1993) *J. Urol.* 150: 1293–7; Snyder et al. (1994) *Anticancer Res.* 14:347–56; Yuan et al. (1994) *Biochem. Pharmacol.* 47:1587–92; Davidson et al. (1993) *Cancer Res.* 53:2071–5; Berchtold et al. (1998) *J. Cell. Physiol.* 174:380–6; Porter et al. (1988) *Adv. Exp. Med. Biol.* 250:677–90; U.S. Pat. Nos. 5,498,522 and 5,374,658. U.S. Pat. No. 5,498,522 presents the use of spermidine/spermine $N^1$-acetyltransferase as a prognostic indicator of the efficacy of a polyamine analog against a malignant tumor.

Polyamine analogs have been used to treat cancer of the prostate. Mi et al. (1988) *Prostate* 34:51–60. Polyamines are produced in large amounts by the prostate gland and are abundant in the seminal fluid. Herr et al. (1984) *Cancer* 53:1294–8. Polyamine analogs such as BE-4444, BE-373, and BE-333 are particularly effective in inhibiting prostate xenograft tumors in nude mice. Zagaja et al. (1998) *Cancer Chem. Pharm.* 41:505–512; Jeffers et al. (1997) *Cancer Chem. Pharm.* 40:172–179; Feuerstein et al. (1991) *J. Cell. Biochem.* 46:37–47; and Marton et al. (1995) *Ann. Rev. Pharm. Toxicol.* 35:55–91.

In addition to treating cancer, polyamines and their analogs have uses in treating a number of other diseases and in numerous other medicinal applications. Oxidized polyamines are believed to inhibit growth of parasites (Morgan et al. (1983) *Adv. Polyamine Res.* 4: 169–174; Morgan et al. (1986) *Biochem. J.* 236:97–101; and U.S. Pat. No. 4,935,449) and suppress infectivity of selected strains of bacteria and fungi (Bachrach et al. (1971) *J. Gen. Virol.* 13:415–22; Nishimura et al. (1971) *Biochim. Biophys. Acta* 247:153–6; and U.S. Pat. No. 5,744,453). Polyamines such as spermine and polyamine analogs are also anti-viral and some are anti-insecticidal. Bachrach et al. (1972) *Appl. Microbiol.* 23:232–5; Bachrach et al. (1971) *J. Gen. Virol.*

11:1–9; U.S. Pat. Nos. 5,021,409; 5,606,053; 5,608,061; 5,612,478; and 5,681,837. In addition, oxidized polyamines, such as spermine dialdehyde, for example, can be used in treatment of tissue grafts and other organs for transplantation. U.S. Pat. No. 5,374,658. Polyamine analogs can also be used to treat neurodegenerative diseases and neurotrauma such as stroke. U.S. Pat. Nos. 5,646,188 and 5,677,349. Polyamine analogs have also been reported to be useful as anti-psoratic agents, and in the treatment of epilepsy, Alzheimer's disease, and multiple sclerosis, as described in U.S. Pat. No. 5,646,188. Polyamine analogs are also useful in treating and preventing restenosis. U.S. Pat. No. 5,516,807. Polyamine analogs are also useful in treatment of gastric ulcers. Igarashi et al. (1990) *Biochem. Biophys. Res. Commun.* 172:715–20. In addition, polyamine derivatives including N-alkythio polyamine derivatives, polyamine thiols, and polyamine phenols are useful as radioprotective agents for normal tissues during radiotherapy. U.S. Pat. Nos. 5,217,964; 5,354,782; and 5,434,145.

Polyamines and their analogs can be administered alone or in conjunction with additional agents. For example, therapeutic polyamines can be administered along with 1,3-bis (2-chloroethyl)-1-nitrosourea. U.S. Pat. No. 5,541,230. In treating cancer, polyamines can be co-administered with various cytotoxic agents, including antineoplastic vinca alkaloids, antibiotics, antimetabolites, and platinum coordination complexes. U.S. Pat. No. 5,654,287.

In addition to the various aforementioned medicinal uses, polyamines and polyamine analogs have a variety of industrial uses, including derivativization of silica. U.S. Pat. No. 5,763,388. Polyamines have also been used in conjunction with other clarification aids to treat wastewaters. U.S. Pat. Nos. 5,413,719 and 5,707,532. The combination of aluminum chlorohydrate and a polyamine is an effective emulsion breaker for reverse (oil-in-water) emulsions, e.g. in a matrix comprising mostly oil as encountered in a crude oil desalter unit. U.S. Pat. No. 5,607,574. Polyamines are also useful in deodorizing polysulfides. U.S. S.I.R. H1,633. Polyamines are also used in industrial dyes. U.S. Pat. No. 5,672,202. Polyamines and hot water can also be used in manufacturing microcapsules. U.S. Pat. No. 5,401,443. The antioxidative and metal-chelating effects of polyamines are reviewed in Lovaas (1997) *Adv. Pharmacol.* 38:119–149.

It would be advantageous to develop novel polyamine analogs for various uses, including disease treatment.

All references cited herein are hereby incorporated by reference in their entirety.

SUMMARY OF THE INVENTION

The invention provides novel polyamine analogs, compositions comprising a polyamine analog, and methods using the analogs and compositions. In one embodiment, the polyamine analog is conformationally restricted.

In another embodiment, the polyamine analog is selected from among compounds of the formula:

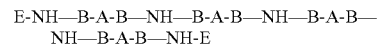

where A is independently selected from the group consisting of a single bond, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; B is independently selected from the group consisting of: a single bond, $C_1$–$C_6$ alkyl, and $C_2$–$C_6$ alkenyl; and E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; with the proviso that either at least one A moiety is selected from the group consisting of $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, or at least one B moiety is selected from the group consisting of $C_2$–$C_6$ alkenyl; and all salts and stereoisomers thereof. Specific embodiments of compounds of this type include

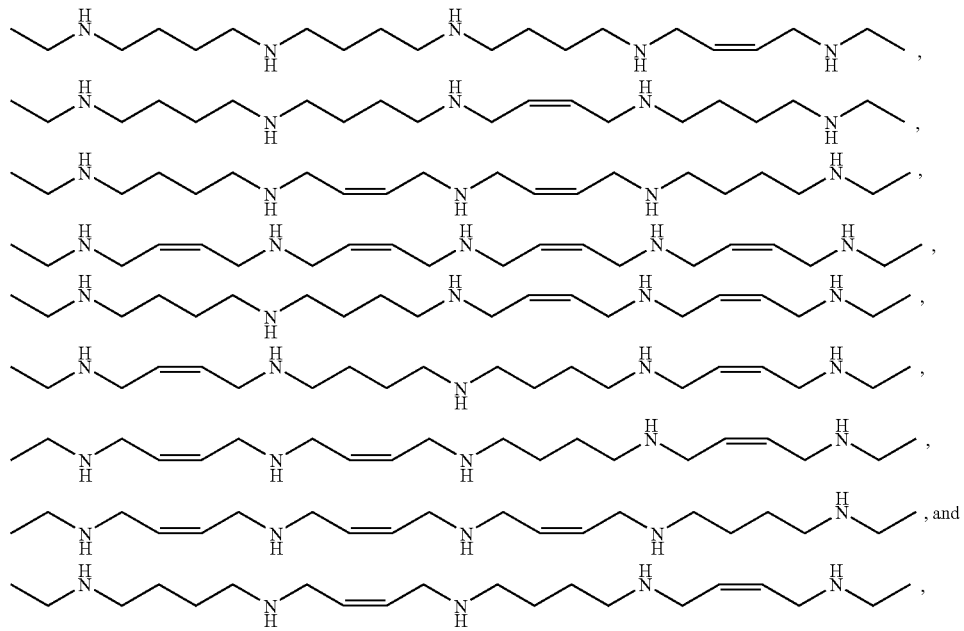

and all salts and stereoisomers thereof.

In another embodiment, the polyamine analog is selected from the group of compounds of the formula:

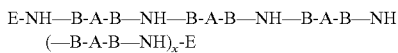

wherein A is independently selected from the group consisting of a single bond, $C_6$–$C_2$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; B is independently selected from the group consisting of a single bond, $C_1$–$C_6$ alkyl, and $C_2$–$C_6$ alkenyl; E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and x is an integer from 2 to 16; with the proviso that either at least one A moiety is selected from the group consisting of $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, or at least one B moiety is selected from the group consisting of $C_2$–$C_6$ alkenyl; and all salts and stereoisomers thereof. Specific embodiments of compounds of this type include

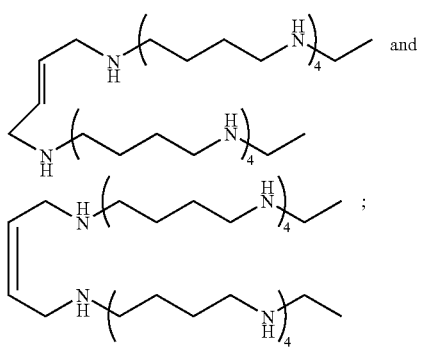

and all salts and stereoisomers thereof.

In another embodiment, the polyamine analog is selected from among the group of compounds of the formula

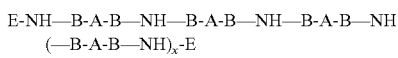

wherein A is independently selected from the group consisting of a single bond, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; B is independently selected from the group consisting of a single bond, $C_1$–$C_6$ alkyl, and $C_2$–$C_6$ alkenyl; E is independently selected from the group consisting of $C_1$–$C_6$ alkyl, $C_1$–$C_6$ alkanol, $C_3$–$C_6$ cycloalkanol, and $C_3$–$C_6$ hydroxyaryl, with the proviso that at least one E moiety be selected from the group consisting of $C_1$–$C_6$ alkanol, $C_3$–$C_6$ cycloalkanol, and $C_3$–$C_6$ hydroxyaryl; and x is an integer from 0 to 16; and all salts or stereoisomers thereof.

Specific embodiments of compounds of this type include

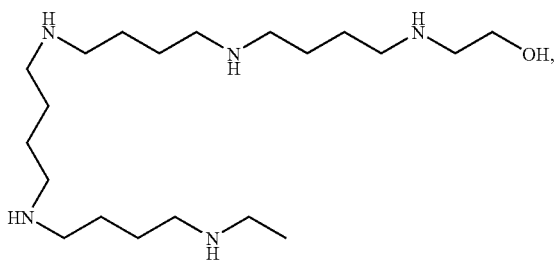

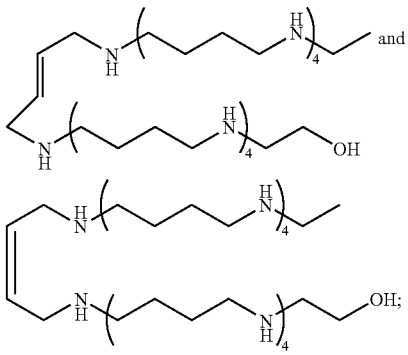

and all salts and stereoisomers thereof.

In another embodiment, the polyamine analog is selected from among the group of compounds of the formula

wherein A is selected from the group consisting of $C_2$–$C_6$ alkynyl; B is independently selected from the group consisting of: a single bond, $C_1$–$C_6$ alkyl, and $C_2$–$C_6$ alkenyl; D is independently selected from the group consisting of $C_1$–$C_6$ alkyl, $C_2$–$C_6$ alkenyl, $C_2$–$C_6$ alkynyl, $C_3$–$C_6$ cycloalkyl, $C_3$–$C_6$ cycloalkenyl, and $C_3$–$C_6$ cycloaryl; and E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and all salts and stereoisomers thereof. Specific embodiments of compounds of this type include

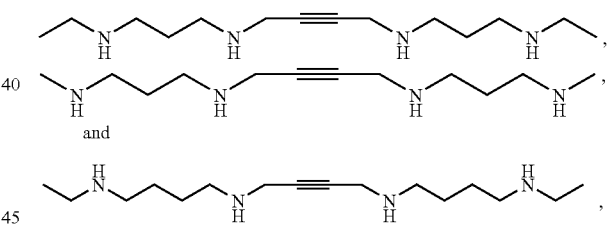

and all salts and stereoisomers thereof.

In another embodiment, the polyamine analog is selected from among the group of compounds of the formula

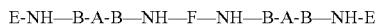

wherein F is selected from the group consisting of $C_1$–$C_6$ alkyl; A is independently selected from the group consisting of: a single bond, $C_1$–$C_6$ alkyl; $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; B is independently selected from the group consisting of: a single bond, $C_1$–$C_6$ alkyl, and $C_2$–$C_6$ alkenyl; and E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; with the proviso that either at least one A moiety is selected from the group consisting of $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, or a least one B moiety is selected from the group consisting of $C_2$–$C_6$ alkenyl; and all salts and stere oisomers thereof. Specific embodiments of compounds of this type include

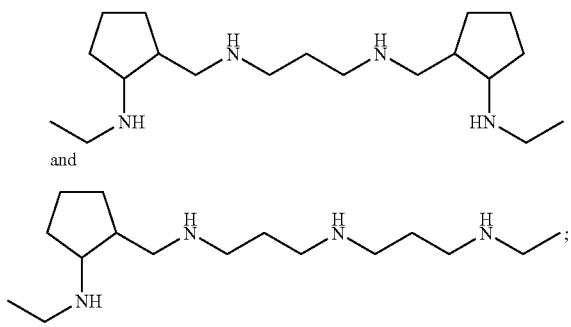

and all salts and stereoisomers thereof.

In another embodiment, the polyamine analog is selected from among the group of compounds of the formula

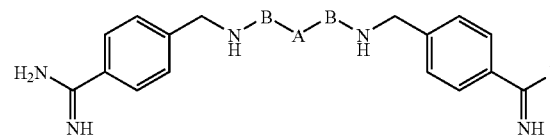

wherein A is independently selected from the group consisting of a single bond, $C_1$–$C_6$ alkyl; $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; B is independently selected from the group consisting of: a single bond, $C_1$–$C_6$ alkyl, and $C_2$–$C_6$ alkenyl; with the proviso that A and both B moieties are not all a single bond; and all salts and stereoisomers thereof. Specific embodiments of compounds of this type include In another embodiment, the polyamine analog is selected from among the group of compounds of the formula

E-NH-D-NH—B-A-B—NH-D-NH-E wherein A is selected from the group consisting of $C_1$–$C_6$ alkyl, $C_2$–$C_6$ alkenyl, $C_2$–$C_6$ alkynyl, $C_3$–$C_6$ cycloalkyl, $C_3$–$C_6$ cycloalkenyl, and $C_3$–$C_6$ cycloaryl; B is independently selected from the group consisting of: a single bond, $C_1$–$C_6$ alkyl, and $C_2$–$C_6$ alkenyl; D is independently selected from the group consisting of $C_1$–$C_6$ alkyl, $C_2$–$C_6$ alkenyl, $C_2$–$C_6$ alkynyl, $C_3$–$C_6$ cycloalkyl, $C_3$–$C_6$ cycloalkenyl, and $C_3$–$C_6$ cycloaryl; and E is independently selected from the group consisting of H and $C_1$–$C_6$ alkyl; with the proviso that either at least one A moiety is selected from the group consisting of $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, or at least one B moiety is selected from the group consisting of $C_2$–$C_6$ alkenyl; and the proviso that at least one E is selected from the group consisting of H or methyl; and all salts and stereoisomers thereof. A specific embodiment of compounds of this type includes

and all salts and stereoisomers thereof.

In another embodiment, the polyamine analog is selected from among the group of compounds of the formula

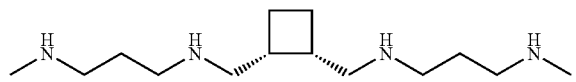

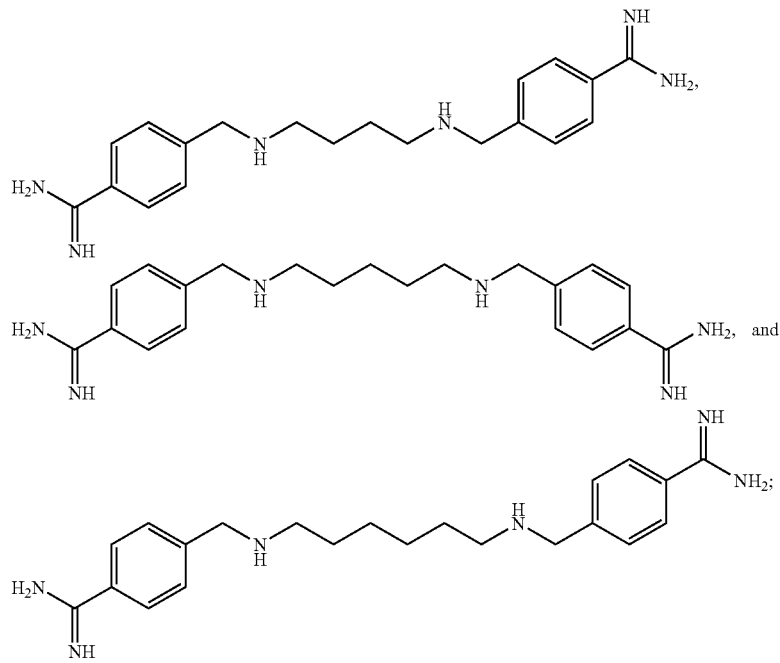

and all salts and stereoisomers thereof.

wherein A is trans-ethene (no stereochemical variation about the double bond being permitted, that is, cis-ethene is specifically excluded); B is independently selected from the group consisting of: a single bond, $C_1$–$C_6$ alkyl, and $C_2$–$C_6$ alkenyl; D is independently selected from the group consisting of $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, with the proviso that D is not $C_3$ alkyl; and E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and all salts thereof.

In another embodiment the invention also provides conjugates of polyamines to porphyrin compounds, where the polyamines are linked via a covalent bond to the porphyrin compound. Polyamines useful for this embodiment of the invention include, but are not limited to, the polyamines described in the previous embodiments, or the polyamines depicted in Table 1. The covalent bond can be an amide bond, an amine bond, or any other suitable covalent bond. The polyamine analogs can be bound to the porphyrin compound at positions including, but not limited to, any of the peripheral positions of the porphyrin macrocycle such as the β-pyrrole positions or the meso carbons of the macrocycle. Non-limiting examples of these compounds are given in Table 2.

In one embodiment, the porphyrin-polyamine compounds are of the formula

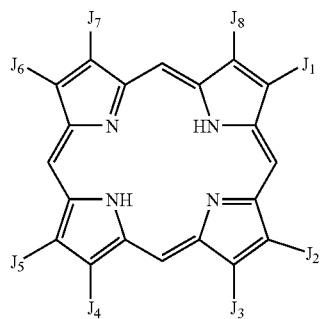

where at least one of $J_1$–$J_8$ is independently selected from the group consisting of —$K_1$-G-L-(N(P)-A)$_n$-$K_2$; where $K_1$ is independently selected from the group consisting of $C_1$–$C_8$ alkyl and where the valence to the left of $K_1$ attaches to the porphyrin ring; where G is —O—, —(C=O)—, —C(=O)—O—, —O—(C=O)—, —O—(C=O)—O—, —O—(C=O)—N—, —N—(C=O)—O—, or a nonentity; where L is $C_1$–$C_8$ alkyl, $C_3$–$C_8$ cycloalkyl, $C_3$–$C_8$ cycloaryl, $C_1$–$C_8$ alkoxy, $C_1$–$C_8$ alkyl-$C_3$–$C_8$ cycloalkyl, $C_1$–$C_8$ alkyl-$C_3$–$C_8$ cycloaryl, $C_1$–$C_8$ alkoxy-$C_3$–$C_8$ cycloaryl, $C_3$–$C_8$ cycloalkyl-$C_3$–$C_8$ cycloaryl, $C_3$–$C_8$ cycloalkyl-$C_1$–$C_8$ alkyl, $C_3$–$C_8$ cycloaryl-$C_1$–$C_8$ alkyl, $C_3$–$C_8$ cycloaryl-$C_1$–$C_8$ alkoxy, $C_3$–$C_8$ cycloaryl-$C_3$–$C_8$ cycloalkyl, or a nonentity; each A is independently selected from the group consisting of $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, and $C_3$–$C_8$ cycloalkynyl; P is selected from the group consisting of H and $C_1$–$C_8$ alkyl; n is an integer from 2 to 8; and $K_2$ is independently selected from the group consisting of H, $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, $C_3$–$C_8$ cycloalkynyl, $C_1$–$C_8$ alkanol, $C_3$–$C_8$ cycloalkanol, and $C_3$–$C_8$ hydroxyaryl; where the remainder of the groups $J_1$–$J_8$ are each independently selected from the group consisting of H, $K_3$, or $K_4$—COOH, where $K_3$ is independently selected from the group consisting of $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, $C_3$–$C_8$ cycloalkynyl, $C_1$–$C_8$ alkanol, $C_3$–$C_8$ cycloalkanol, and $C_3$–$C_8$ hydroxyaryl; and $K_4$ is independently selected from the group consisting of $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, and $C_3$–$C_8$ cycloalkynyl; and any salt or stereoisomer thereof.

Additional embodiments include those where $K_1$ and each A are independently selected from the group consisting of $C_1$–$C_8$ alkyl, $K_2$ is independently selected from the group consisting of H and $C_1$–$C_8$ alkyl, and the remainder of the groups $J_1$–$J_8$ are each independently selected from the group consisting of H, $K_3$, or $K_4$—COOH, where $K_3$ and $K_4$ are independently selected from the group consisting of $C_1$–$C_8$ alkyl. In additional embodiments, $K_1$ is —$CH_2$—$CH_2$— or —$CH_2$—$CH_2$—$CH_2$—. In additional embodiments, n is 4. In yet additional embodiments, $J_3$, $J_4$, $J_7$ and $J_8$ of the formula depicted above are independently selected from the group consisting of $C_1$–$C_3$ alkyl; $J_5$ and $J_6$ are independently selected from the group consisting of $C_1$–$C_3$ alkyl and $C_1$–$C_3$ alkyl-COOH; and $J_1$ and $J_2$ are independently selected from the group consisting of $C_1$–$C_3$ alkyl-G-N($P_1$)-A-(NH-A)$_{n1}$-$K_5$;

where G is —(C=O)— or a nonentity; $P_1$ is H or $C_1$–$C_3$ alkyl; each A is independently selected from the group consisting of $C_1$–$C_8$ alkyl; $n_1$ is 3 or 4; and $K_5$ is independently selected from the group consisting of H and $C_1$–$C_8$ alkyl.

The invention also includes methods of treating an indication in an individual comprising the step of administering to the individual a therapeutic amount of a porphyrin-polyamine conjugate of the invention.

The invention also provides methods of treating an indication comprising the step of administering to the individual an effective amount of a composition comprising a polyamine analog, preferably a conformationally restricted polyamine analog.

In one method, the indication is cancer. In various embodiments, the cancer affects cells of the bladder, blood, brain, breast, colon, digestive tract, lung, ovaries, pancreas, prostate gland, or skin. In other embodiments, the indication can also include, but is not limited to, Alzheimer's disease, epilepsy, multiple sclerosis, problems associated with tissue grafts and organ transplants, psoriasis, restenosis, stomach ulcers, or tissue overgrowth after surgery. In other embodiments, the indication is an infection or infestation of parasites, bacteria, fungi or insects. The polyamine analog or porphyrin-polyamine conjugate is selected from the foregoing groups of compounds.

(□), SL-11123 (■), SL-11126 (Δ), SL-11127 (▲), SL-11128 (◇), SL-11129 (♦), SL-11130 (▽), and SL-11133 (▼) on the survival of cultured human prostate cancer cells DU145.

$ED_{50}$ of BE-4444=0.07 μM, SL-11121=0.08 μM, SL-11122=0.08 μM, SL-11123=0.51 μM, SL-11126=0.51 μM SL-11127 0.22 μM, SL-11128=0.14 μM, SL-11129=0.32 μM, SL-11130=0.43 μM, and SL-11133=0.34 μM.

Figure 1:
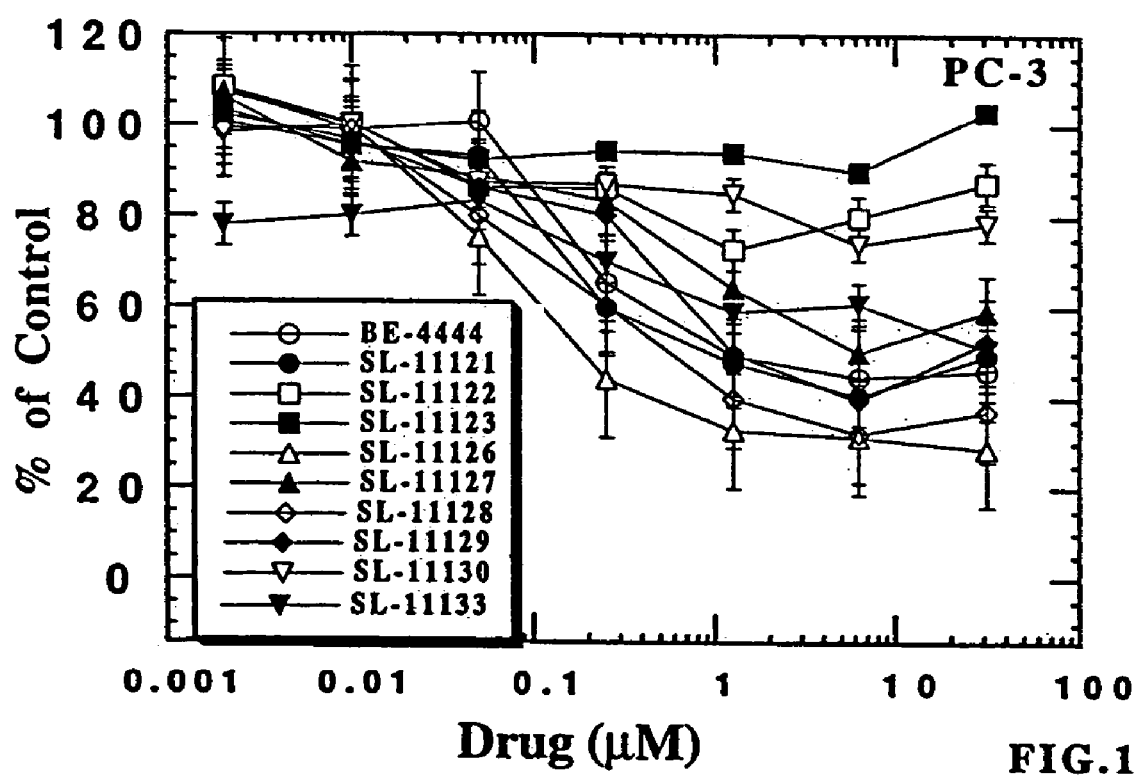
FIG. 1 is a graph depicting the in vitro effect of increasing concentrations of BE-4444 (○), SL-11121 (●), SL-11122 (□), SL-11123 (■), SL-11126 (Δ), SL-11127 (▲), SL-11128 (◇), SL-11129 (◆), SL-11130 (▽), SL-11133 (▼) on the survival of cultured human prostate cancer cells PC3. $ED_{50}$ of BE-4444=0.6 μM, SL-11121=0.52 μM, SL-11122>31.25 μM, SL-11123>31.25 μM, SL-11126=0.2 μM SL-11127>31.25 μM, SL-11128=0.5 μM, SL-11129=1.7 μM, SL-11130>31.25 μM, and SL-11133>31.25 μM.
Figure 2:
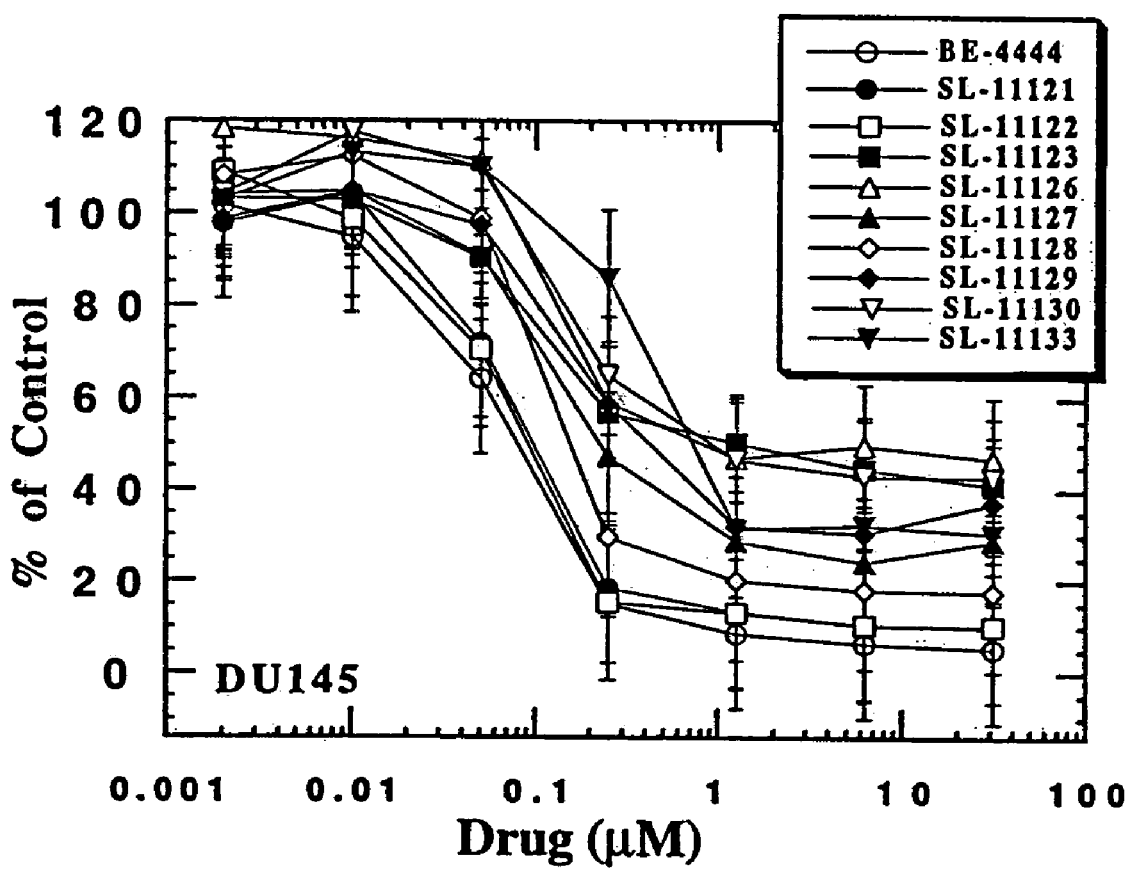
FIG. 2 is a graph depicting the in vitro effect of increasing concentrations of BE-4444(○), SL-11121 (●), SL-11122
Figure 3:
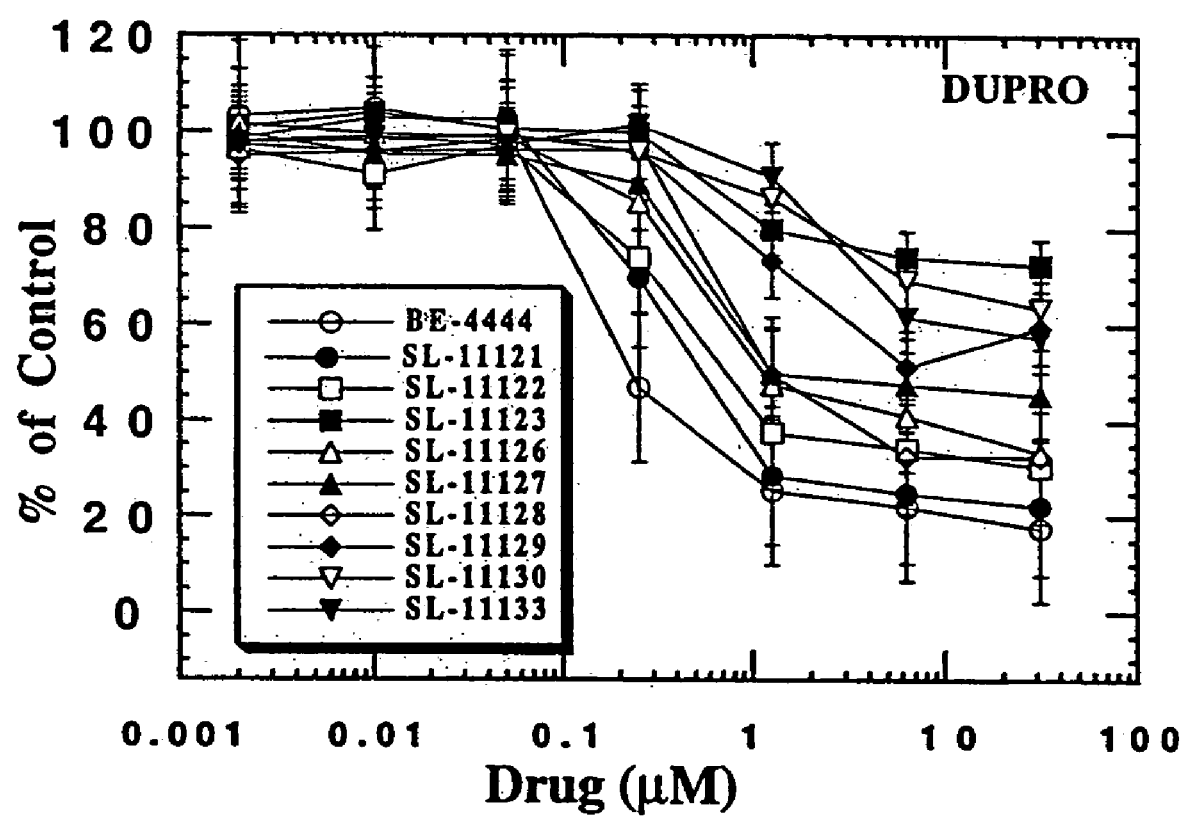

FIG. 3 is a graph depicting the in vitro effect of increasing concentrations of BE-4444(○), SL-11121 (●), SL-11122 (□), SL-11123 (●), SL-11126 (Δ), SL-11127 (▲), SL-11128 (◇), SL-11129 (♦), SL-11130 (▽), and SL-11133 (▼) on the survival of cultured human prostate cancer cells DUPRO.

$ED_{50}$ of BE-4444=0.2 μM, SL-11121=0.4 μM, SL-11122=0.56 μM, SL-11123>31.25 μM, SL-11126=1.1 μM, SL-11127 1.3 μM, SL-11128=1.28 μM, SL-11129>31.25 μM, SL-11130>31.25 μM, and SL-11133=31.25 μM.

Figure 4:
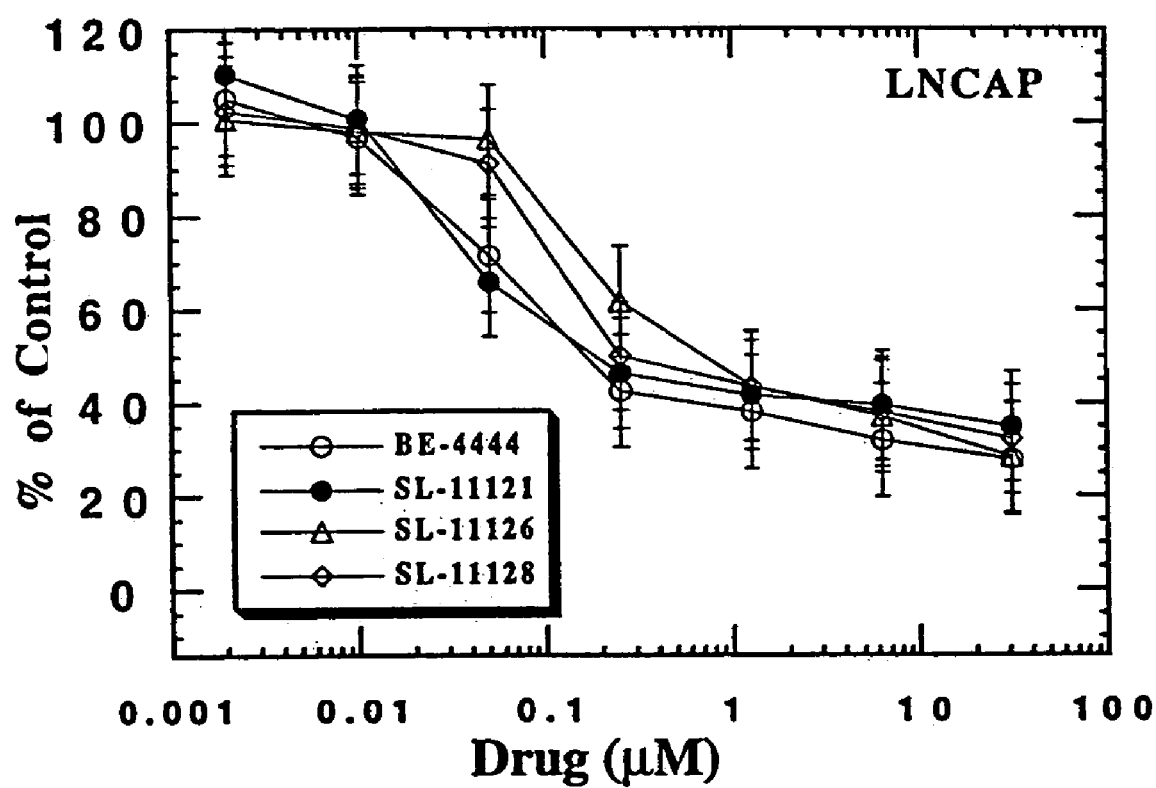

FIG. 4 is a graph depicting the in vitro effect of increasing concentrations of BE-4444 (○), SL-11121 (●), SL-11126 (Δ), SL-11128 (◇), on the survival of cultured human prostate cancer cells LNCAP.

$ED_{50}$ of BE-4444=0.14 μM, SL-11121=0.14 μM, SL-11126=0.55 μM and SL-11128=0.3 μM.

Figure 5:
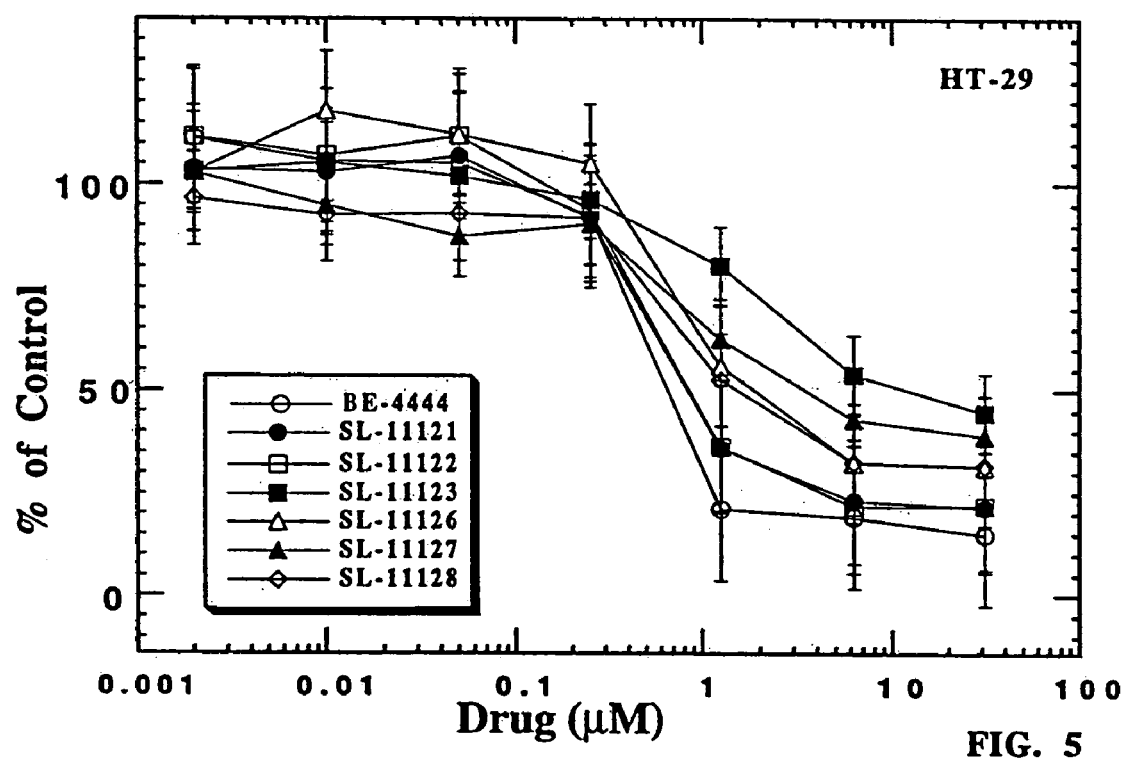

FIG. 5 is a graph depicting the in vitro effect of increasing concentrations of BE-4444 (○), SL-11121 (●), SL-11122 (□), SL-11123 (■), SL-11126 (Δ), SL-11127 (▲), and SL-11128 (◇) on the survival of cultured human colon cancer cells HT29.

$ED_{50}$ of BE-4444=0.5 μM, SL-11121=0.8 μM, SL-11122=0.8 μM, SL-11123=10.42 μM, SL-11126=1.5 μM, SL-11127=2.91 μM, and SL-11128=1.35 μM.

Figure 6:
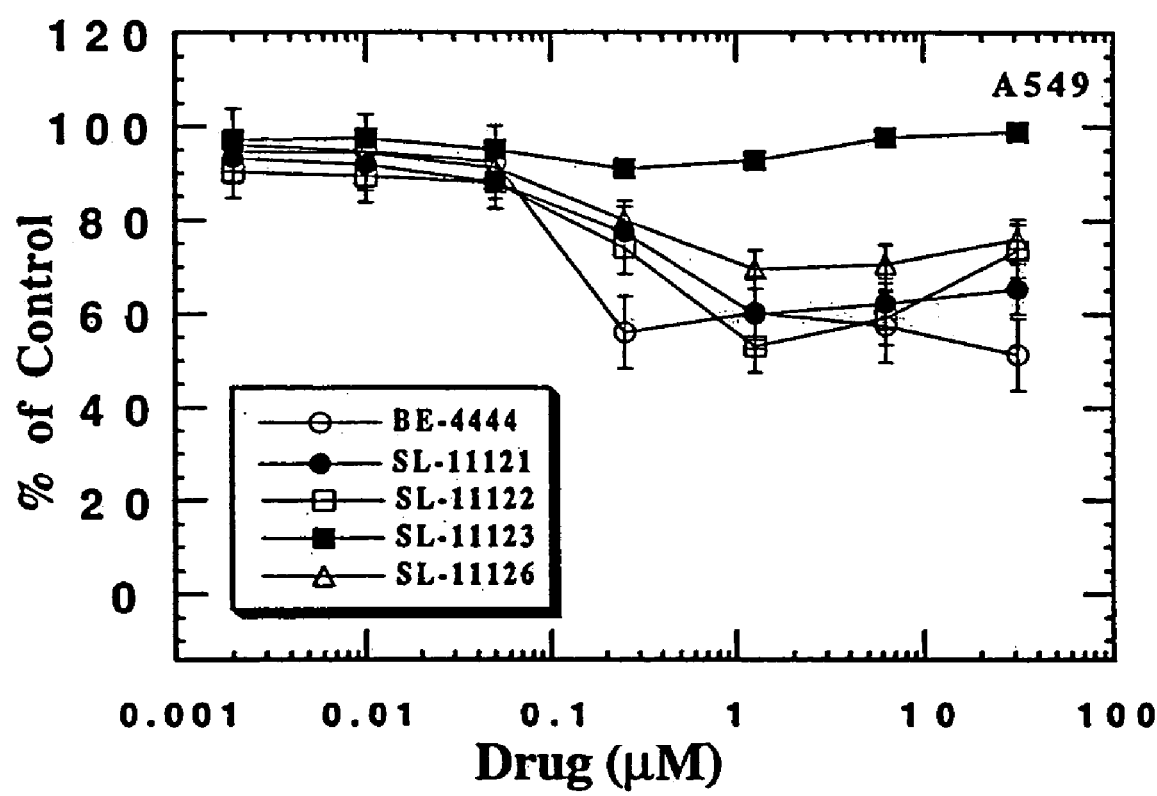

FIG. 6 is a graph depicting the in vitro effect of increasing concentrations of BE-4444 (○), SL-11121 (●), SL-11122 (□), SL-11123 (■), and SL-11126 (Δ) on the survival of cultured human lung cancer cells A549.

$ED_{50}$ of BE-4444>31.25 μM, SL-11121>31.25 μM, SL-11122>31.25 μM, SL-11123>31.25 μM, and SL-11126>31.25 μM.

Figure 7:
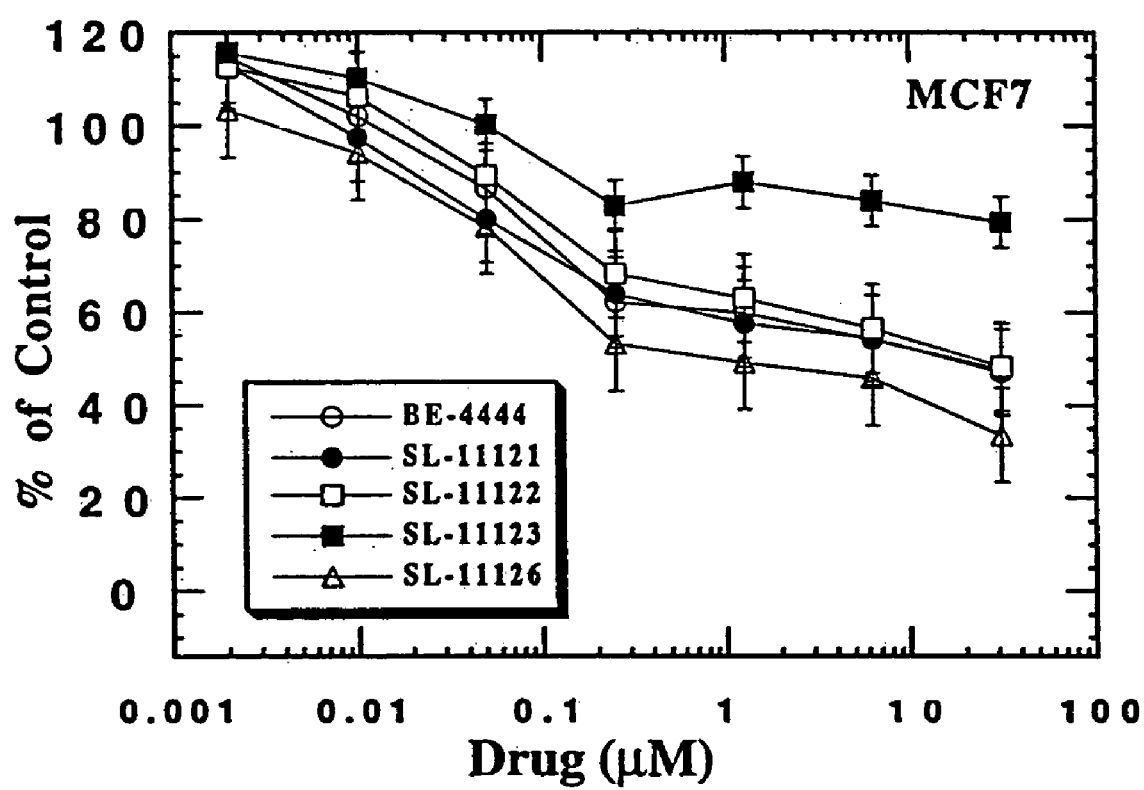

FIG. 7 is a graph depicting the in vitro effect of increasing concentrations of BE-4444 (○), SL-11121 (●), SL-11122 (□), SL-11123 (■), and SL-11126 (Δ) on the survival of cultured human breast cancer cells MCF7.

$ED_{50}$ of BE-4444>31.25 μM, SL-11121=17.0 μM, SL-11122>31.25 μM, SL-11123>31.25 μM, and SL-11126=0.7 μM.

Figure 8:
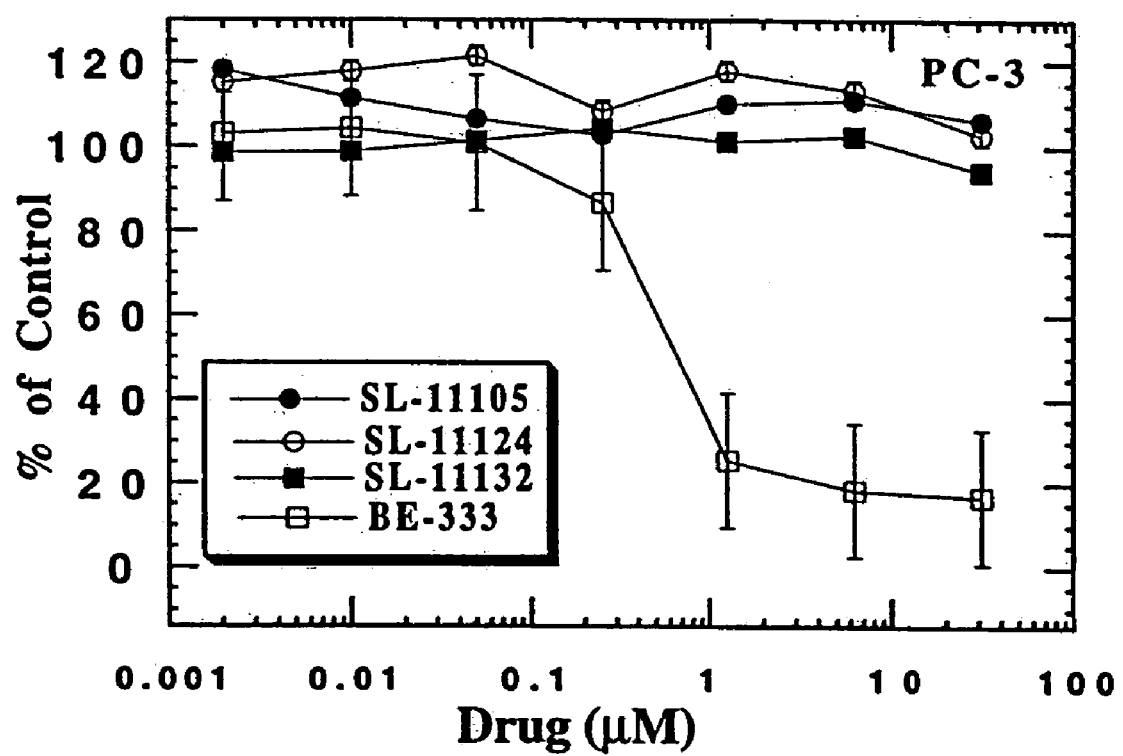

FIG. 8 is a graph depicting the in vitro effect of increasing concentrations of SL-11105 (●), SL-11124 (○), SL-11132 (■), and BE-333 (□) on the survival of cultured human prostate cancer cells PC3.

$ED_{50}$ of SL-11105>31.25 μM, SL-11124>31.25 μM, SL-11132>31.25 μM and BE-333=0.34 μM.

Figure 9:
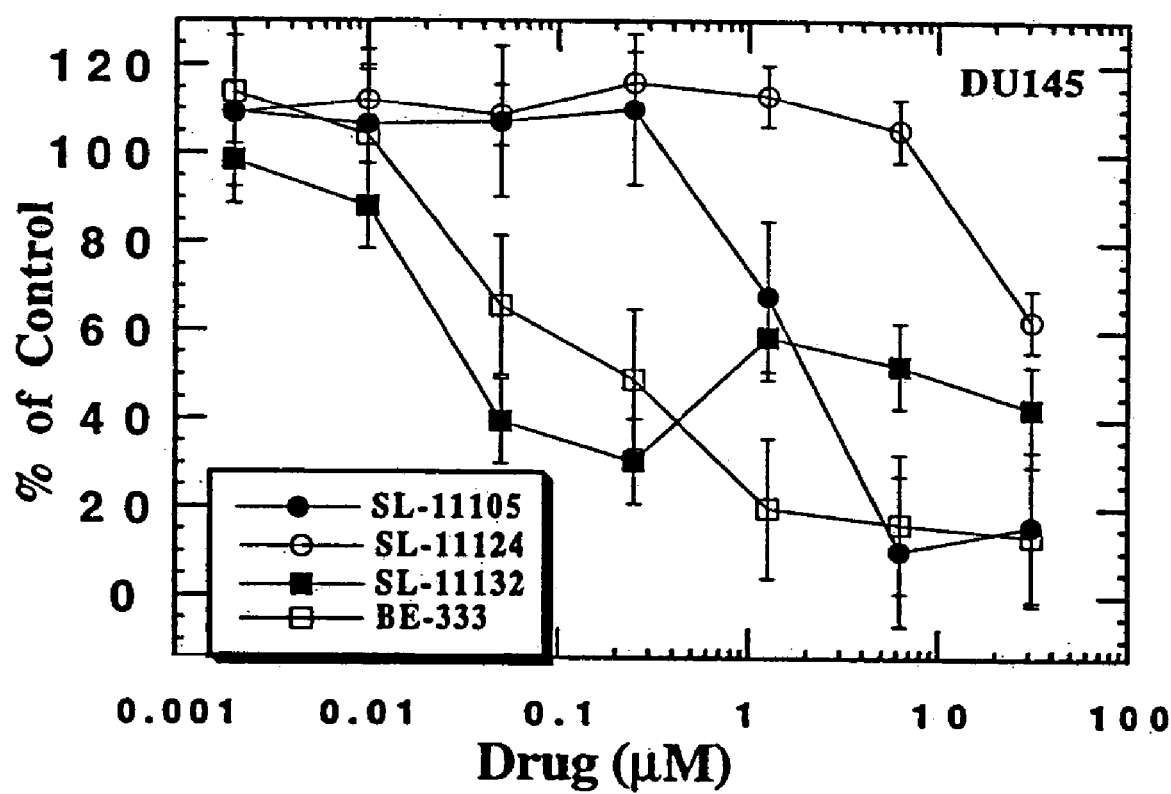

FIG. 9 is a graph depicting the in vitro effect of increasing concentrations of SL-11105 (●), SL-11124 (○), SL-11132 (■), and BE-333 (□) on the survival of cultured human prostate cancer cells DU145.

$ED_{50}$ of SL-11105=1.6 μM, SL-11124>31.25 μM, SL-11132=0.015 μM and BE-333=0.12 μM.

Figure 10:
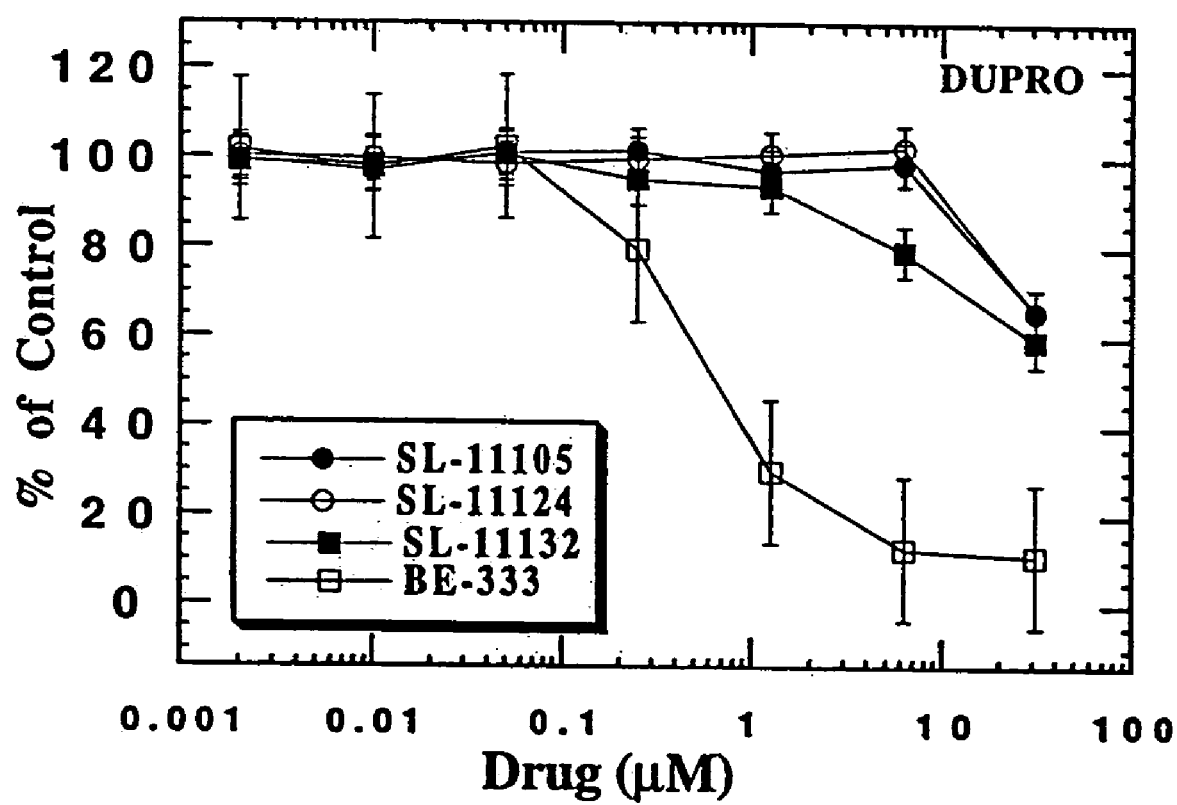

FIG. 10 is a graph depicting the in vitro effect of increasing concentrations of SL-11105 (●), SL-11124 (○), SL-11132 (■), and BE-333 (□) on the survival of cultured human prostate cancer cells DUPRO.

$ED_{50}$ of SL-11105=0.43 μM, SL-11124>31.25 μM, SL-11132>31.25 μM and BE-333=0.9 μM.

Figure 11:
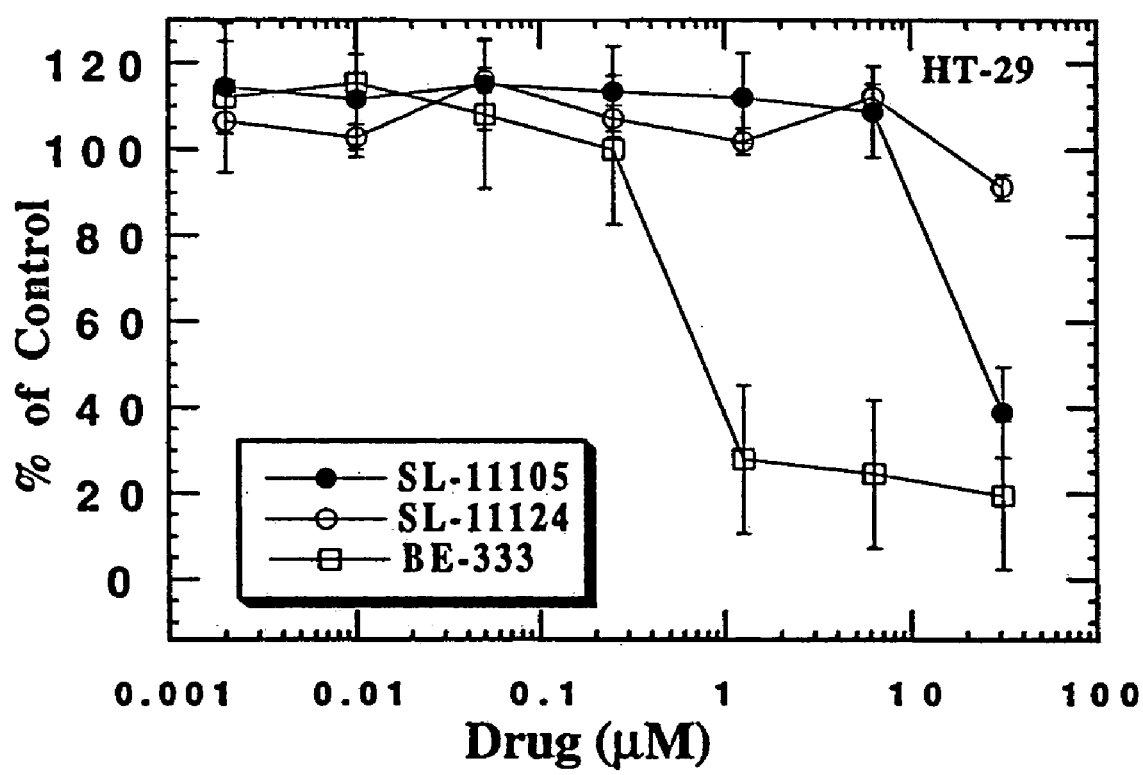

FIG. 11 is a graph depicting the in vitro effect of increasing concentrations of SL-11105 (●), SL-11124 (○), and BE-333 (□) on the survival of cultured human colon cancer cells HT29.

$ED_{50}$ of SL-11105=25.2 μM, SL-11124>31.25 μM, and BE-333=0.3 μM.

Figure 12:
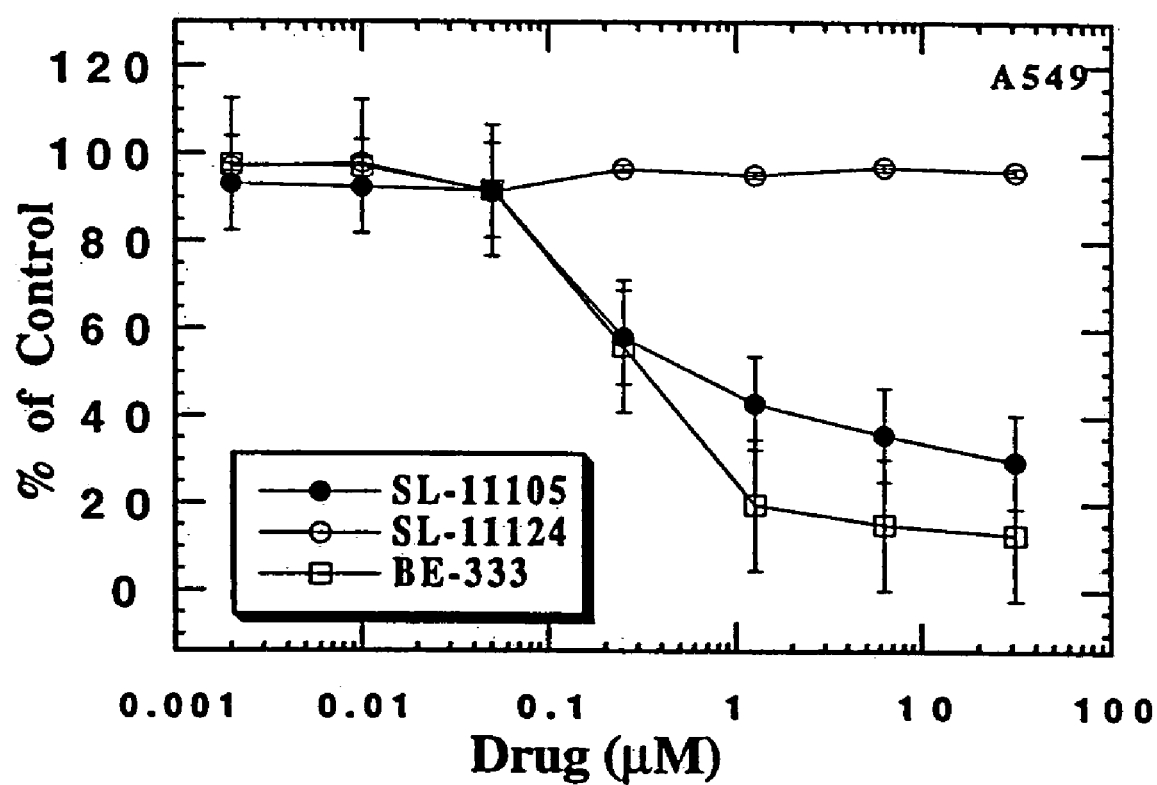

FIG. 12 is a graph depicting the in vitro effect of increasing concentrations of SL-11105 (●), SL-11124 (○), and BE-333 (□) on the survival of cultured human lung cancer cells A549.

$ED_{50}$ of SL-11105=0.43 μM, SL-1124>31.25 μM, and BE-333=0.3 μM.

Figure 13:
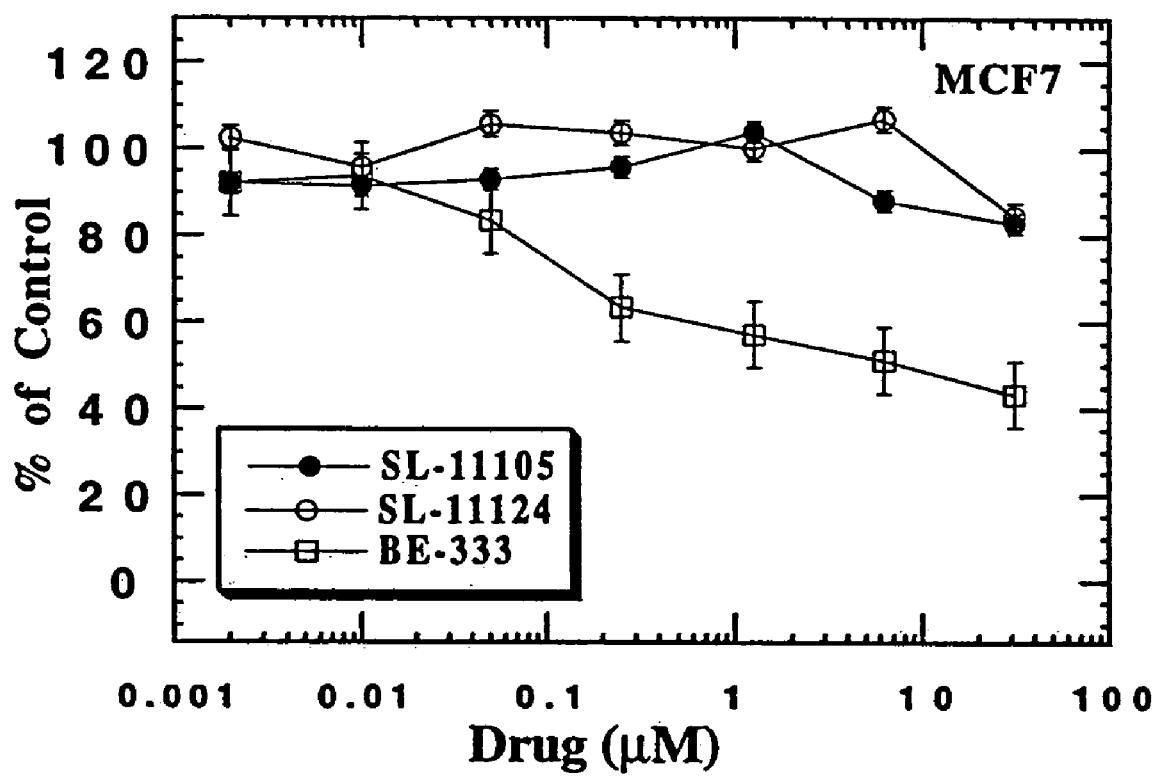

FIG. 13 is a graph depicting the in vitro effect of increasing concentrations of SL-11105 (●), SL-11124 (○), and BE-333 (□) on the survival of cultured human breast cancer cells MCF7.

$ED_{50}$ of SL-11105>31.25 μM, SL-11124>31.25 μM, and BE-333=3.7 μM.

Figure 14:
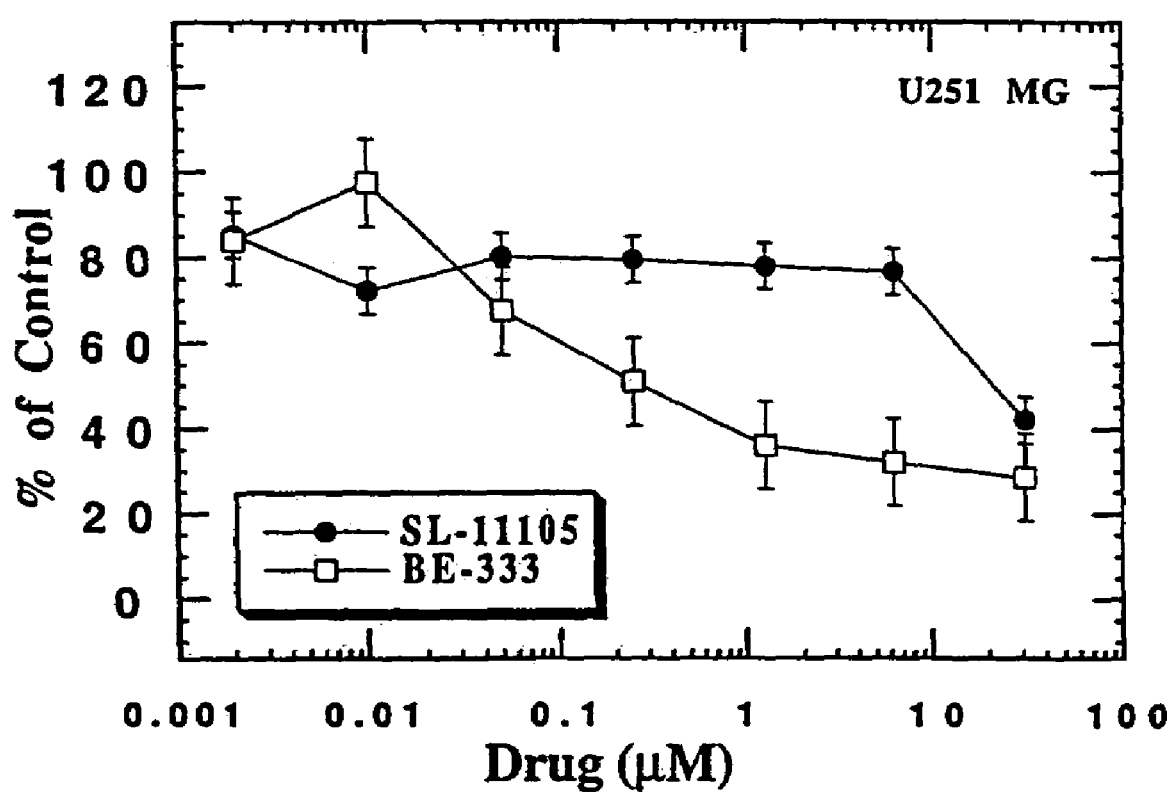

FIG. 14 is a graph depicting the in vitro effect of increasing concentrations of SL-11105 (●) and BE-333 (□) on the survival of cultured human brain tumor cells U251 MG NCI.

$ED_{50}$ of SL-11105=25.9 μM, and BE-333=0.23 μM.

Figure 15A:
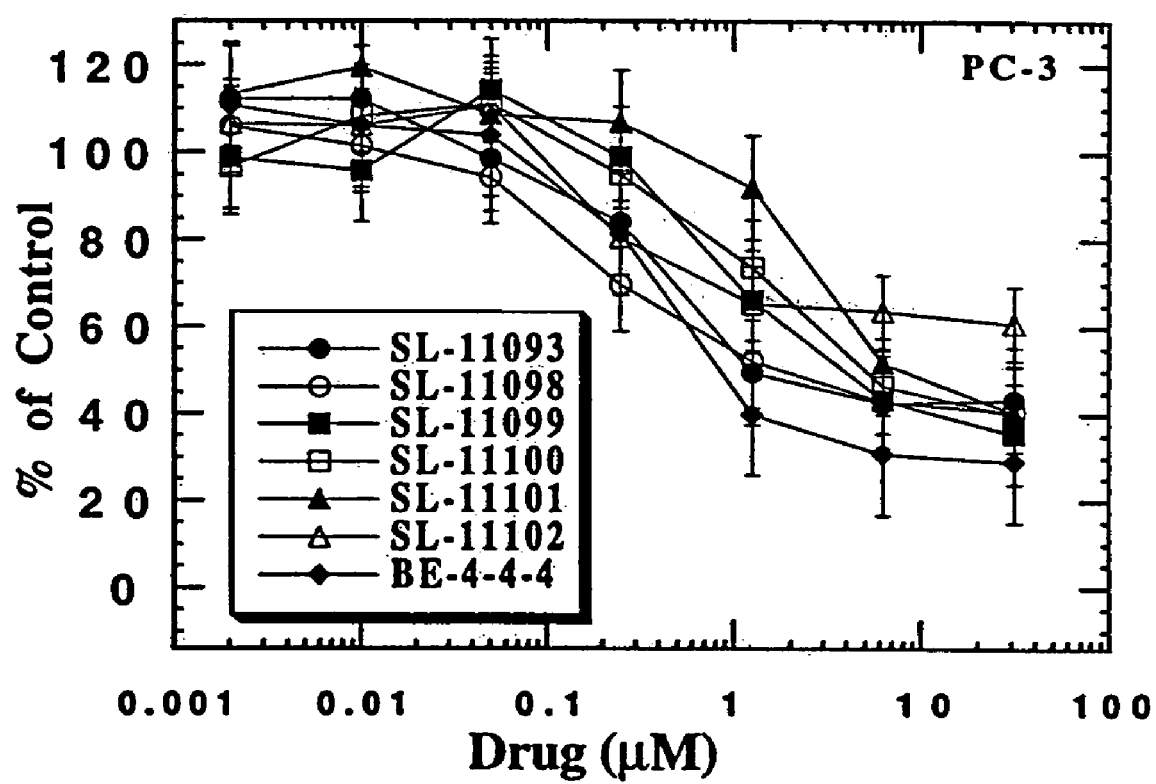

FIG. 15A is a graph depicting the in vitro effect of increasing concentrations of SL-11093 (●), SL-11098 (○), SL-11099 (■), SL-1100 (□), SL-11101 (▲), SL-11102 (Δ), and BE-444 (♦) on the survival of cultured human prostate cancer cells PC3.

$ED_{50}$ of SL-11093=1.6 μM, SL-11098=1.4 μM, SL-11099=2.5 μM, SL-11100=4.7 μM, SL-11101=7.7 μM, SL-11102>31.25 μM and BE-444=0.7 μM.

Figure 15B:
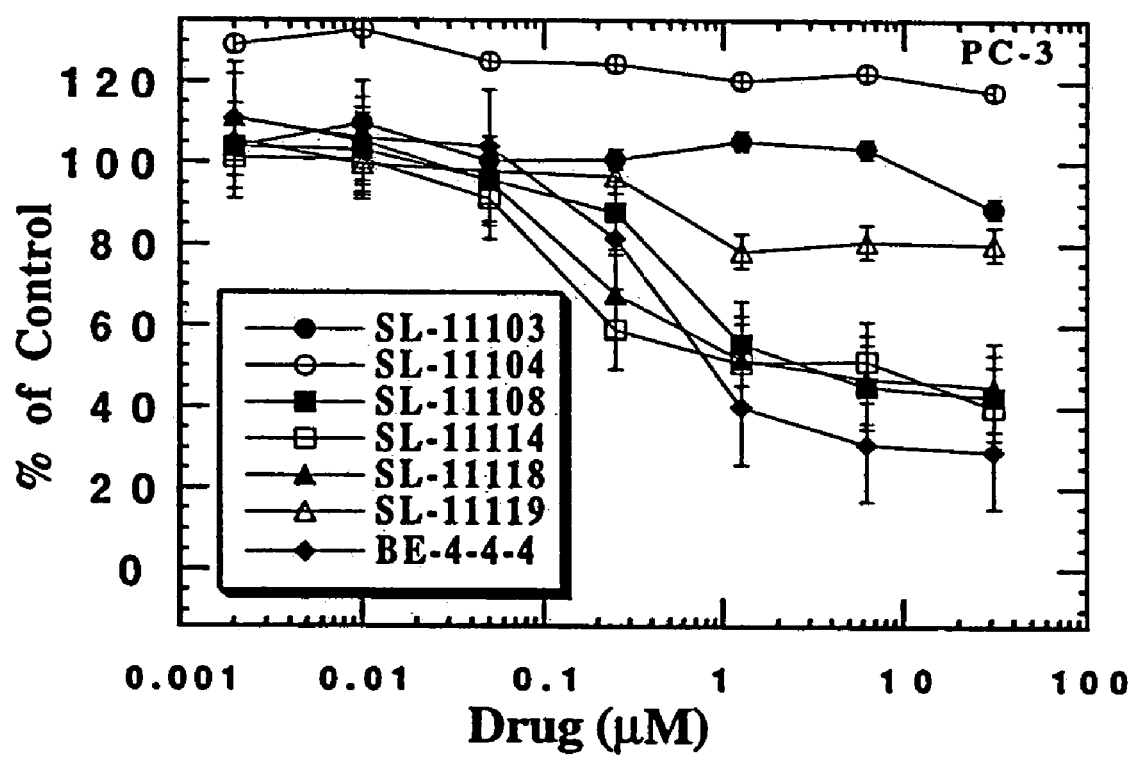

FIG. 15B is a graph depicting the in vitro effect of increasing concentrations of SL-11103 (●), SL-11104 (○), SL-11108 (■), SL-11114 (□), SL-11118 (▲), SL-11119 (Δ), and BE-444 (♦) on the survival of cultured human prostate cancer cells PC3.

Figure 16:
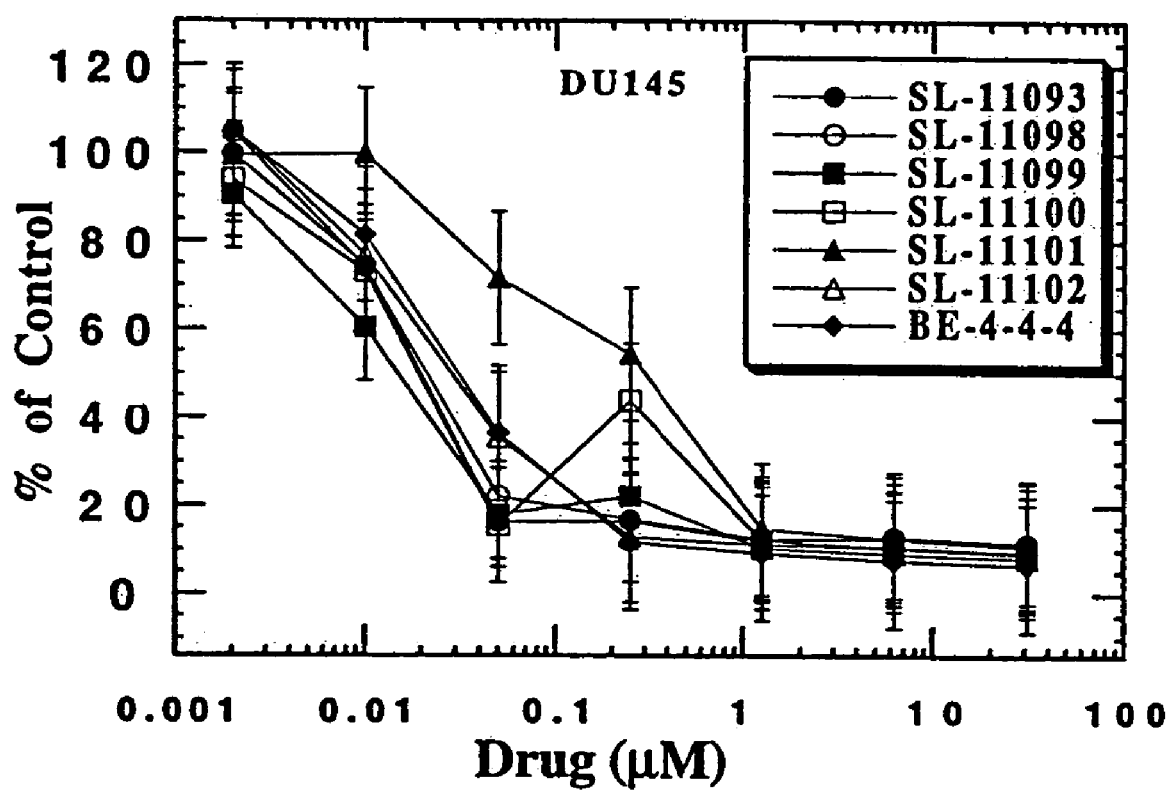
Figure 16:
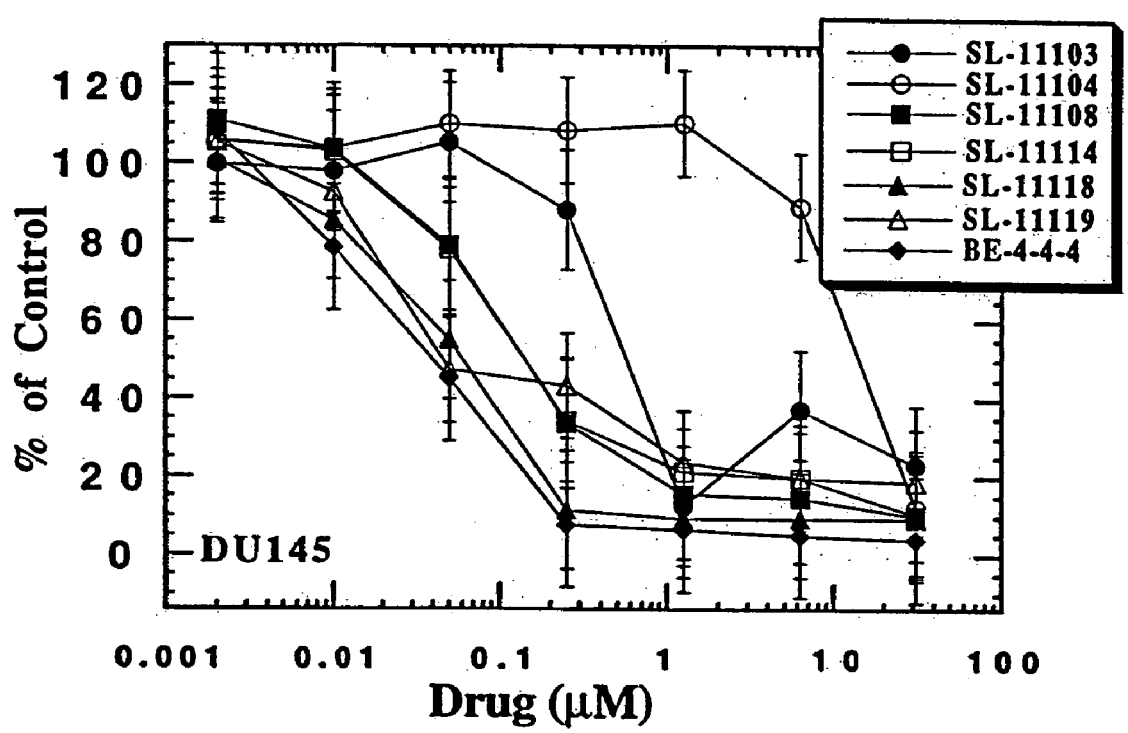

$ED_{50}$ of SL-11103>31.25 μM, SL-11104>31.25 μM, SL-11108=2.2 μM, SL-11114=0.7 μM, SL-11118=1.65 μM, SL-11119>31.25 μM and BE-444=0.7 μM FIG. 16A is a graph depicting the in vitro effect of increasing concentrations of SL-11093 (●), SL-11098 (○), SL-11099 (■), SL-11100 (□), SL-11101 (▲), SL-11102 (Δ), and BE-444 (♦) on the survival of cultured human prostate cancer cells DU145.

$ED_{50}$ of SL-11093=0.016 μM, SL-11098=0.02 μM, SL-11099=0.014 μM, SL-11100=0.021 μM, SL-11101=0.22 μM, SL-11102=0.03 μM and BE-444=0.03 μM.

FIG. 16B is a graph depicting the in vitro effect of increasing concentrations of SL-11103 (●), SL-11104 (○), SL-11108 (■), SL-11114 (□), SL-11118 (▲), SL-11119 (Δ), and BE-444 (♦) on the survival of cultured human prostate cancer cells DU145.

$ED_{50}$ of SL-11103=2.8 μM, SL-11104=9.4 μM, SL-11108=0.13 μM, SL-11114=0.13 μM, SL-11118=0.05 μM, SL-11119 0.08 μM and BE-444=0.03 μM.

Figure 17:
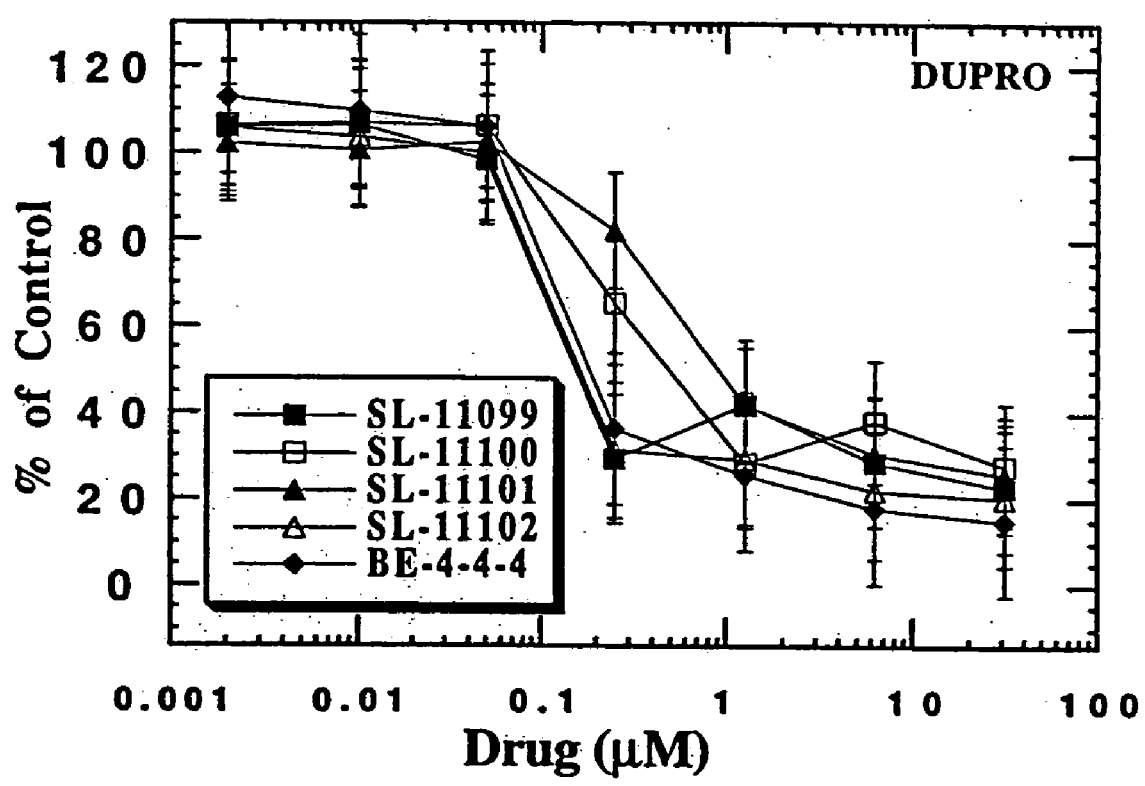
Figure 17:
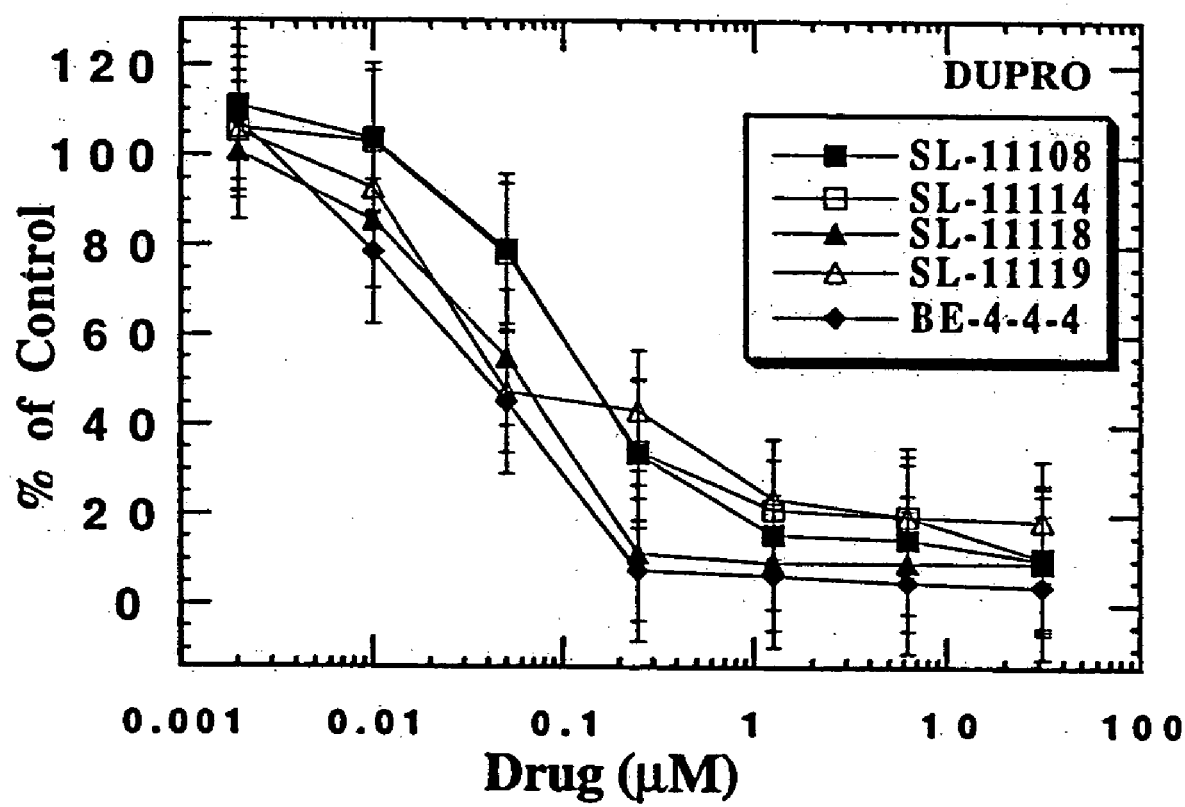

FIG. 17A is a graph depicting the in vitro effect of increasing concentrations of SL-11099 (■), SL-11100 (□), SL-11101 (▲), SL-11102 (Δ), and BE-444 (♦) on the survival of cultured human prostate cancer cells DUPRO.

$ED_{50}$ of =SL-11099=0.08 μM, SL-11100=0.3 μM, SL-11101=0.85 μM, SL-11102=0.15 μM and BE-444=0.2 μM.

FIG. 17B is a graph depicting the in vitro effect of increasing concentrations of SL-11108 (■), SL-11114 (□), SL-11118 (▲), SL-11119 (Δ), and BE-444 (♦) on the survival of cultured human prostate cancer cells DUPRO.

ED$_{50}$ of SL-11108=0.98 µM, SL-11114=0.64 µM, SL-11118=0.25 µM, SL-11119=0.44 µM and BE-444=0.2 µM.

Figure 18:
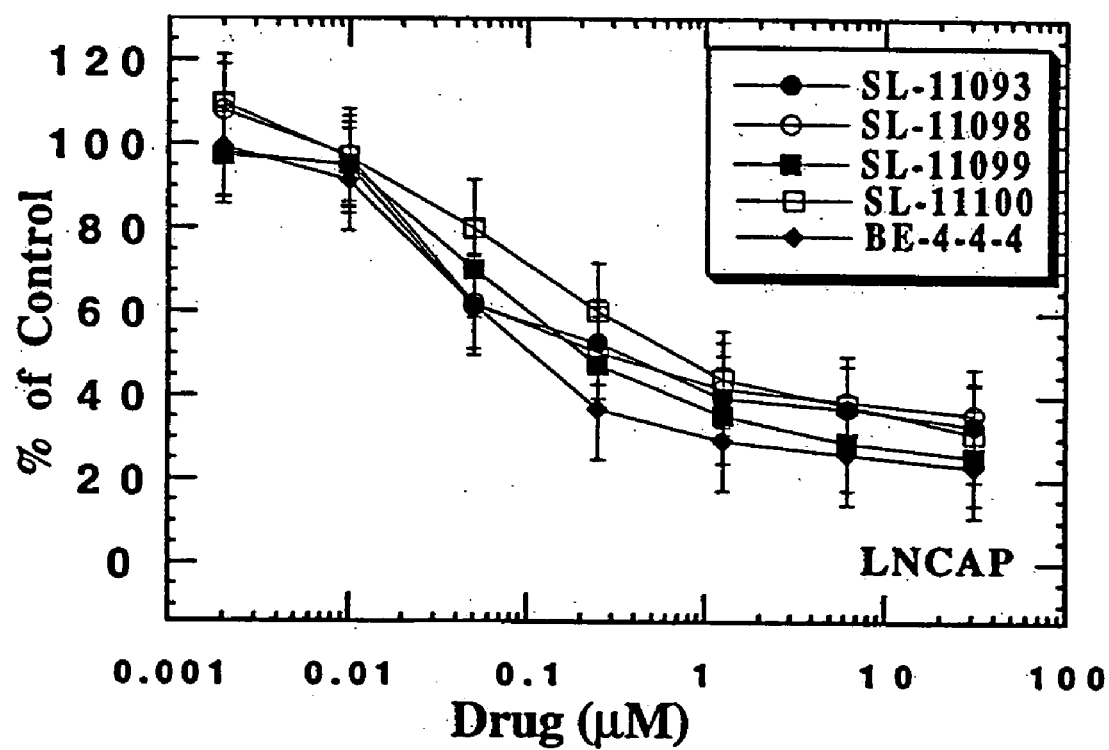
Figure 18:
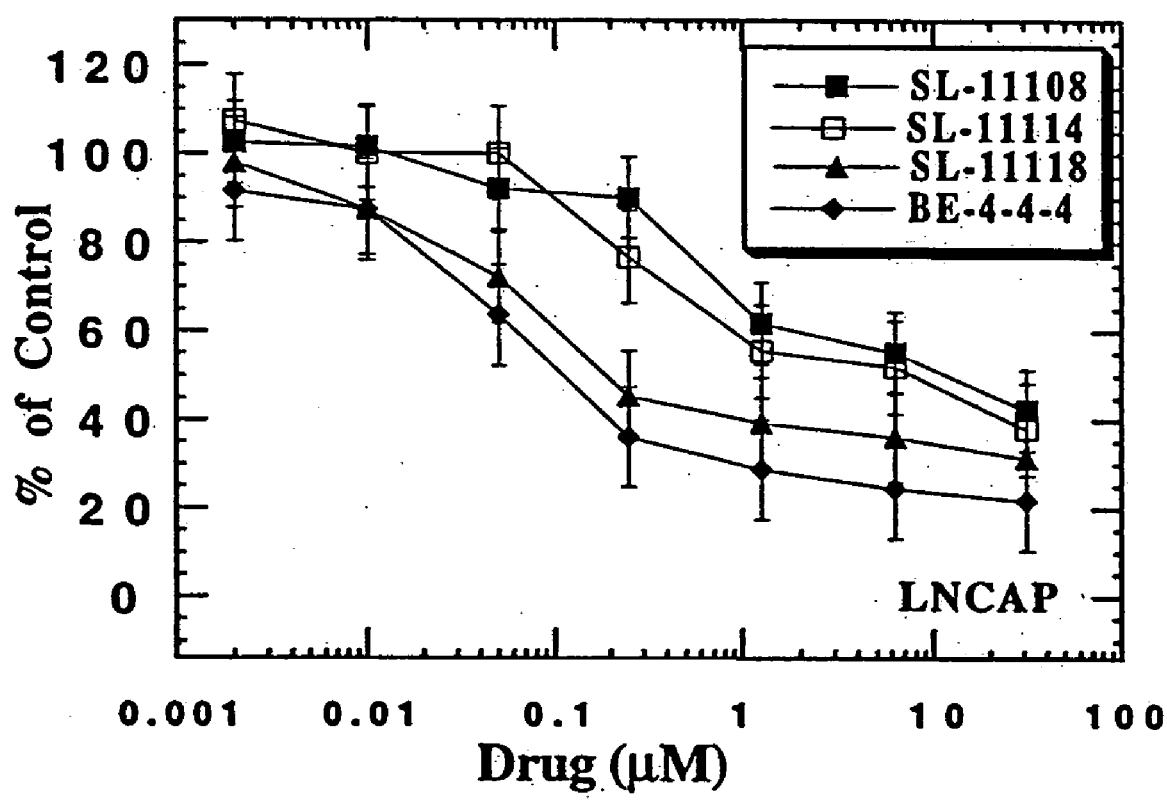

FIG. 18A is a graph depicting the in vitro effect of increasing concentrations of SL-11093 (●), SL-11098 (○), SL-11099 (■), SL-11100 (□), and BE-444 (♦) on the survival of cultured human prostate cancer cells LNCAP.

ED$_{50}$ of SL-11093=0.21 µM, SL-11098=0.17 µM, SL-11099=0.21 µM, SL-11100=0.7 µM, and BE-444=0.1 µM.

FIG. 18B is a graph depicting the in vitro effect of increasing concentrations of SL-11108 (■), SL-11114 (□), SL-11118 (▲), and BE-444 (♦) on the survival of cultured human prostate cancer cells LNCAP.

ED$_{50}$ of SL-11108=7.7 µM, SL-11114=3.0 µM, SL-11118=0.21 µM, and BE-444=0.1 µM.

Figure 19A:
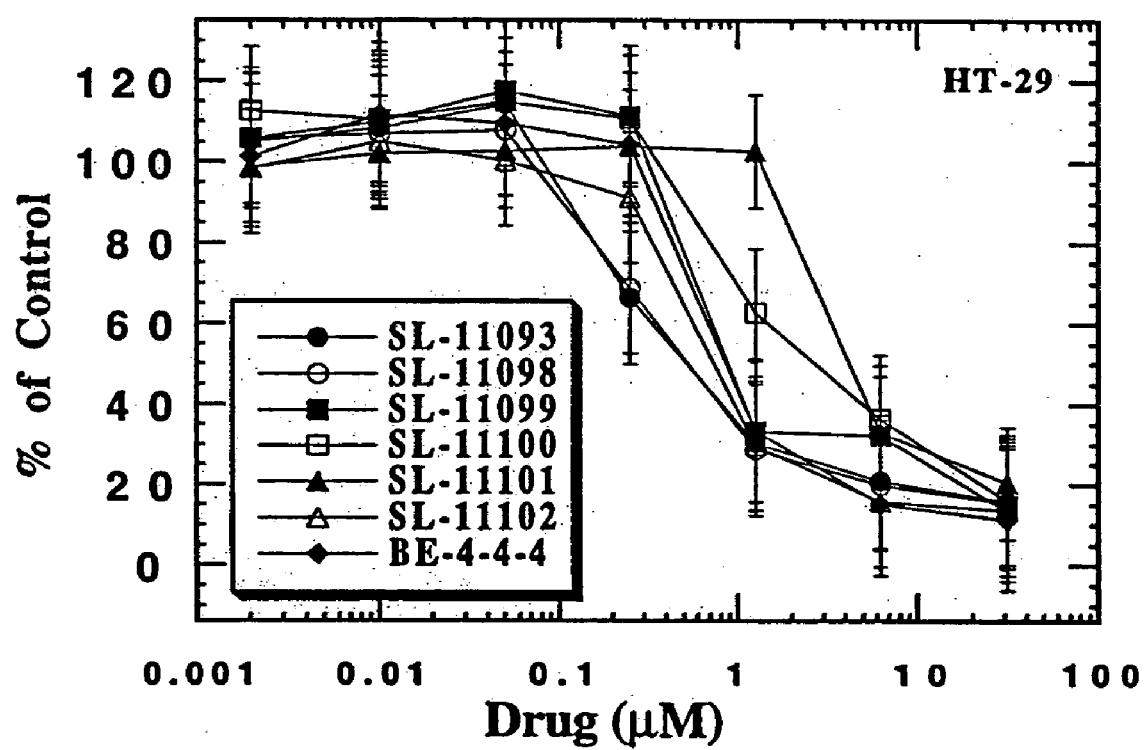

FIG. 19A is a graph depicting the in vitro effect of increasing concentrations of SL-11093 (●), SL-11098 (○), SL-11099 (■), SL-11100 (□), SL-11101 (▲), SL-11102 (Δ), and BE-444 (♦) on the survival of cultured human colon cancer cells HT29.

ED$_{50}$ of SL-11093=0.4 µM, SL-11098=0.4 µM, SL-11099=1.0 µM, SL-11100=2.0 µM, SL-11101=5.2 µM. SL-11102=0.73 µM and BE-444=0.93 µM.

Figure 19B:
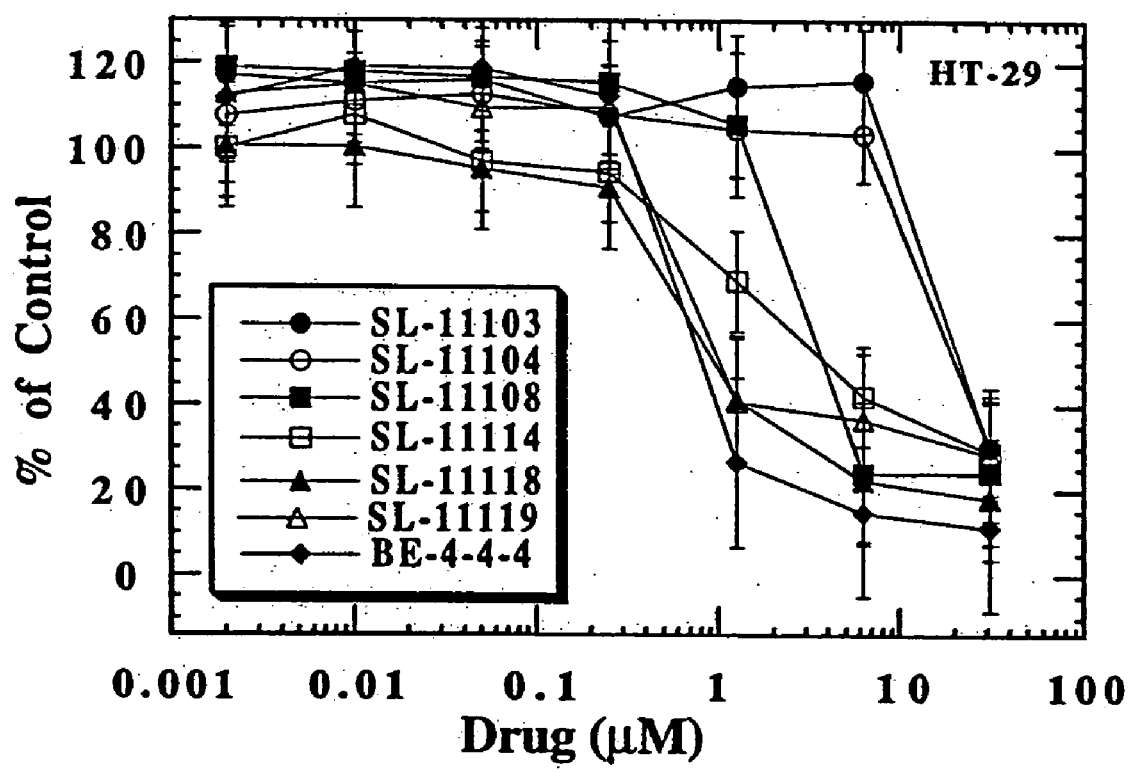

FIG. 19B is a graph depicting the in vitro effect of increasing concentrations of SL-11103 (●), SL-11104 (○), SL-11108 (■), SL-11114 (□), SL-11118 (▲), SL-11119 (Δ), and BE-444 (♦) on the survival of cultured human colon cancer cells HT29.

ED$_{50}$ of SL-11103=29.4 µM, SL-11104=25.8 µM, SL-11108=2.0 µM, SL-11114=3.6 µM, SL-11118=0.98 µM, SL-11119=0.97 µM and BE-444=0.93 µM.

Figure 20:
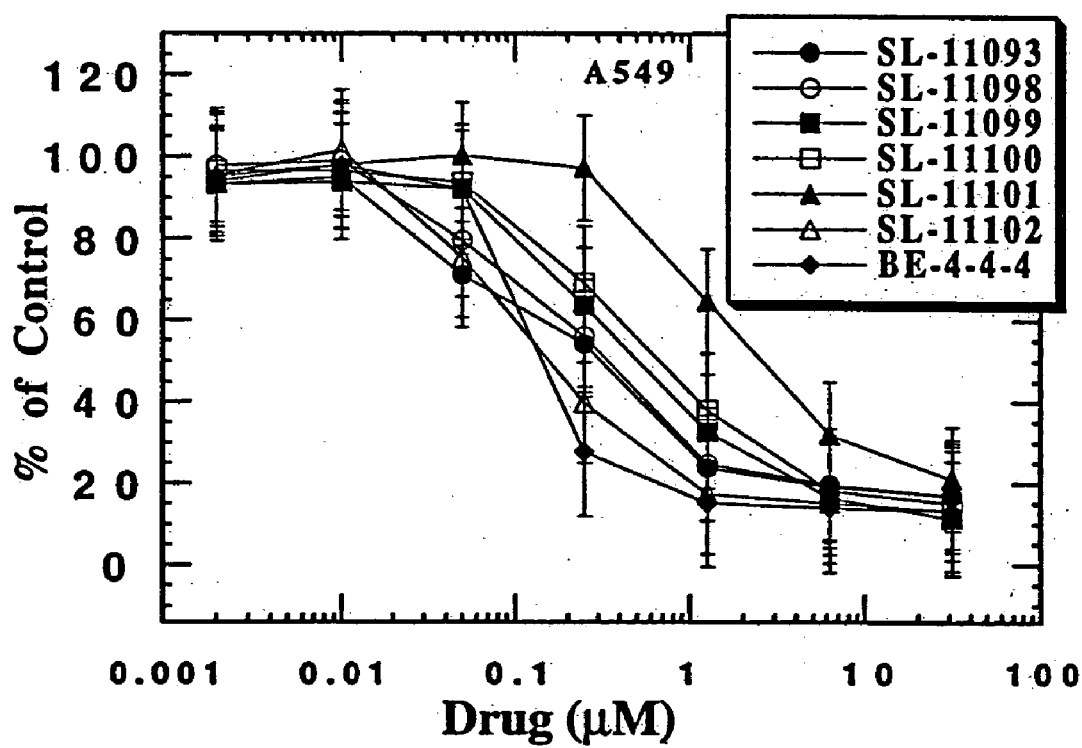
Figure 20:
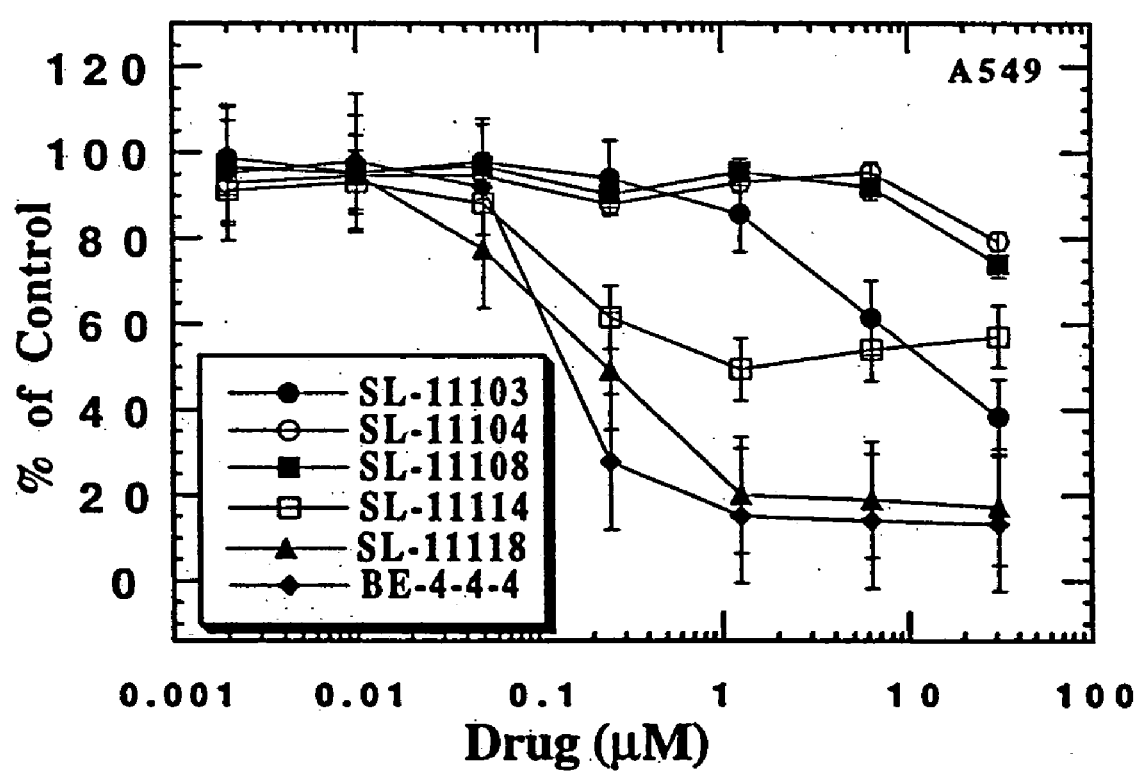

FIG. 20A is a graph depicting the in vitro effect of increasing concentrations of SL-11093 (●), SL-11098 (○), SL-11099 (■), SL-11100 (□), SL-11101 (▲), SL-11102 (Δ), and BE-444 (♦) on the survival of cultured human lung cancer cells A549.

ED$_{50}$ of SL-11093=0.26 µM, SL-11098=0.29 µM, SL-11099=0.51 µM, SL-11100=0.65 µM, SL-11101=2.2 µM, SL-11102=0.15 µM and BE-444=0.15 µM.

FIG. 20B is a graph depicting the in vitro effect of increasing concentrations of SL-11103 (●), SL-11104 (○), SL-11108 (■), SL-11114 (□), SL-11118 (▲), and BE-444 (♦) on the survival of cultured human lung cancer cells A549.

ED$_{50}$ of SL-11103=12.4 µM, SL-11104>31.25 µM, SL-11108>31.25 µM, SL-11114>31.25 µM, SL-11118=0.214 µM and BE-444=0.15 µM.

Figure 21:
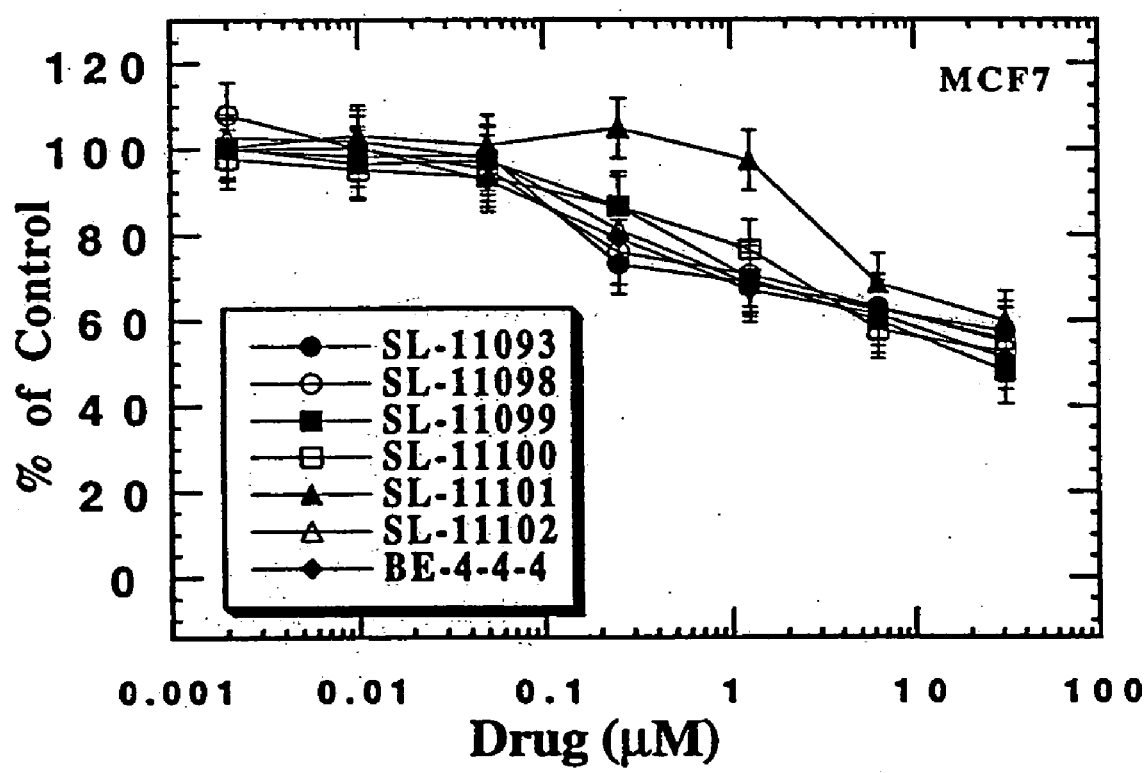
Figure 21:
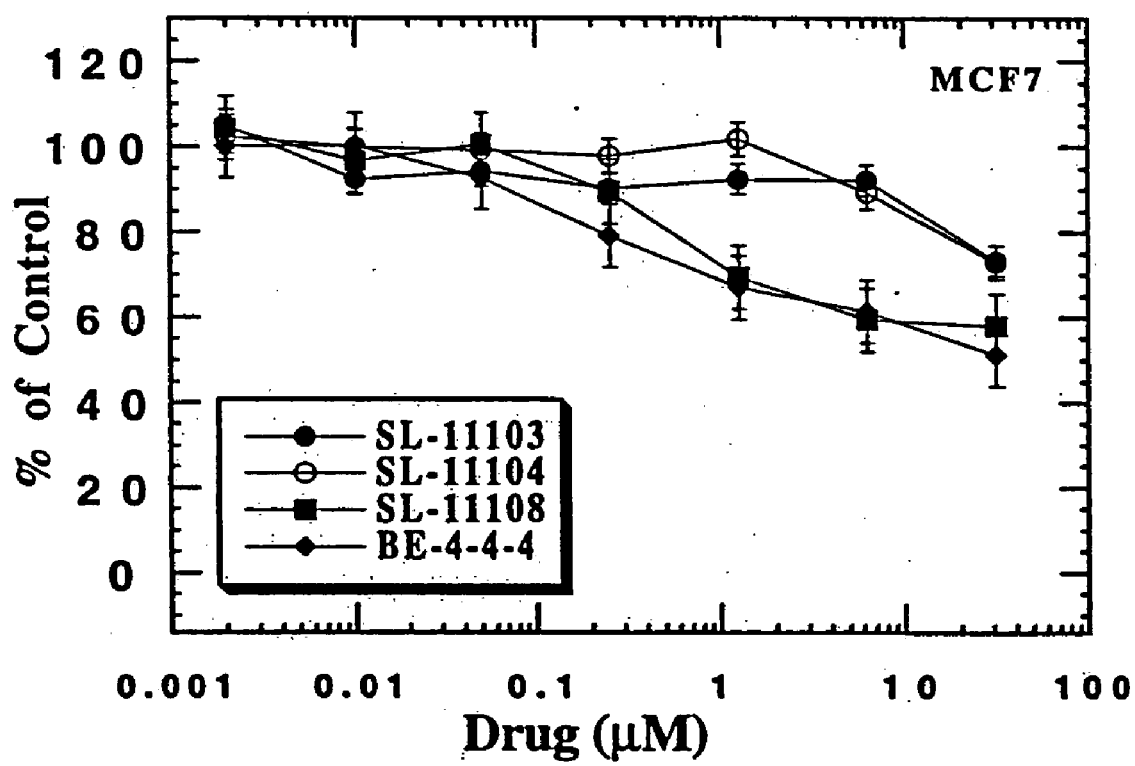

FIG. 21A is a graph depicting the in vitro effect of increasing concentrations of SL-11093 (●), SL-11098 (○), SL-11099 (■), SL-11100 (□), SL-11 101 (▲), SL-11102 (Δ), and BE-444 (♦) on the survival of cultured human breast cancer cells MCF7.

ED$_{50}$ of SL-11093=0.66 µM, SL-11098>31.25 µM, SL-11099=26.3 µM, SL-11100>31.25 µM, SL-11101>31.25 µM SL-11102>31.25 µM and BE-444>31.25 µM.

FIG. 21B is a graph depicting the in vitro effect of increasing concentrations of SL-11103 (●), SL-11104 (○), SL-11108 (■), and BE-444 (♦) on the survival of cultured human breast cancer cells MCF7.

ED$_{50}$ of SL-11103>31.25 µM, SL-11104>31.25 µM, SL-11108>31.25 µM, and BE-444>31.25 µM.

Figure 22:
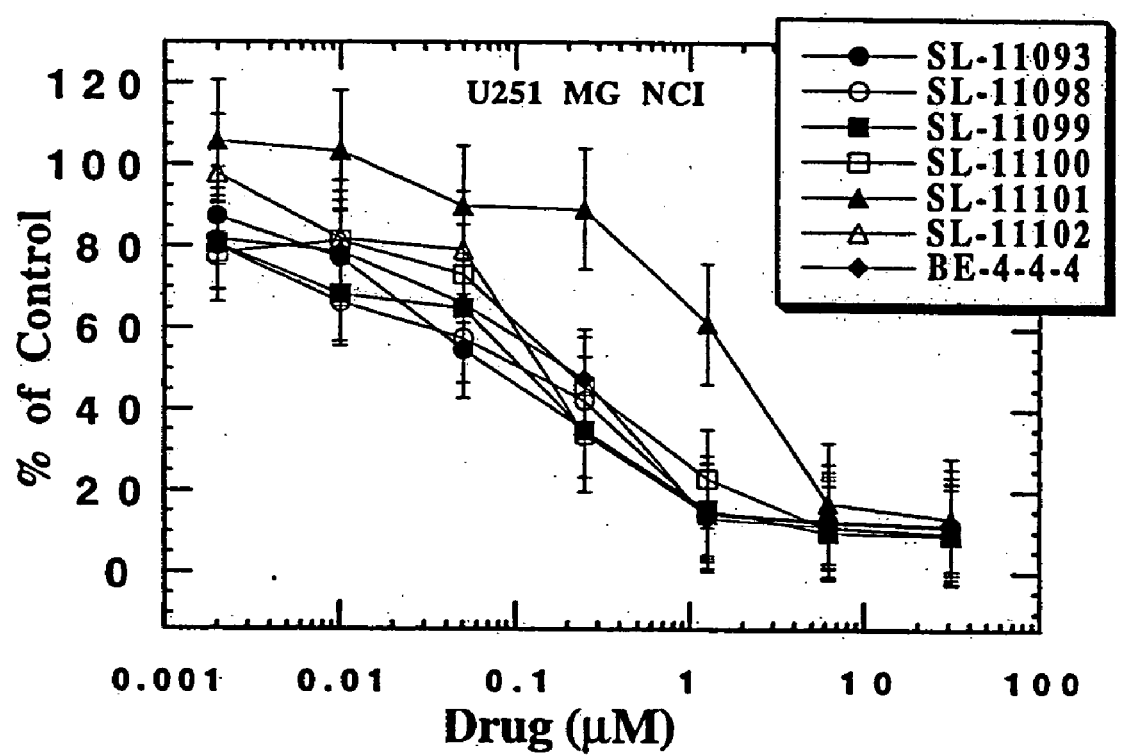
Figure 22:
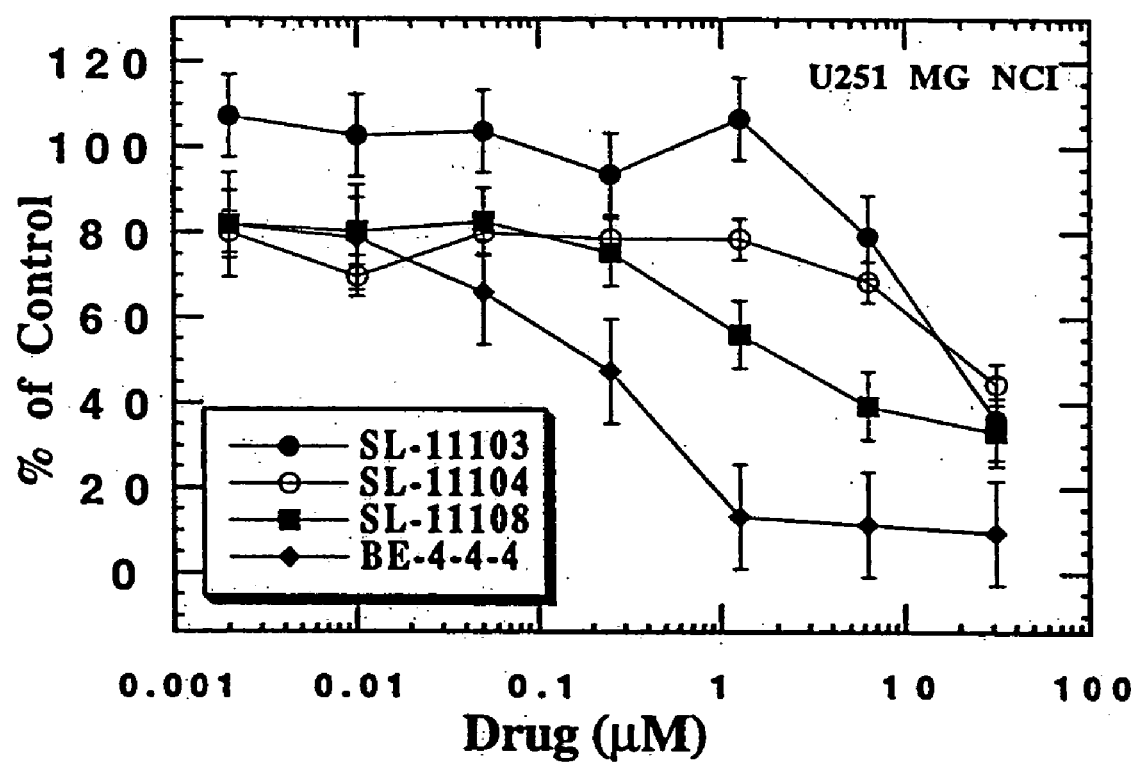

FIG. 22A is a graph depicting the in vitro effect of increasing concentrations of SL-11093 (●), SL-11098 (○), SL-11099 (■), SL-11100 (□), SL-11101 (▲), SL-11102 (Δ), and BE-444 (♦) on the survival of cultured human brain tumor cells U251 MG NCI.

ED$_{50}$ of SL-11093=0.07 µM, SL-11098=0.1 µM, SL-11099=0.11 µM, SL-11100=0.22 µM, SL-11101=1.7 µM, SL-11102=0.15 µM and BE-444=0.2 µM.

FIG. 22B is a graph depicting the in vitro effect of increasing concentrations of SL-11103 (●), SL-11104 (○), SL-11108 (■), and BE-444 (♦) on the survival of cultured human brain tumor cells U251 MG NCI.

ED$_{50}$ of SL-11103=9.5 µM, SL-11104=14.71 µM, SL-11108=2.0 µM, and BE-444=0.2 µM.

Figure 23:
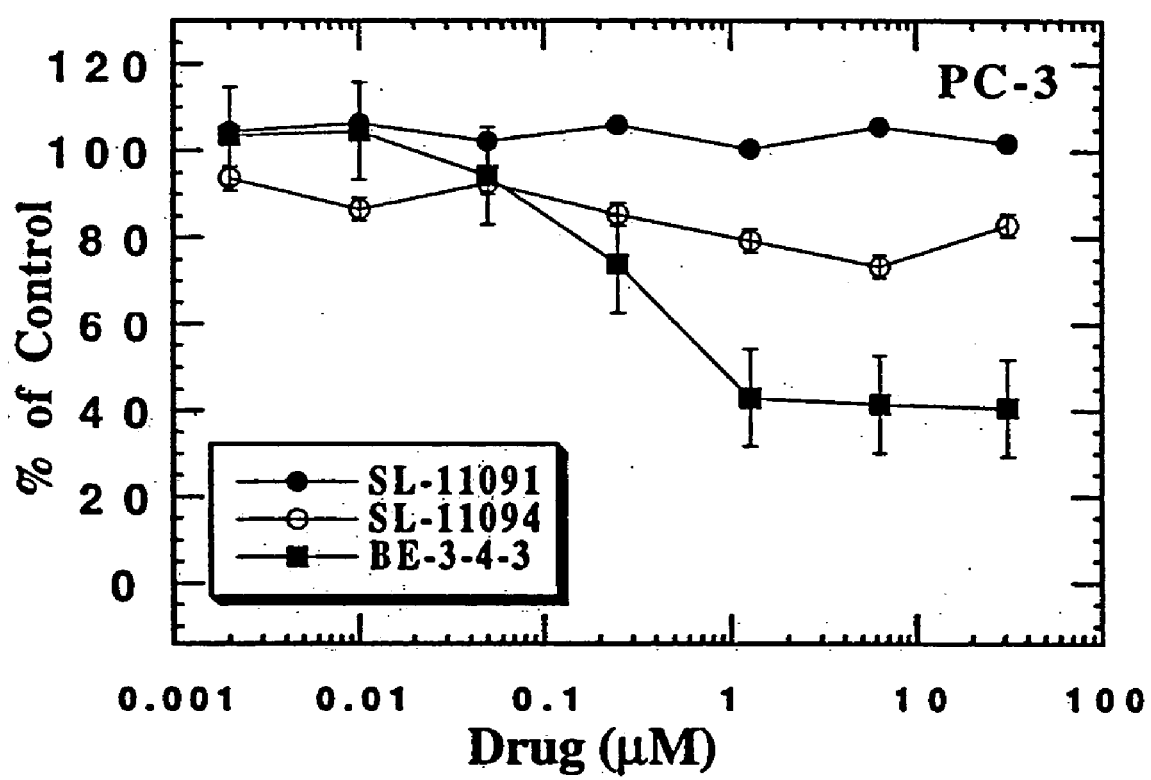

FIG. 23 is a graph depicting the in vitro effect of increasing concentrations of SL-11091 (●), SL-11094 (○), and BE-343 (■) on the survival of cultured human prostate cancer cells PC3.

ED$_{50}$ of SL-11091>31.25 µM, SL-11094>31.25 µM, and BE-343=0.24 µM.

Figure 24:
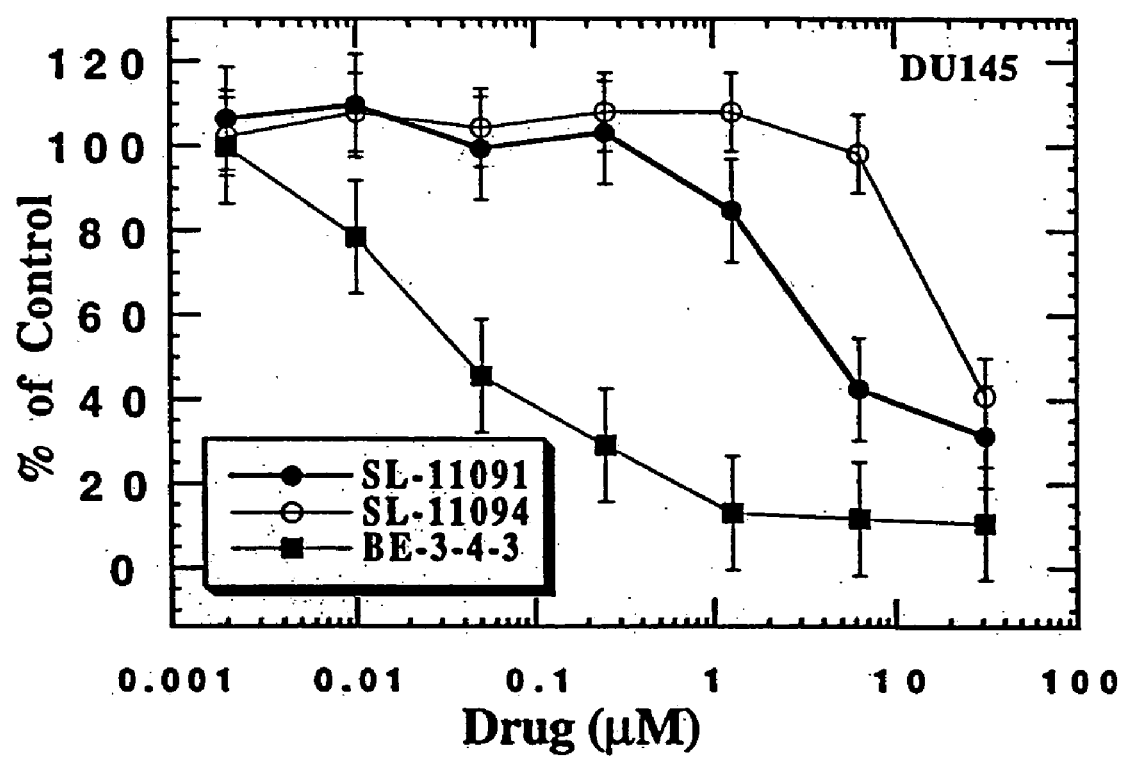

FIG. 24 is a graph depicting the in vitro effect of increasing concentrations of SL-11091 (●), SL-11094 (○), and BE-343 (■) on the survival of cultured human prostate cancer cells DU145.

ED$_{50}$ of SL-11091=4.33 µM, SL-11094=15.4 µM, and BE-343=0.044 µM.

Figure 25:
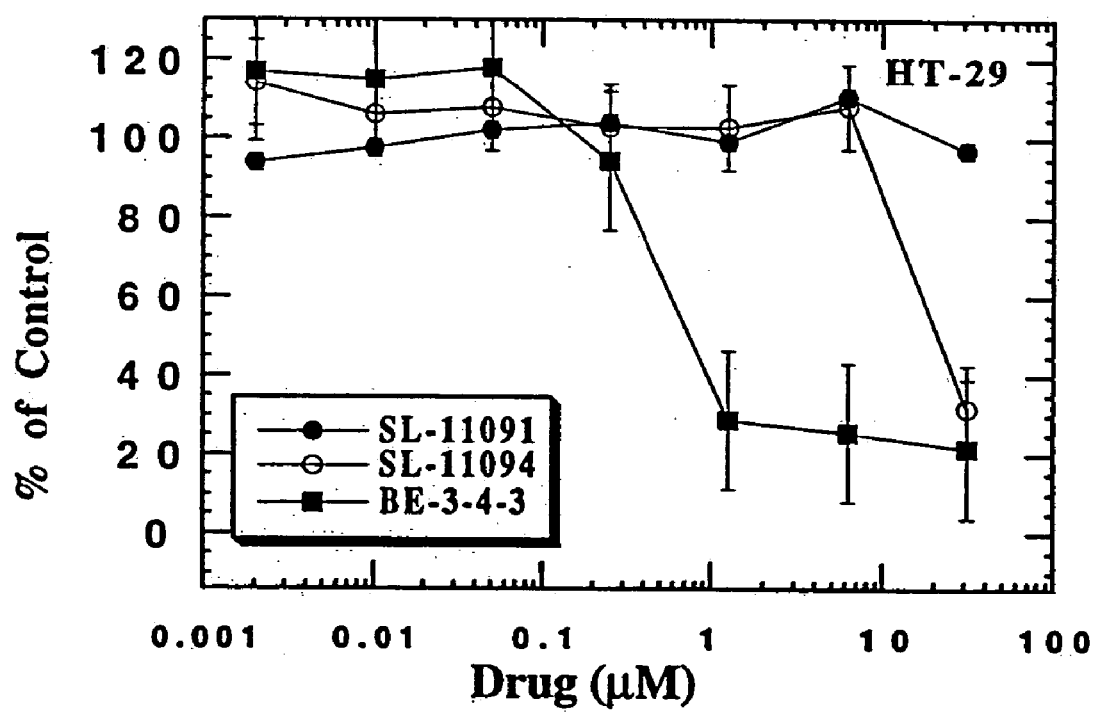

FIG. 25 is a graph depicting the in vitro effect of increasing concentrations of SL-11091 (●), SL-11094 (○), and BE-343 (■) on the survival of cultured human colon cancer cells HT29.

ED$_{50}$ of SL-11091>31.25 µM, SL-11094=28.8 µM, and BE-343=0.6 µM.

Figure 26:
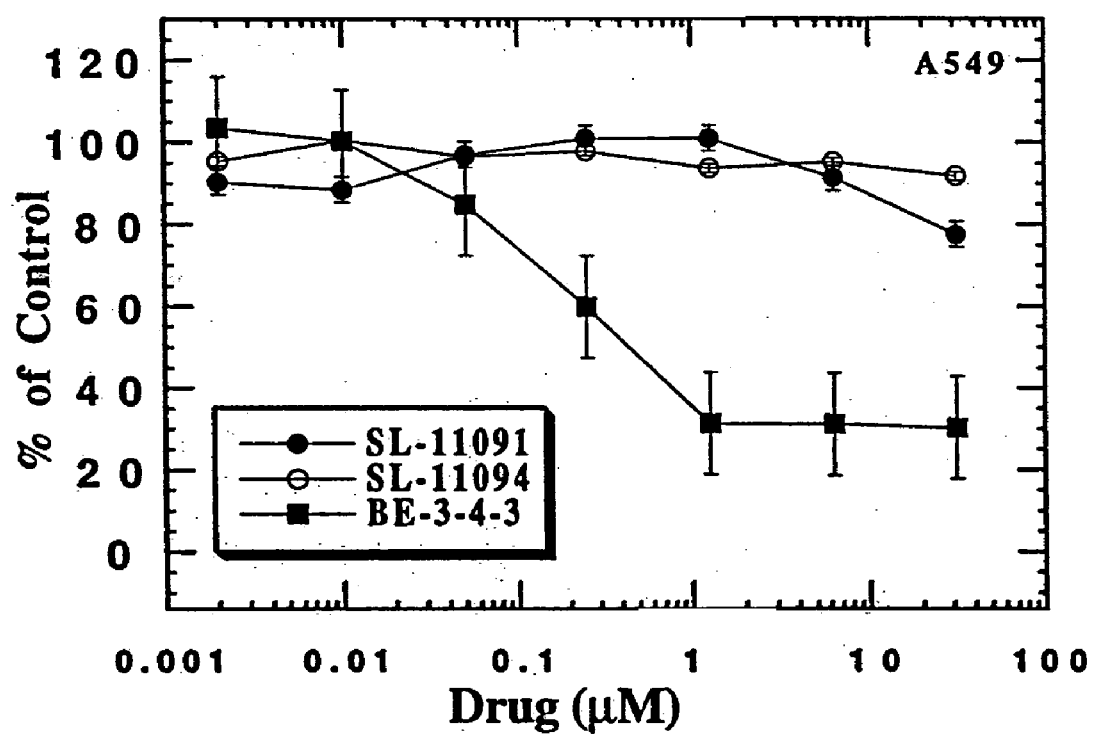

FIG. 26 is a graph depicting the in vitro effect of increasing concentrations of SL-11091 (●), SL-11094 (○), and BE-343 (■) on the survival of cultured human lung cancer cells A549.

ED$_{50}$ of SL-11091>31.25 µM, SL-11094>31.25 µM, and BE-343=0.2 µM.

Figure 27:
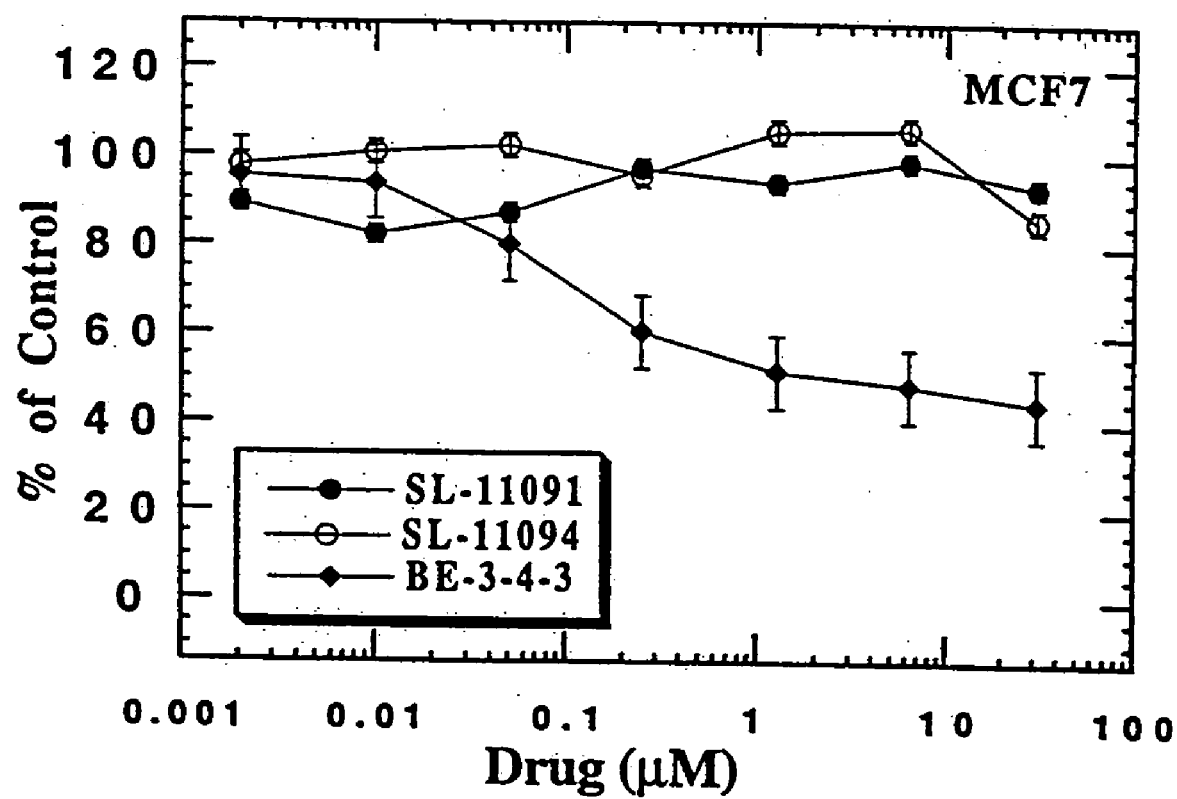

FIG. 27 is a graph depicting the in vitro effect of increasing concentrations of SL-11091 (●), SL-11094 (○), and BE-343 (♦) on the survival of cultured human breast cancer cells MCF7.

ED$_{50}$ of SL-11091>31.25 µM, SL-11094>31.25 µM, and BE-343=0.5 µM.

Figure 28:
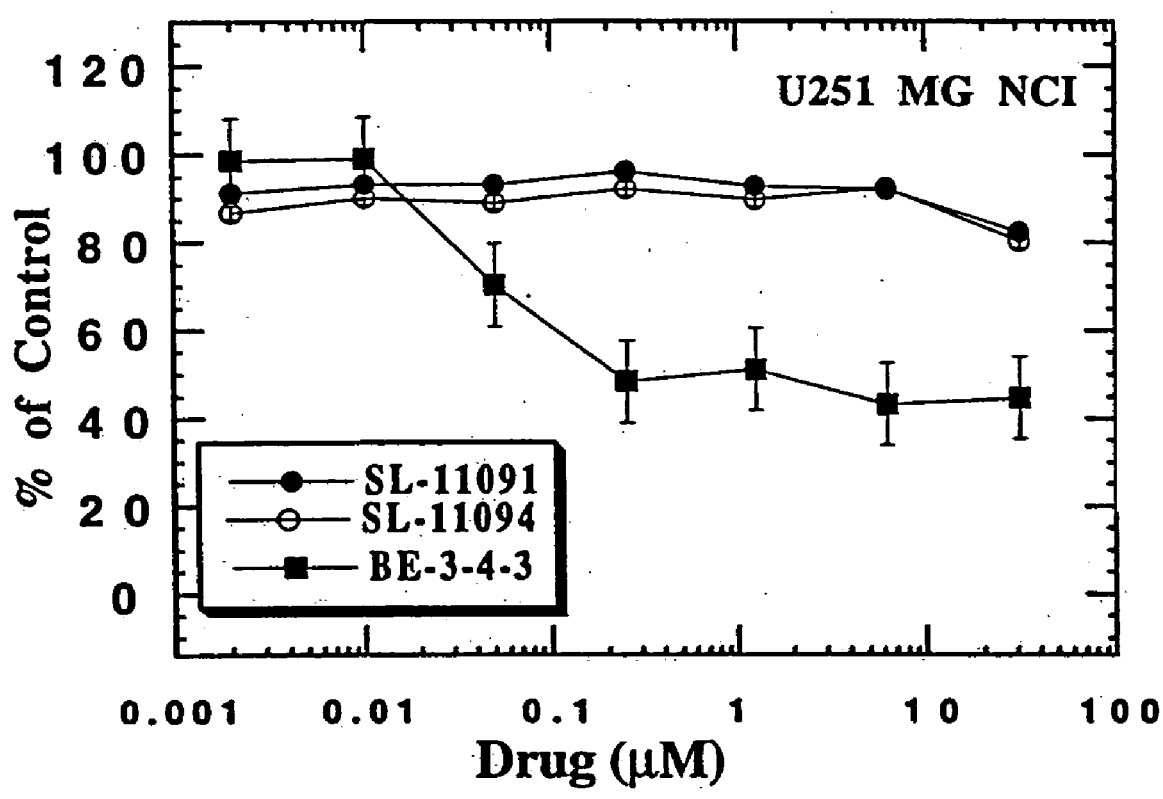

FIG. 28 is a graph depicting the in vitro effect of increasing concentrations of SL-11091(●), SL-11094 (○), and BE-343 (■) on the survival of cultured human brain tumor cells U251 MG NCI.

ED$_{50}$ of SL-11091>31.25 µM, SL-11094>31.25 µM, and BE-343=0.14 µM.

Figure 29:
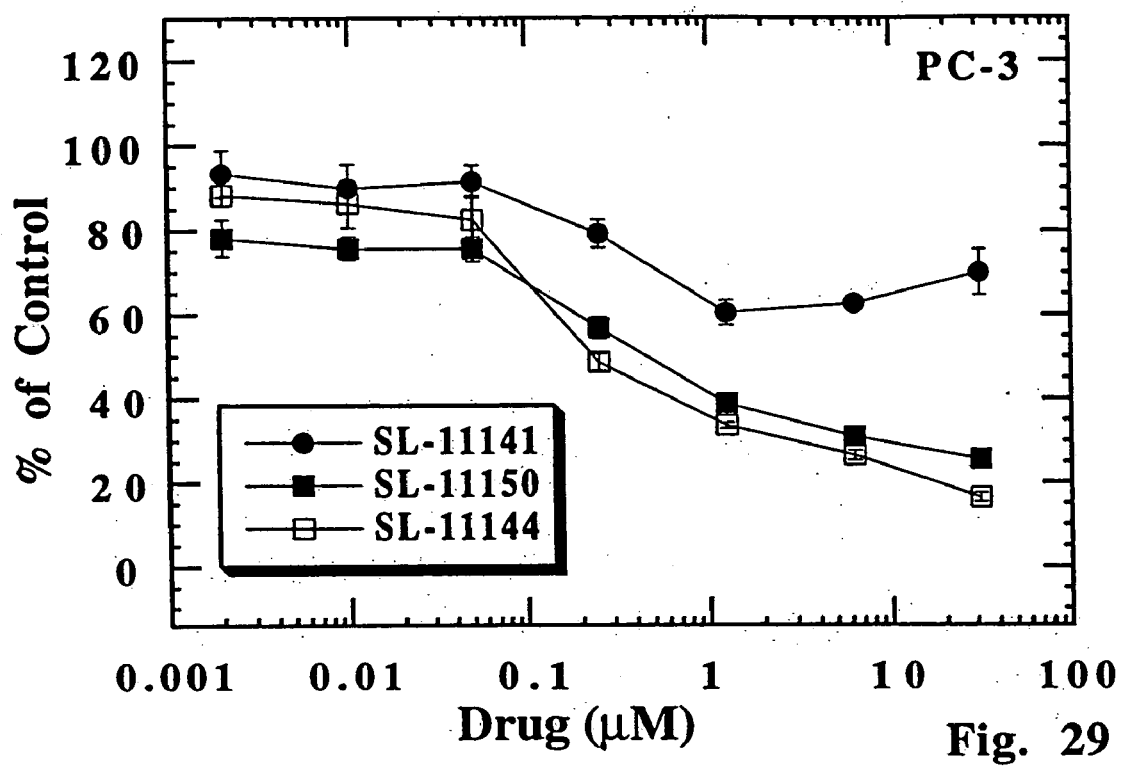

FIG. 29 is a graph depicting the in vitro effect of increasing concentrations of SL-11141(●), SL-11144 (□), SL-11150 (■) on the survival of cultured human prostate cancer cells PC3.

ED$_{50}$ of SL-11141>31.25 µM, SL-11144=0.3 µM, and SL-11150=0.5 µM.

Figure 30:
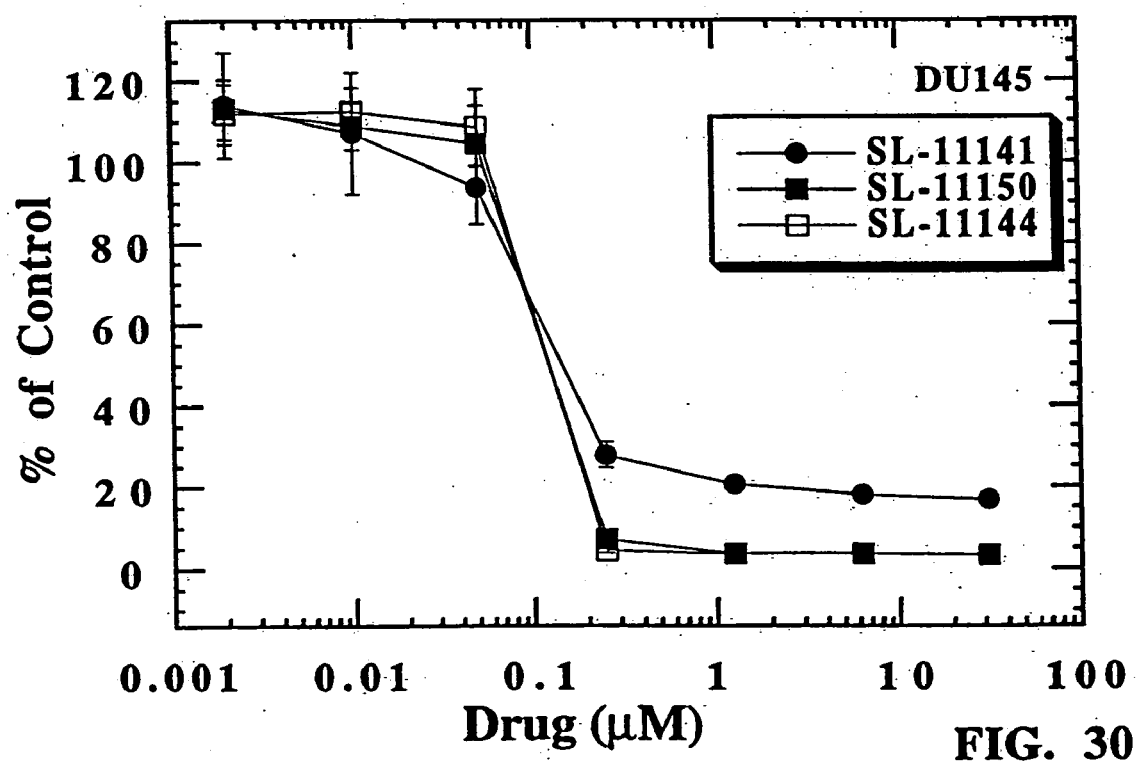

FIG. 30 is a graph depicting the in vitro effect of increasing concentrations of SL-11141 (●), SL-111144 (□), SL-11150 (■) on the survival of cultured human prostate cancer cells DU145.

ED$_{50}$ of SL-11141=0.13 µM, SL-11144=0.1 µM, and SL-11150=0.11 µM.

Figure 31:
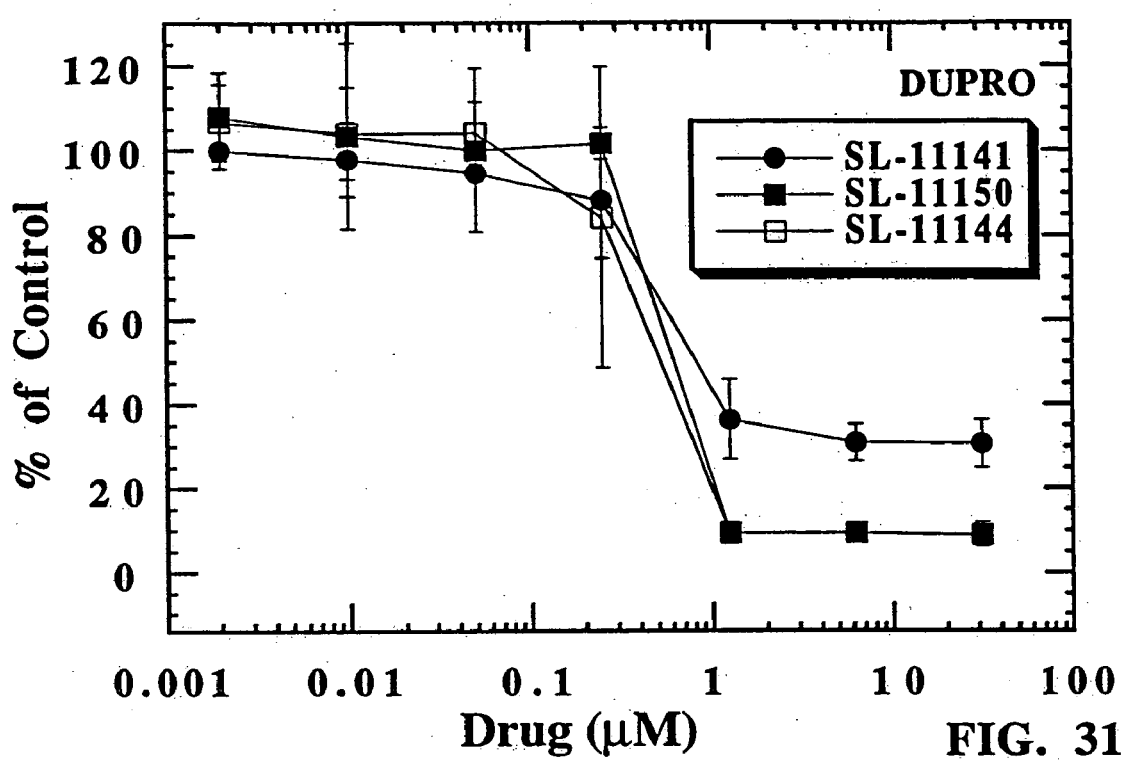

FIG. 31 is a graph depicting the in vitro effect of increasing concentrations of SL-11141 (●), SL-11144 (□), SL-11150 (■) on the survival of cultured human prostate cancer cells DUPRO.

ED$_{50}$ of SL-11141=0.71 µM, SL-11144=0.36 µM, and SL-11150=0.48 µM.

Figure 32:
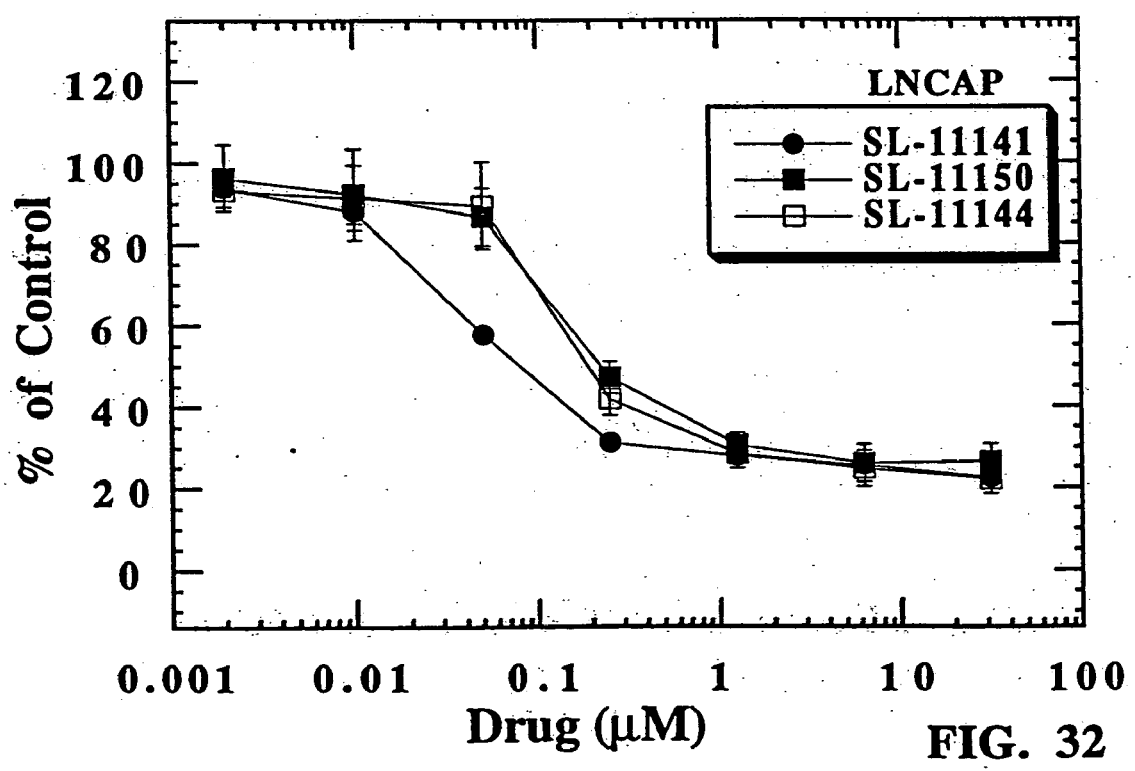

FIG. 32 is a graph depicting the in vitro effect of increasing concentrations of SL-11141 (●), SL-11144 (□), SL-11150 (■) on the survival of cultured human prostate cancer cells LNCAP.
$ED_{50}$ of SL-11141=0.07 µM, SL-11144=0.20 µM, and SL-11150=0.23 µM.

Figure 33:
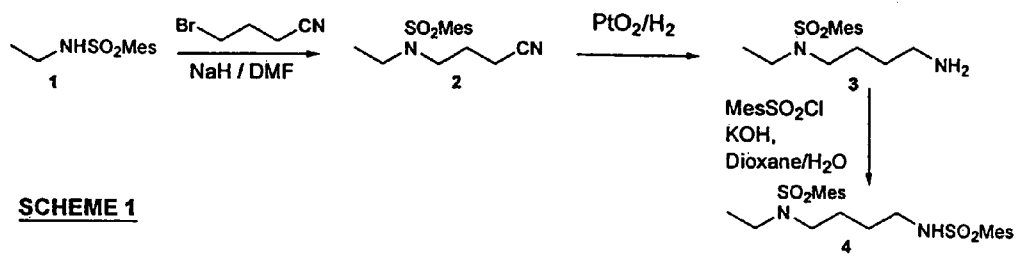
Figure 33:
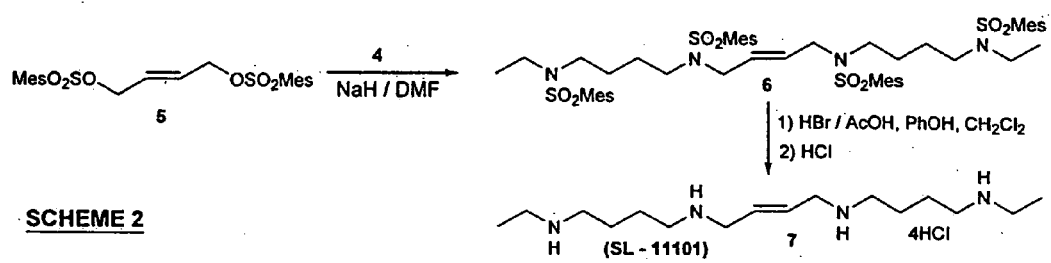
Figure 33:
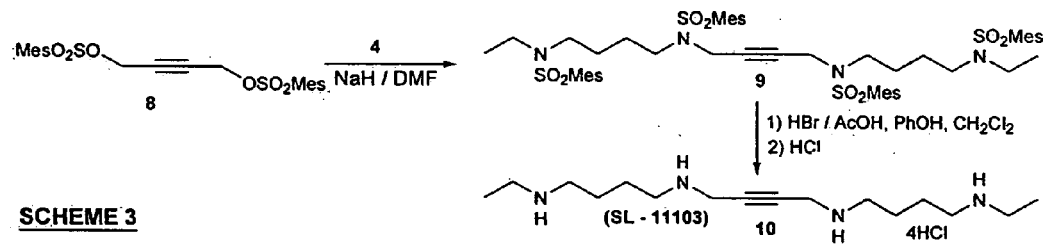
Figure 33:
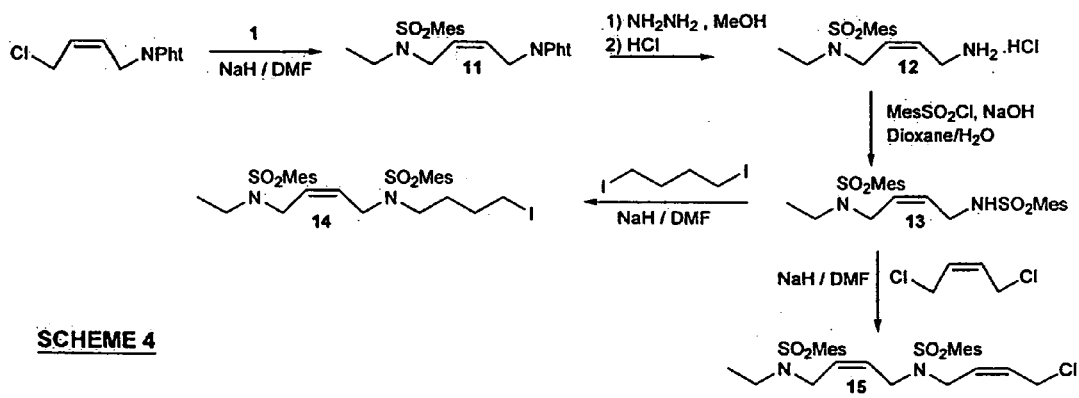

FIG. 33 illustrates synthetic methodology used to prepare the compounds of the invention.

Figure 34:
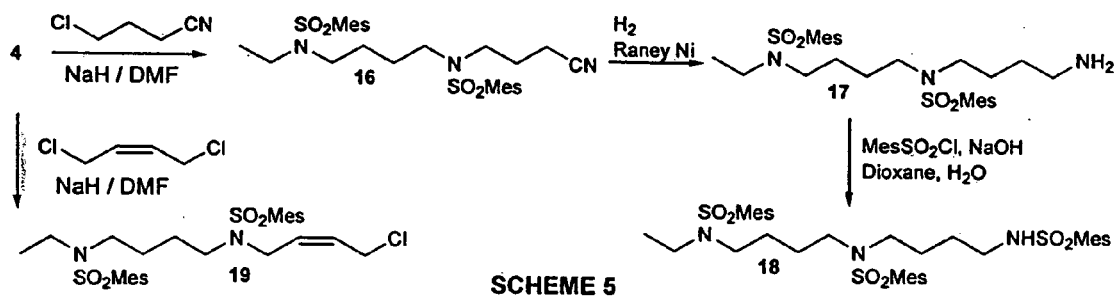
Figure 34:
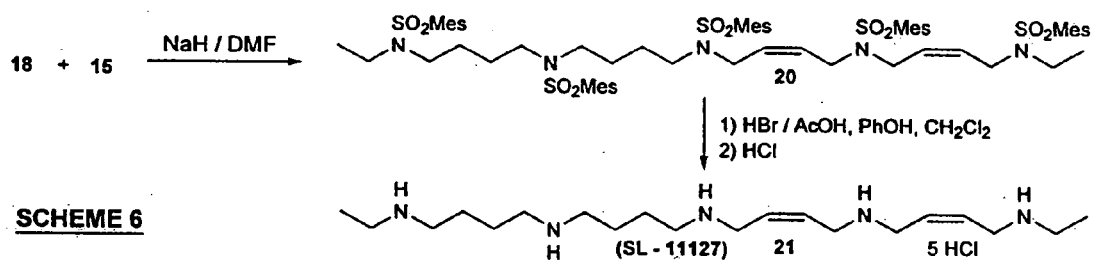
Figure 34:
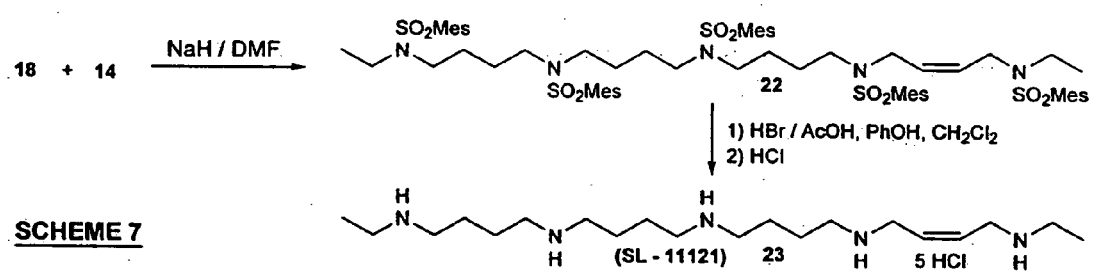
Figure 34:
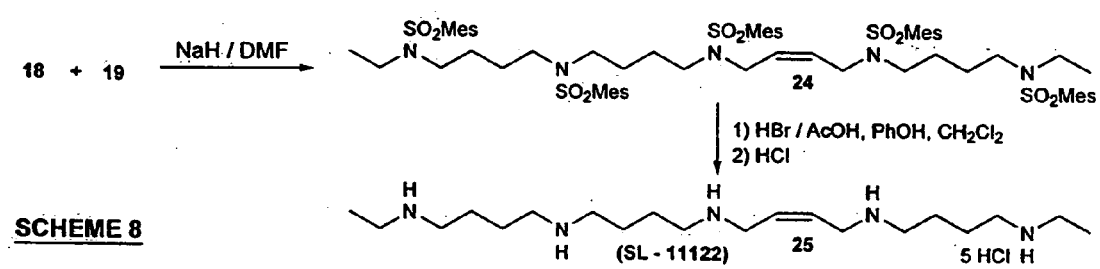
Figure 34:
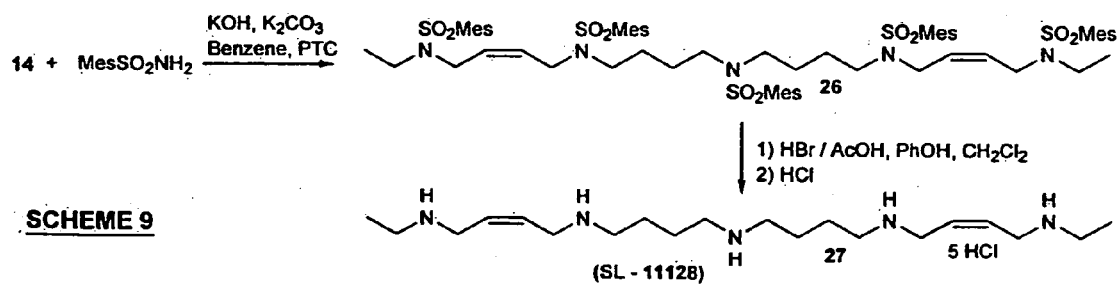

FIG. 34 illustrates additional synthetic methodology used to prepare the compounds of the invention.

Figure 35:
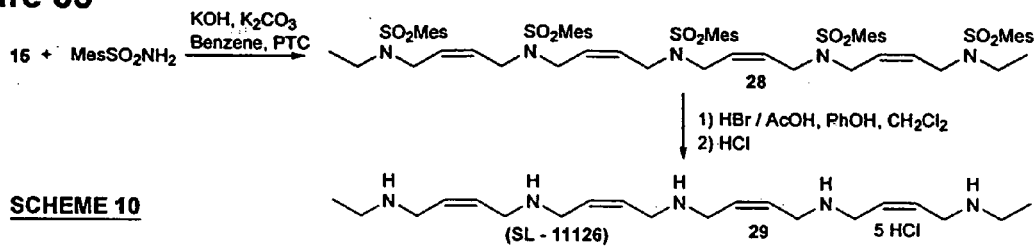
Figure 35:
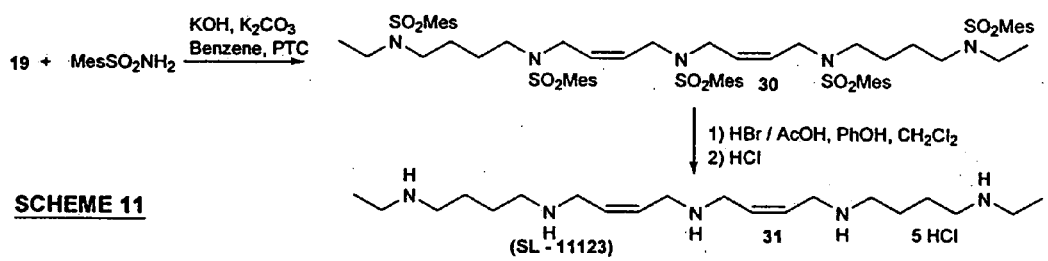
Figure 35:
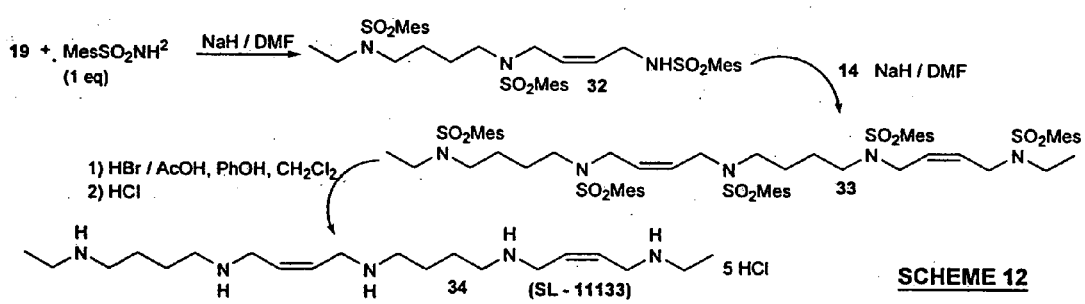
Figure 35:
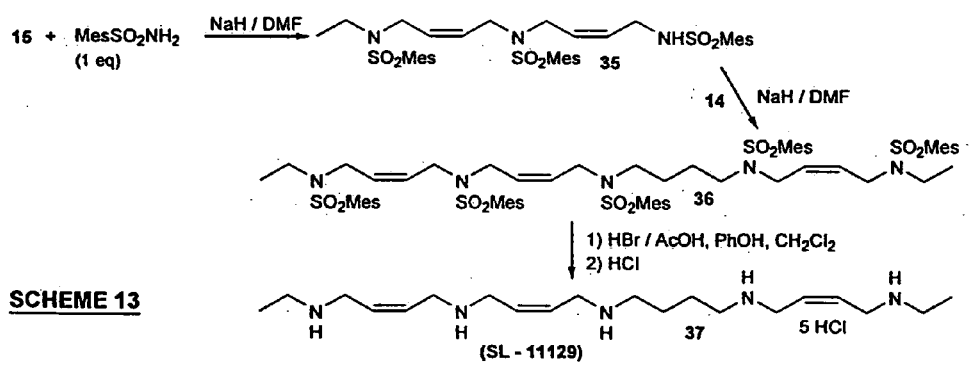
Figure 35:
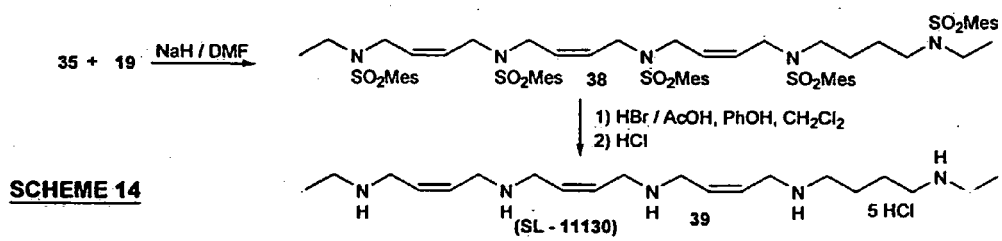

FIG. 35 illustrates additional synthetic methodology used to prepare the compounds of the invention.

Figure 36:
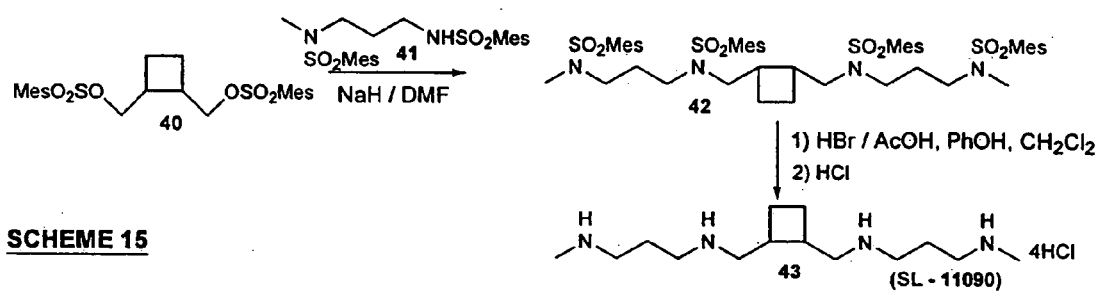
Figure 36:
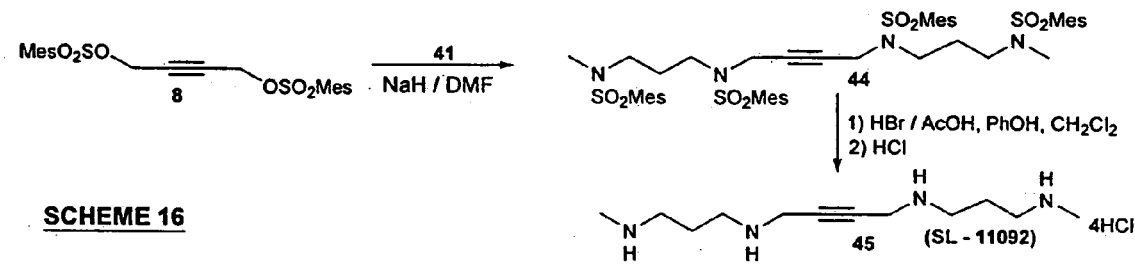
Figure 36:
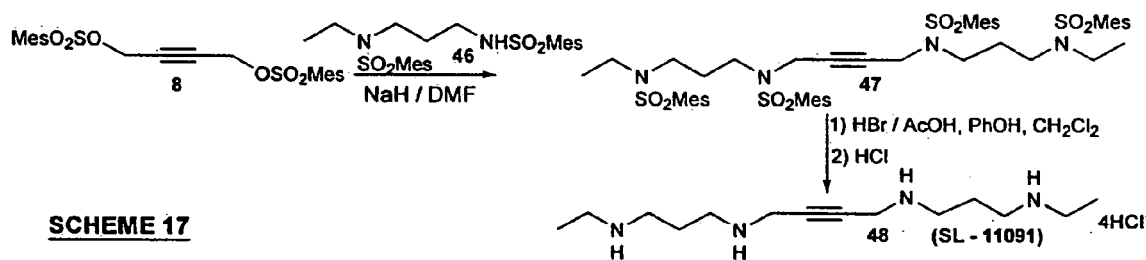

FIG. 36 illustrates additional synthetic methodology used to prepare the compounds of the invention.

Figure 37:
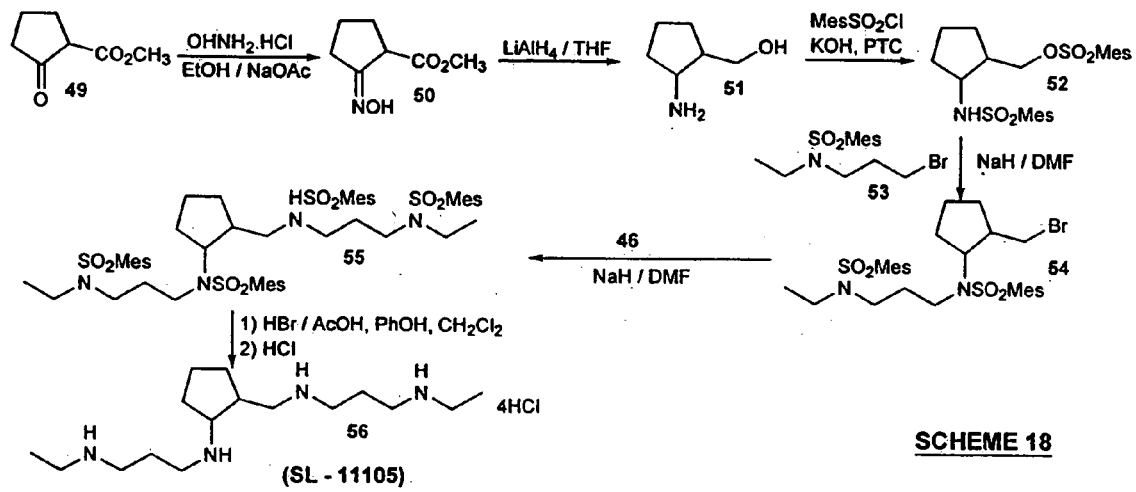
Figure 37:
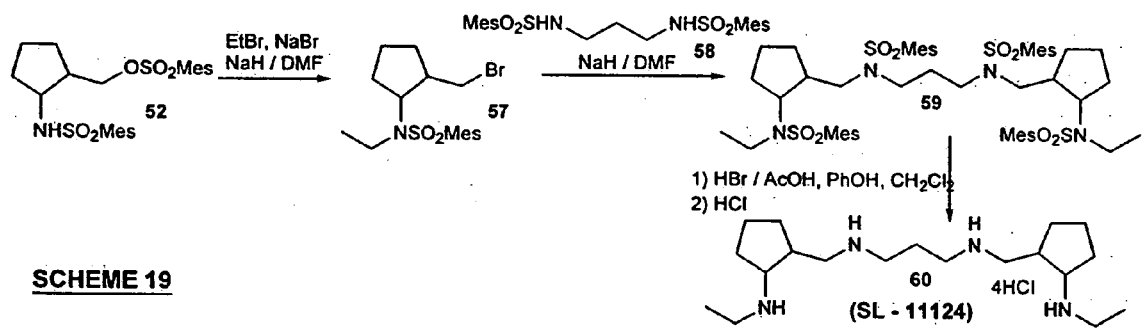
Figure 37:
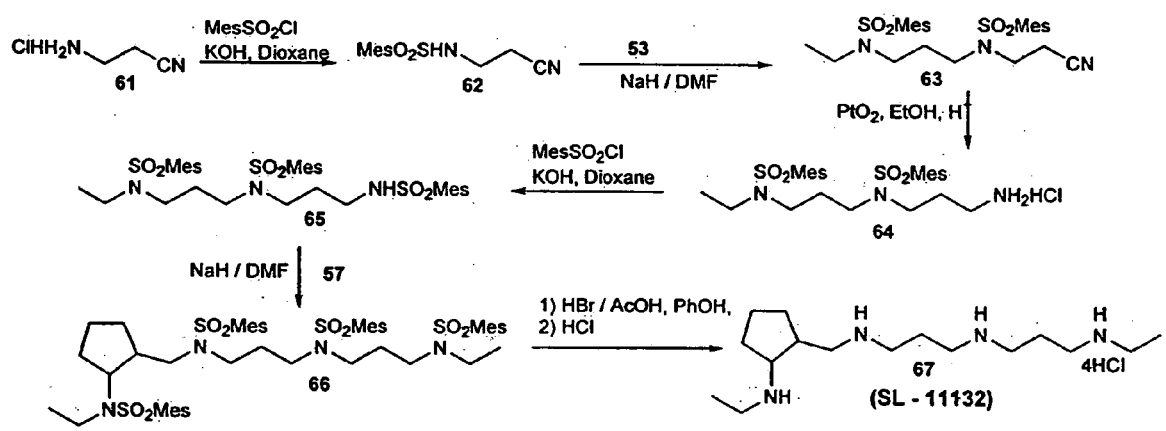

FIG. 37 illustrates additional synthetic methodology used to prepare the compounds of the invention.

Figure 38:
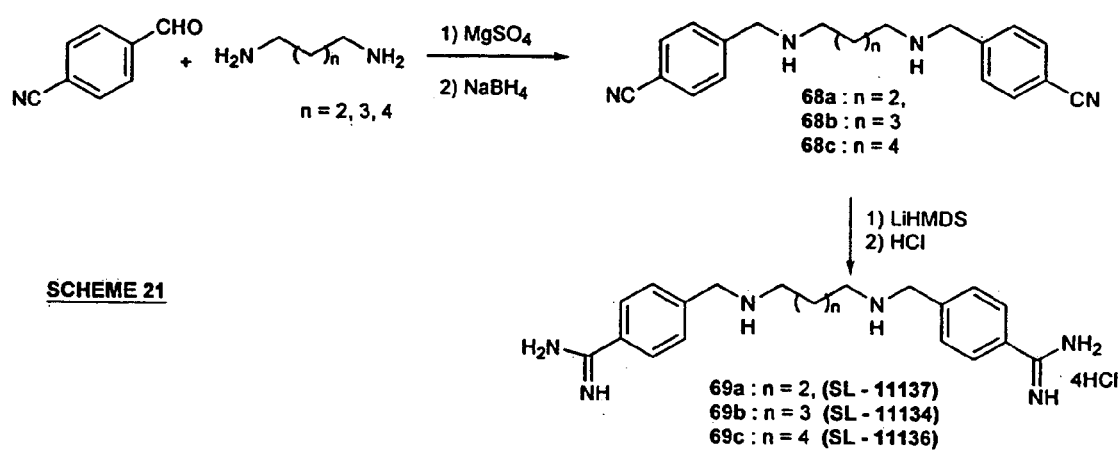

FIG. 38 illustrates additional synthetic methodology used to prepare the compounds of the invention.

Figure 39:
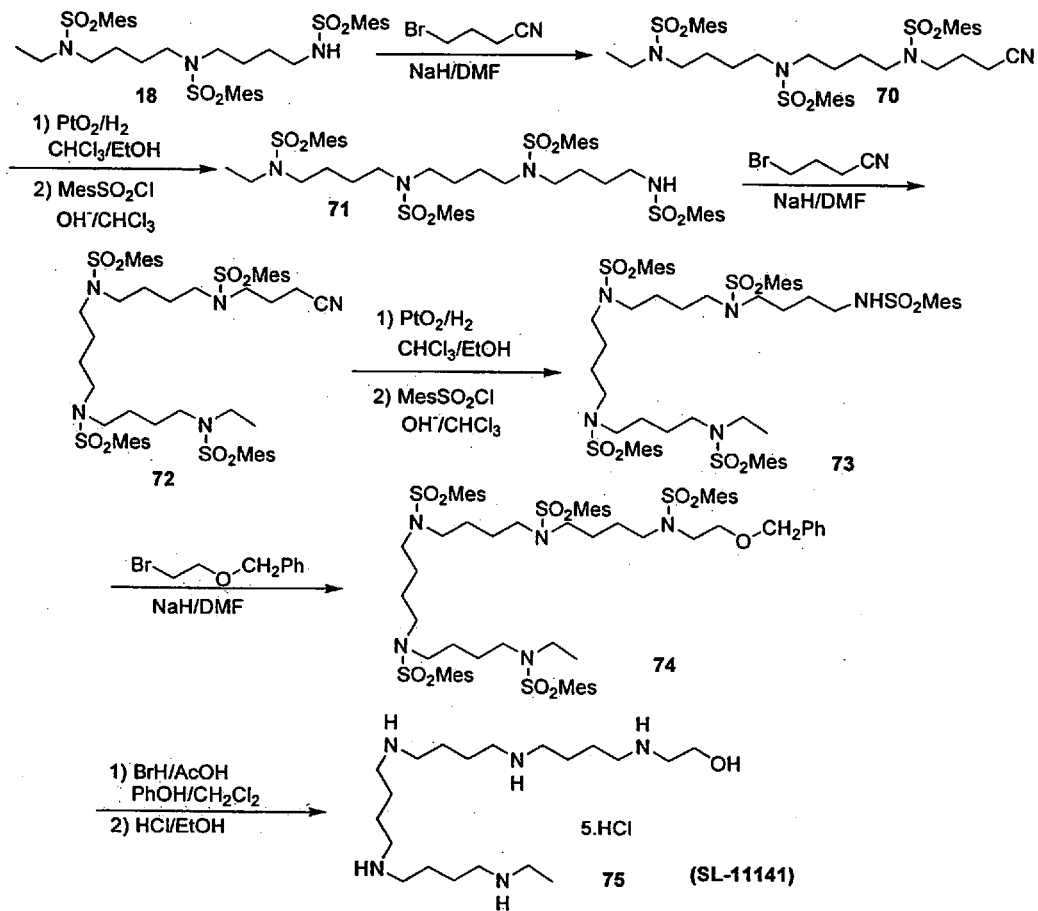
Figure 39:
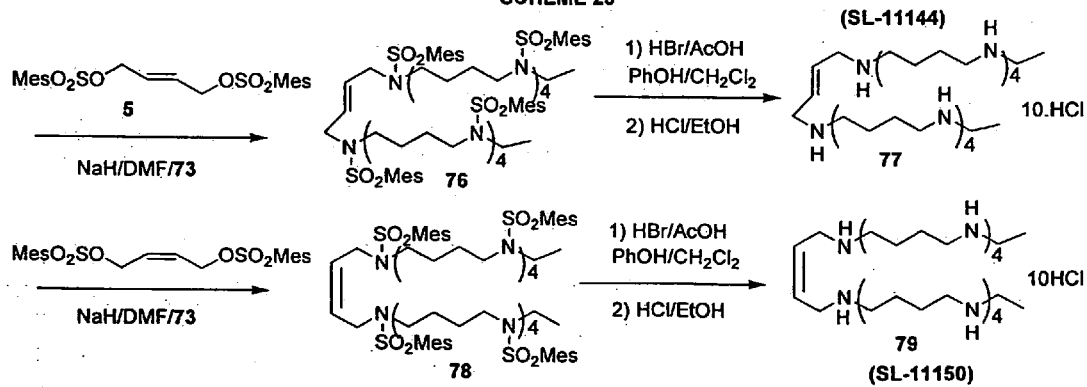

FIG. 39 illustrates additional synthetic methodology used to prepare the compounds of the invention.

Figure 40A:
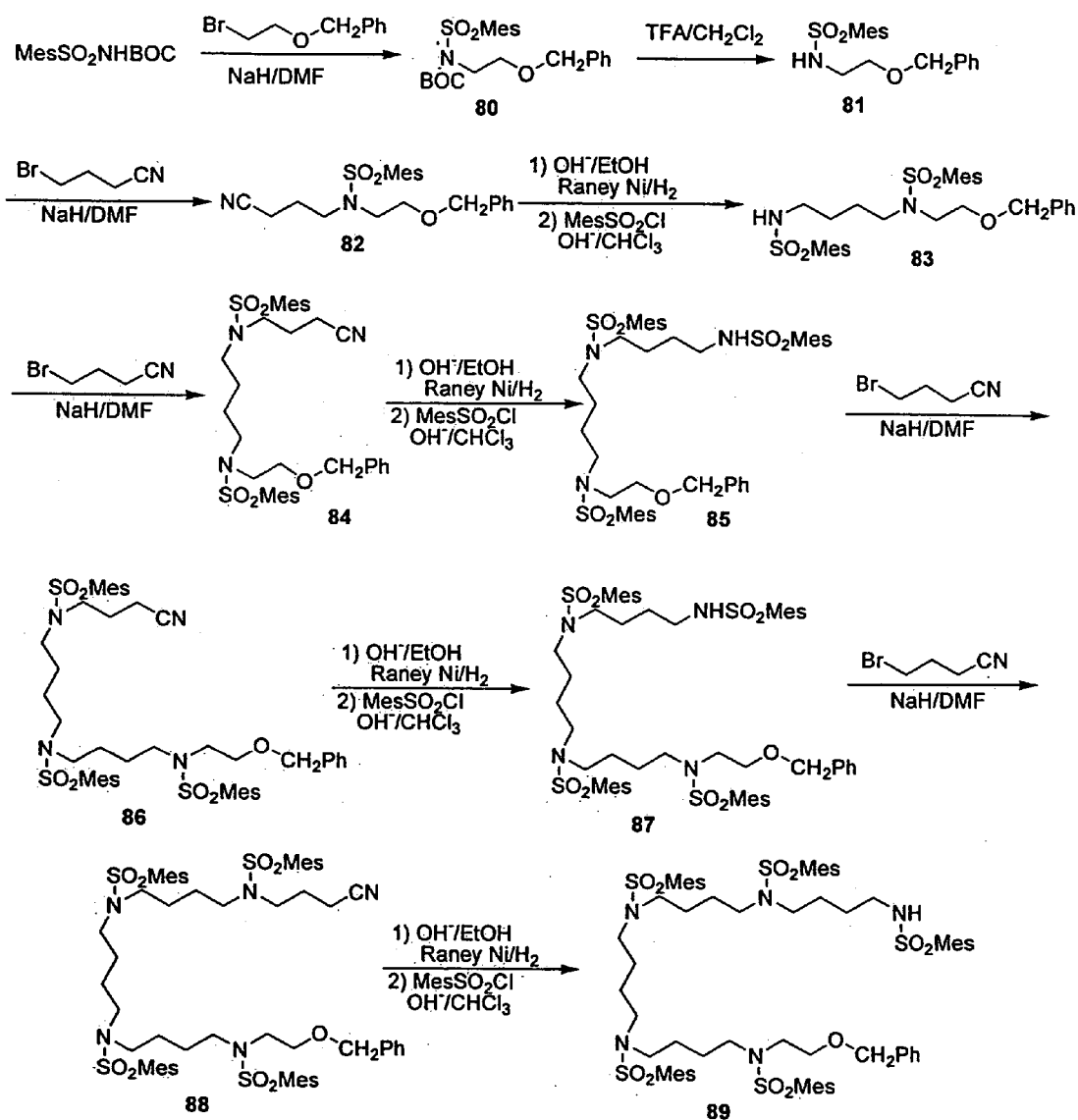

FIG. 40A illustrates additional synthetic methodology used to prepare the compounds of the invention.

Figure 40B:
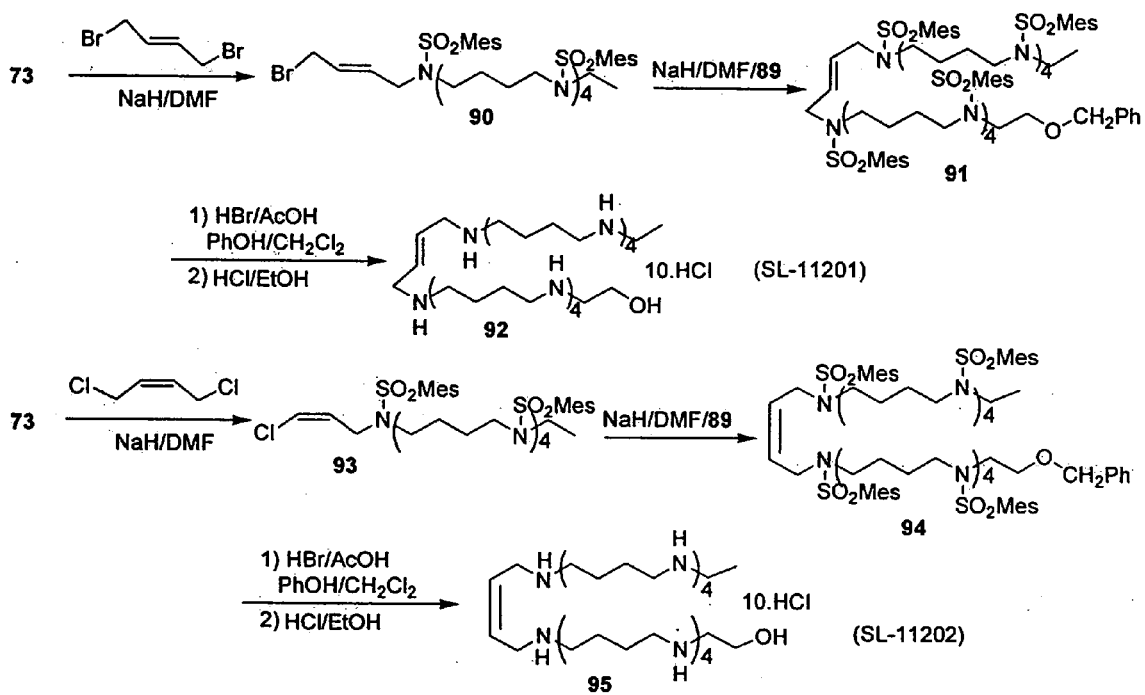

FIG. 40B illustrates additional synthetic methodology used to prepare the compounds of the invention.

Figure 41:
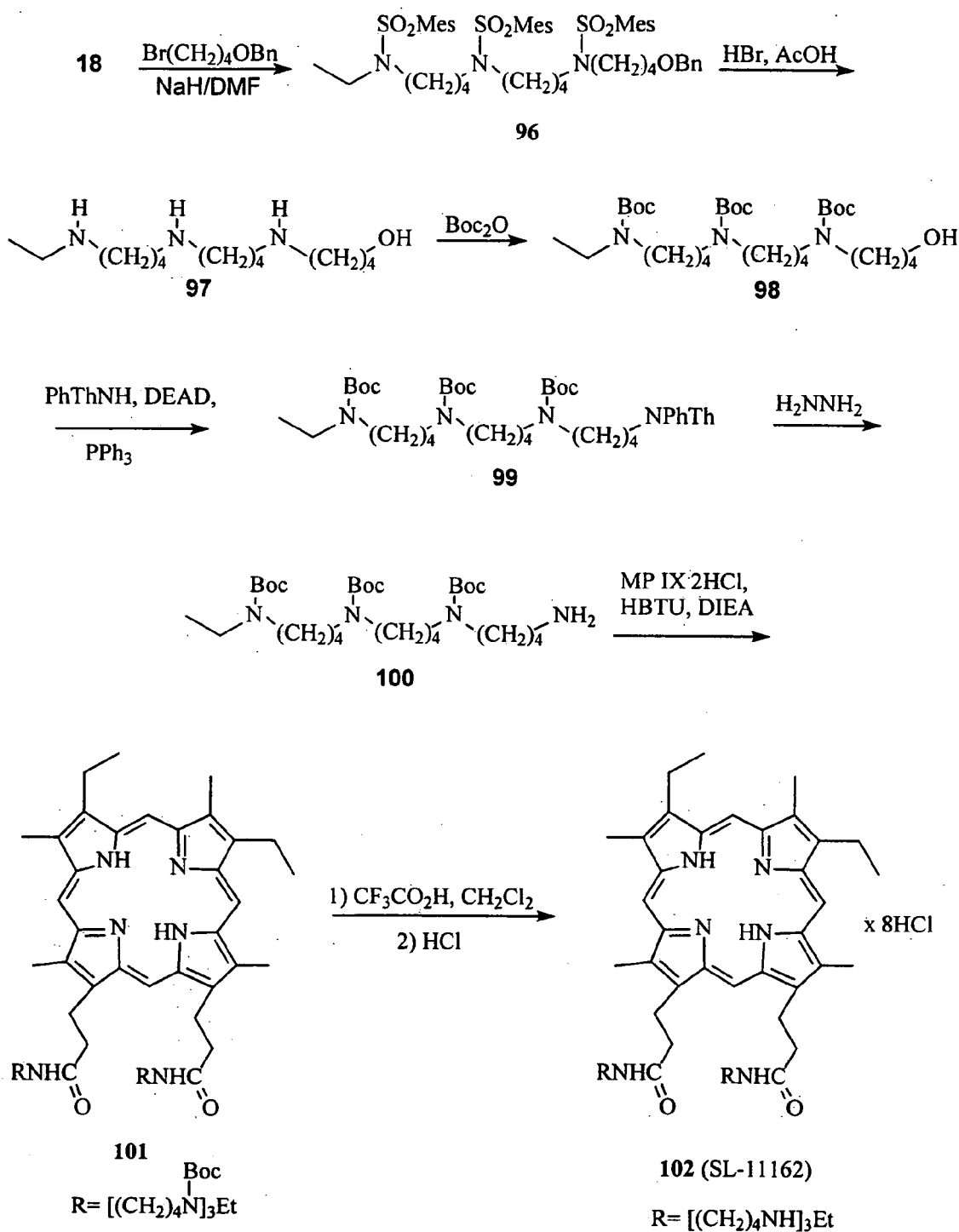

FIG. 41 illustrates synthetic methodology used to prepare porphyrin-polyamine conjugages of the invention.

Figure 42:
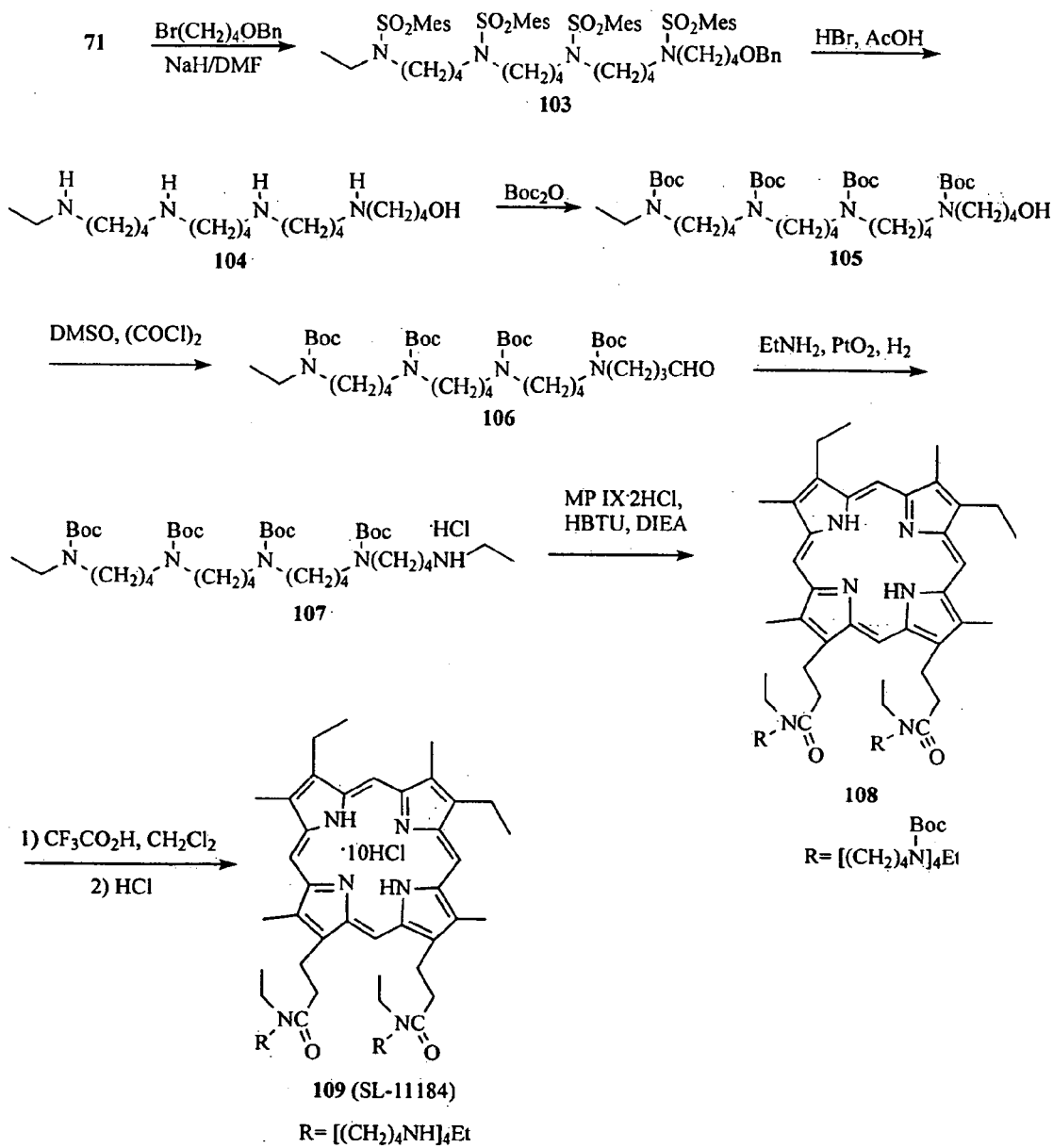

FIG. 42 illustrates additional synthetic methodology used to prepare porphyrin-polyamine conjugages of the invention.

Figure 43:
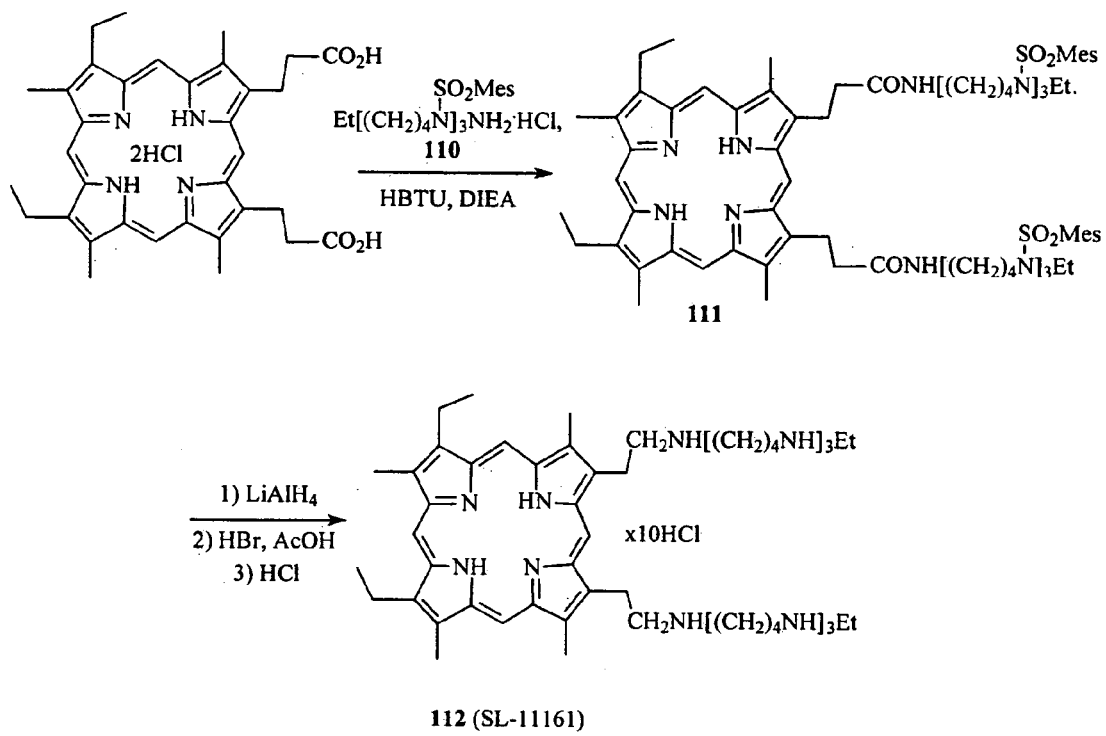

FIG. 43 illustrates additional synthetic methodology used to prepare porphyrin-polyamine conjugages of the invention.

Figure 44:
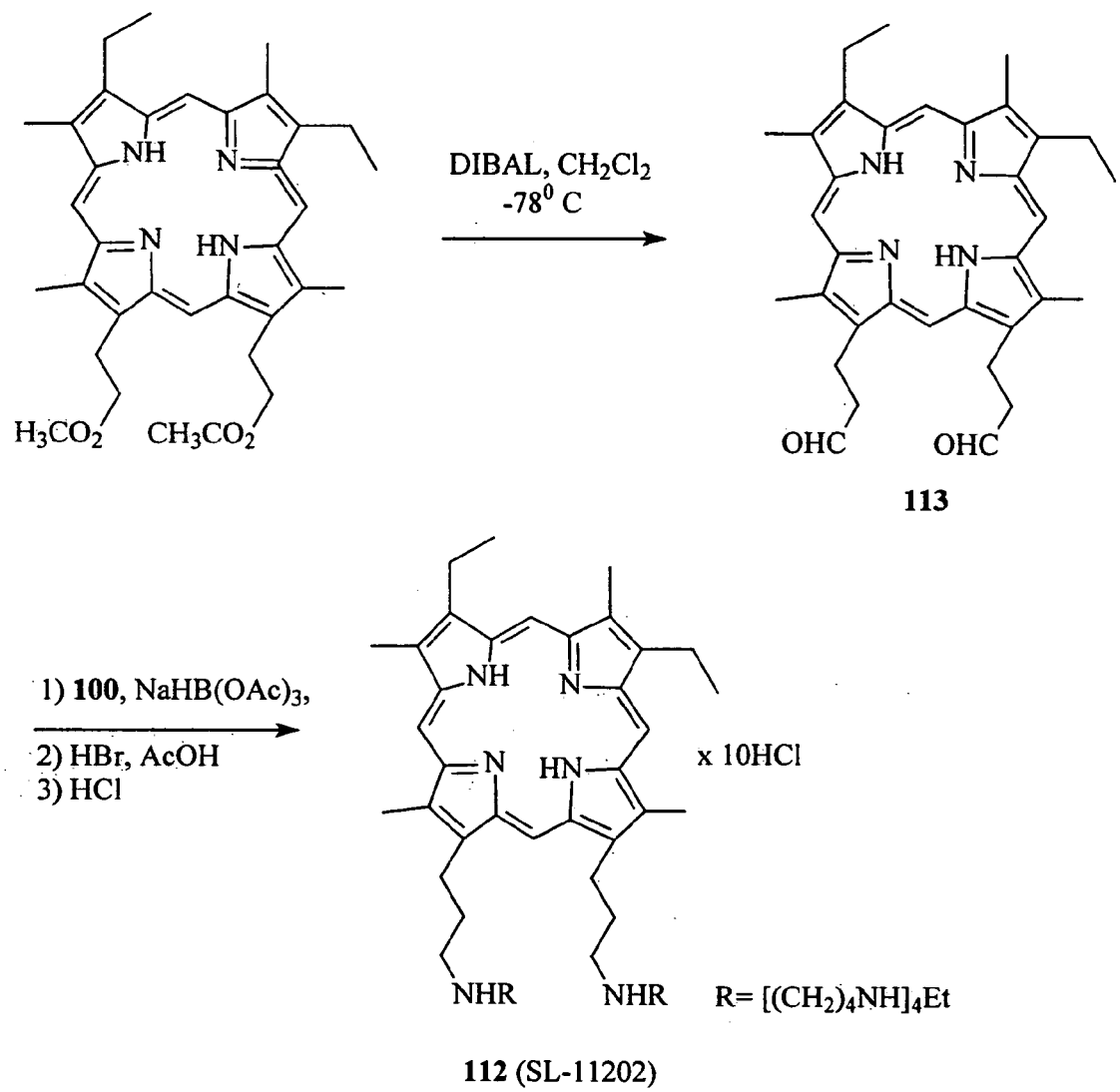

FIG. 44 illustrates additional synthetic methodology used to prepare porphyrin-polyamine conjugages of the invention.

Figure 45:
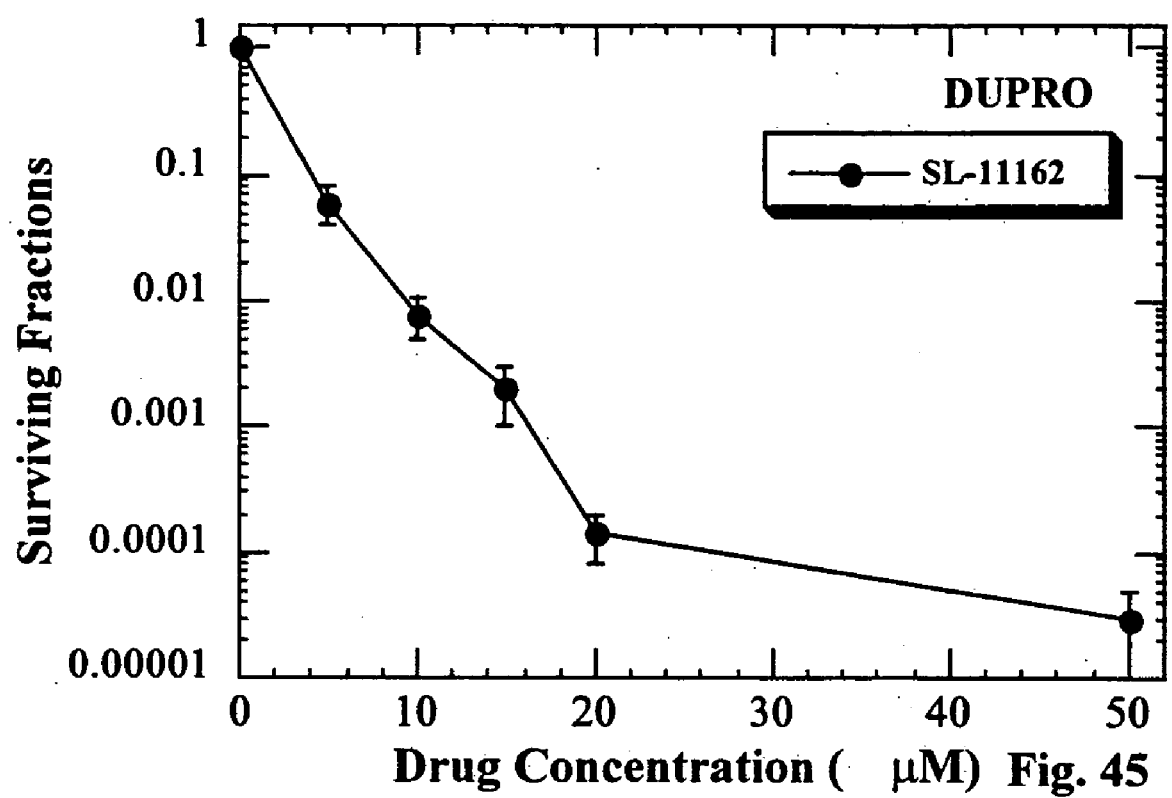

FIG. 45 is a graph depicting the in vitro effect of increasing concentrations of SL-11162 on the survival of human prostate cancer cells DuPro. The concentrations of SL-11162 are plotted in the X-axis and the corresponding surviving fractions of cells are plotted in the Y-axis.

Figure 46:
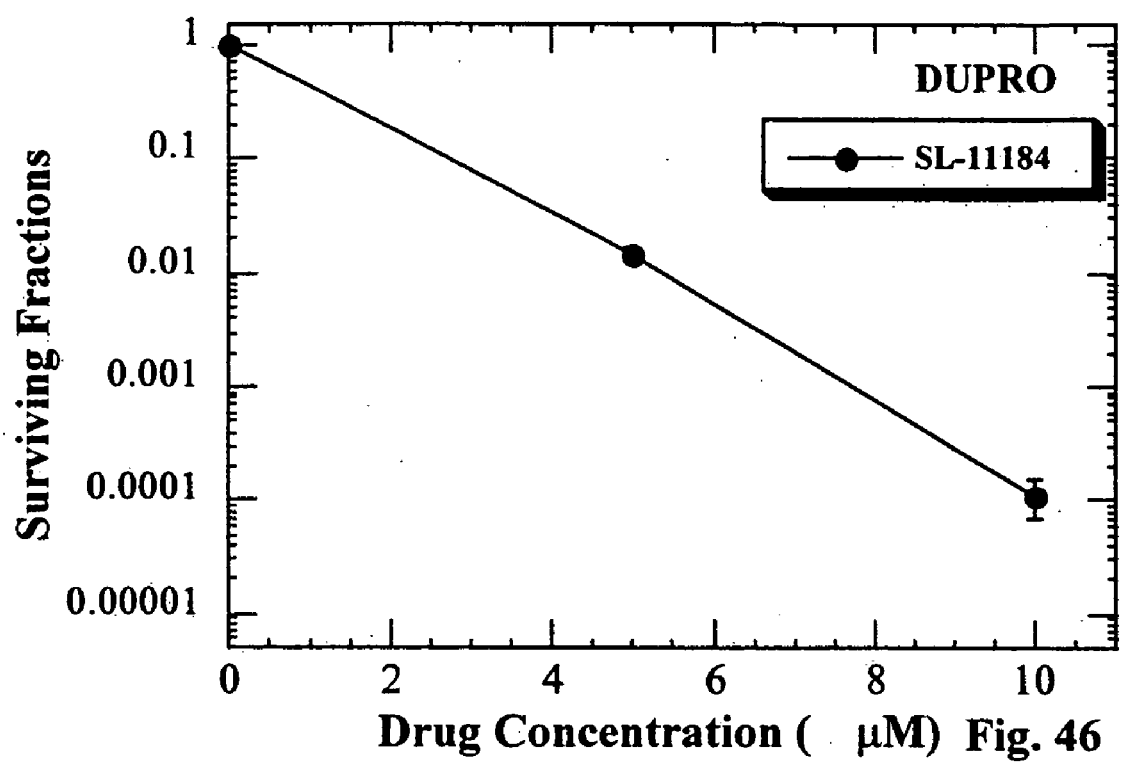

FIG. 46 is a graph depicting the in vitro effect of increasing concentrations of SL-11184 on the survival of human prostate cancer cells DuPro. The concentrations of SL-11184 are plotted in the X-axis and the corresponding surviving fractions of cells are plotted in the Y-axis.

Figure 47:
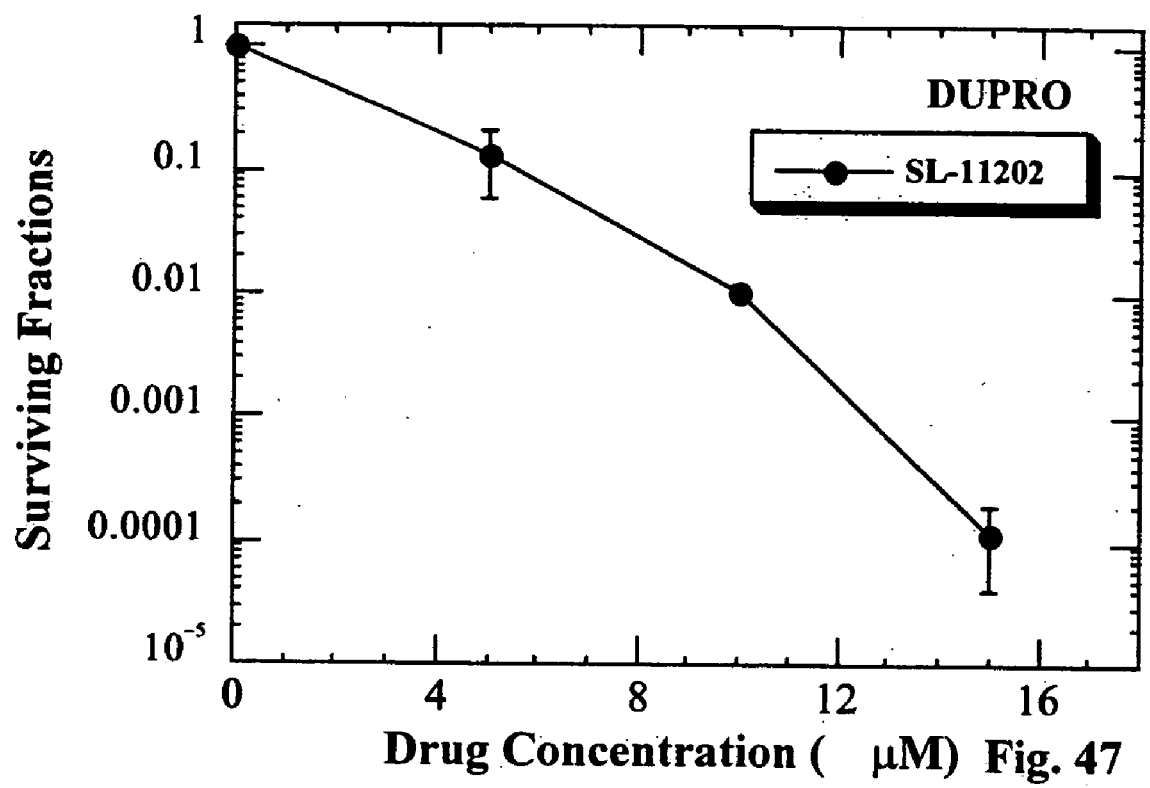

FIG. 47 is a graph depicting the in vitro effect of increasing concentrations of SL-11202 on the survival of human prostate cancer cells DuPro. The concentrations of SL-11202 are plotted in the X-axis and the corresponding surviving fractions of cells are plotted in the Y-axis.

Figure 48:
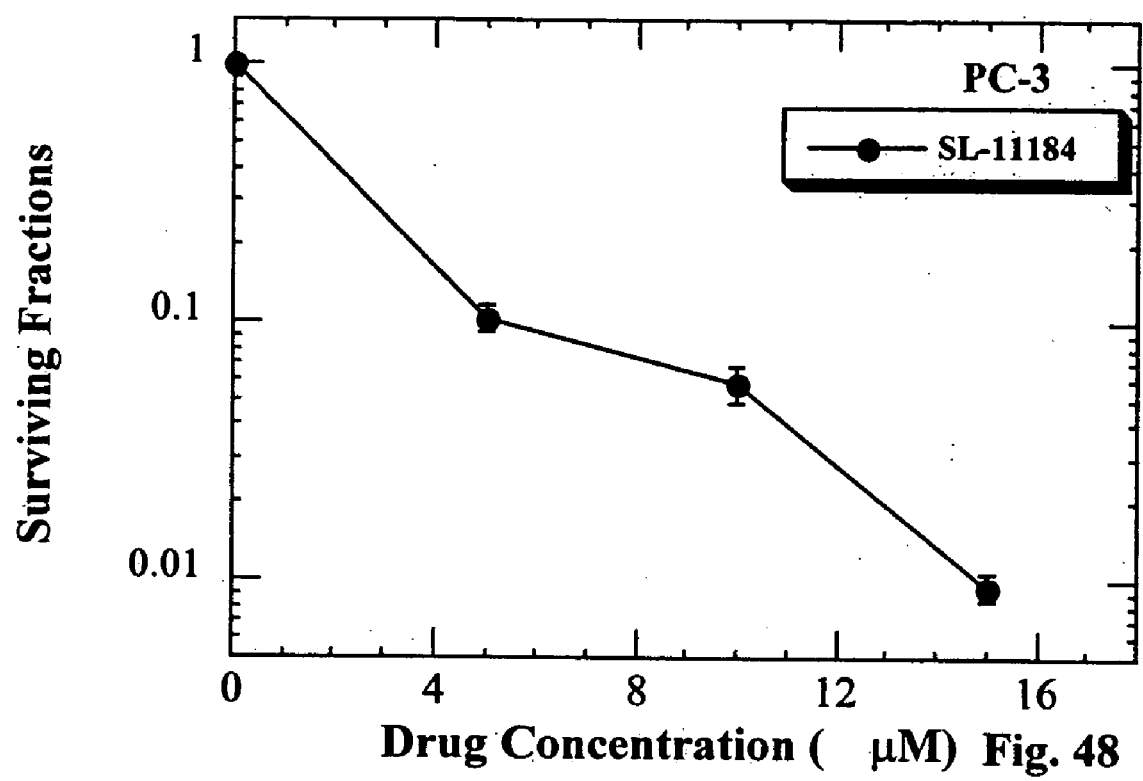

FIG. 48 is a graph depicting the in vitro effect of increasing concentrations of SL-11184 on the survival of human prostate cancer cells PC-3. The concentrations of SL-11184 are plotted in the X-axis and the corresponding surviving fractions of cells are plotted in the Y-axis.

FIG. 49 is a graph depicting the in vitro effect of increasing concentrations of SL-11202 on the survival of human prostate cancer cells PC-3. The concentrations of SL-11202 are plotted in the X-axis and the corresponding surviving fractions of cells are plotted in the Y-axis.

MODES FOR CARRYING OUT THE INVENTION

The present invention encompasses novel conformationally restricted polyamine analogs and compositions comprising these compounds. These analogs are useful as anti-proliferatives for suppressing cell proliferation. The analogs find use in treatment of various diseases, including use as anti-cancer agents in the treatment of various cancers. The analogs are also useful as anti-microbial agents. Novel polyamine analogs include the compounds shown in the synthetic schemes (FIGS. 33–40) and Table 1.

The invention also includes polyamine-porphryin conjugates. These conjugates include the compounds depicted in Table 2 and those shown in the synthetic schemes (FIGS. 41–44).

Definitions

By "polyamine analog" is meant an organic cation structurally similar but non-identical to polyamines such as spermine and/or spermidine and their precursor, diamine putrescine. By a "polyamine", a term well-understood in the art, is meant any of a group of aliphatic, straight-chain amines derived biosynthetically from amino acids; polyamines are reviewed in Marton et al. (1995) *Ann. Rev. Pharm. Toxicol.* 35:55–91. Polyamine analogs can be branched or un-branched. Polyamine analogs include, but are not limited to, BE-4444 [1,19-bis(ethylamino)-5,10,15-triazanonadecane]; BE-333 [N1,N11-diethylnorspermine; DENSPM; 1,11-bis (ethylamino)-4,8-diazaundecane; thermine; Warner-Parke-Davis]; BE-33 [N1,N7-bis(ethyl) norspermidine]; BE-34 [N1,N8-bis(ethyl) spermidine]; BE-44 [N1,N9-bis(ethyl) homospermidine]; BE-343 [N1,N12-bis (ethyl) spermine; diethylspermine-N1-N12; DESPM]; BE-373 [N,N'-bis (3-ethylamino) propyl)-1,7-heptane diamine, Merrell-Dow]; BE-444 [N1,N14-bis(ethyl) homospermine; diethylhomospermine-N1-N14]; BE-3443 [1,17-bis(ethylamino)-4,9,14-triazaheptadecane]; and BE-4334 [1,17-bis(ethylamino)-5,9,13-triazaheptadecane]; 1,12-Me$_2$-SPM [1,12-dimethylspermine]. Additional polyamine analogs are disclosed in International Patent Application WO 98/17624 and U.S. Pat. No. 5,889,061. Various novel polyamine analogs are illustrated in the synthetic schemes in FIGS. 33–40, and Table 1.

By "conformationally restricted" is meant that, in a polyamine analog, at least two amino groups in the molecule are locked or limited in spatial configuration relative to each other. The amino groups within the molecule may be primary, secondary, tertiary, or quarternary, and are preferably primary or secondary amino groups. The relative movement of two amino groups can be restricted, for example, by incorporation of a cyclic or unsaturated moiety between them (exemplified, but not limited to, a ring, such as a three-carbon ring, four-carbon ring, five-carbon-ring, six-carbon ring, or a double or triple bond, such as a double or triple carbon bond). Groups restricting conformational flexibility by means of steric hindrance, yet structurally favorable to the anti-proliferative, anti-cancer, or anti-microbial effects, can also be used according to the invention. A "conformationally restricted" polyamine analog can comprise at least two amino groups which are conformationally restricted relative to each other, but can also further comprise amino groups which are not conformationally restricted relative to each other. Flexible molecules such as spermine and BE-444 can have a myriad of conformations and are therefore not conformationally restricted. Conformationally restricted polyamine analogs include, but are not limited to, the compounds listed in Table 1 and illustrated in FIGS. 33–40.

An "indication" includes any symptom or the like which points out a suitable remedy or treatment or which shows the presence of a disease or other unhealthful condition. As used herein, an "indication" also includes a "disease" itself, where a disease is a condition of an organ, part, structure or system of the body in which there is incorrect function resulting from the effect(s) of heredity, infection, diet and/or environment, and/or other causes. The indication can include cancer. By "cancer" is meant the abnormal presence of cells which exhibit relatively autonomous growth, so that they exhibit an aberrant growth phenotype characterized by a significant loss of cell proliferation control. Cancerous cells can be benign or malignant. In various embodiments, the cancer affects cells of the bladder, blood, brain, breast, colon, digestive tract, lung, ovaries, pancreas, prostate gland, or skin. In other embodiments, the indication can also include, but is not limited to, Alzheimer's disease, epilepsy, multiple sclerosis, problems associated with tissue grafts and organ transplants, psoriasis, restenosis, stomach ulcers, or tissue overgrowth after surgery. In other embodiments, the indication is an infection or infestation of parasites, bacteria, fungi or insects.

An "individual" is a vertebrate, preferably a mammal, more preferably a human. Mammals include, but are not limited to, farm animals, sport animals, rodents, primates, and pets. Preferably, the individual is known or suspected to be afflicted by cancer or another disease treatable with a polyamine analog.

An "effective amount" or "therapeutic amount" is an amount sufficient to effect beneficial or desired clinical results. An effective amount can be administered in one or more administrations. For purposes of this invention, an effective amount of a polyamine analog is an amount that is sufficient to palliate, ameliorate, stabilize, reverse, slow or delay the progression of the disease state. A therapeutic amount of a polyamine of the present invention is an amount sufficient to inhibit proliferation of diseased cells. A polyamine analog is considered to be an effective anti-tumor or anti-cancer agent if it is effective against at least one type of cancer cell line, even if it is not effective against a different cell line.

As used herein, "treatment" is an approach for obtaining beneficial or desired clinical results. For purposes of this invention, beneficial or desired clinical results include, but are not limited to, alleviation of symptoms, diminishment of extent of, disease, stabilization (i.e., not worsening) of state of disease, prevention of spread (i.e., metastasis) of disease, delay or slowing of disease progression, amelioration or palliation of the disease state, improvement in quality of enjoyment of life, and remission (whether partial or total), whether detectable or undetectable. "Treatment" can also mean prolonging survival as compared to expected survival if not receiving treatment.

"Palliating" a disease means that the extent and/or undesirable clinical manifestations of a disease state are lessened and/or time course of the progression is slowed or lengthened, as compared to not administering polyamine analogs of the present invention. Prefered polyamine analogs for methods of treating and palliating a disease include the compounds illustrated in Table 1.

Polyamine Analogs of the Present Invention

Novel polyamine analogs can be first designed based on current knowledge of polyamines and their analogs. Without wishing to be bound by any particular theory explaining polyamine analog toxicity, the inventors suggest that relevant knowledge includes that related to polyamine interaction with DNA and ability to induce structural changes in nucleic acids. Feuerstein et al. (1991); Gosule et al. (1978) *J. Mol. Biol.* 121:311–326; Behe et al. (1981) *Proc. Natl. Acad. Sci. USA* 78:1619–23; Jain et al. (1989) *Biochem.* 28:2360–2364; and Basu et al. (1990) *Biochem. J.* 269: 329–334. Alternatively, a novel polyamine analog can be designed based on its likely ability to inhibit cell growth by suppressing natural polyamine synthesis or depleting the intracellular natural polyamine pool. Porter et al. (1988) in *Advances in Enzyme Regulation*, Pergamon Press, pp. 57–79. Preferably, the novel polyamine analog is conformationally restricted. In the next step, the polyamine analog is tested in vitro for efficacy in inhibiting proliferation of diseased cells, such as tumor cells. If the polyamine analog passes this test, it can then be tested in animals, such as nude mice with cancer xenografts. If the compound is found to be efficable, testing can then proceed to human trials.

The present invention encompasses novel polyamine analogs, such as those shown in FIGS. 33–40 and Table 1. Polyamine analogs of the present invention are conformationally restricted. Conformation is a determinant of the spatial arrangement of the pharmacophore or functional groups which interact with receptor binding sites. The latter prefer specific ligand conformations or a specific distribution of conformations. A flexible molecule such as spermine or BE-4444 can have a myriad of conformations. The conformer that binds to the macromolecule (e.g., DNA or RNA) may not necessarily be the one with the lowest energy as determined by spectroscopic methods or theoretically by molecular mechanics calculations. The binding energy of the polyamine binding to the nucleic acid may be overcome with formation of an unstable conformer. Conversely, in the presence of a conformationally rigid analog of a flexible molecule, the host macromolecule might change its overall conformation or the distances from one strand to the other. Hydrogen bonding is the main binding force of either spermine or spermidine associating with the helical region of a tRNA, and very likely also with DNA. Frydman et al. (1992) *Proc. Natl. Acad. Sci. USA* 89:9186–9191; and Fernandez et al. (1994) *Cell Mol. Biol.* 40: 933–944. The secondary amino groups present in the linear spermine analogs BE-343, BE-444, and BE-4444 are the groups most directly involved in the formation of the hydrogen bonds with the paired bases of tRNA. Therefore, these amino groups that usually flank the central four-carbon or three-carbon segment of the polyamine analog can be considered as the pharmacophore of the polyamine analog. When the nitrogens are separated by only a two-carbon segment they are not protonated at pH 7.4 and hence they do not form hydrogen bonds. If these amino groups are locked into various configurations by the incorporation of cyclic or unsaturated moieties into the polyamine analog molecule, a conformationally rigid analog is obtained. When such analogs bind to DNA or tRNA, they will very likely induce a change in the conformation of the nucleic acid strands or loops that may differ from the conformational changes induced by the natural polyamines. A series of conformationally restricted analogs of bis-ethyl-spermine that exhibited cytotoxic activities are illustrated in Table 1 and described below.

Porphyrin-polyamine Conjugates of the Present Invention

The present invention also encompasses novel porphyrin-polyamine conjugates such as those depicted in FIGS. 41–44 and in Table 2. These conjugates combine the selective uptake of porphyrins by tumors with the cytotoxic and cytostatic effects of polyamine analogs. By "porphyrin-polyamine conjugate" is meant any porphyrin compound and any polyamine compound, linked by at least one, and preferably only one, covalent bond. Porphyrin-polyamine conjugates can incorporate any polyamine, whether that polyamine is conformationally restricted or not. Preferably, the polyamine conjugate is conformationally restricted. By "porphyrin" is meant any compound incorporating the porphine ring or derivatives of the porphine ring. Preferred covalent linkages include amide linkages and amine linkages. Examples of porphyrin-polyamine conjugates are depicted in Table 2.

Polyamine Analogs and Inhibition of Cell Growth

Polyamine analogs of the present invention are likely to be useful for treatment of a variety of diseases, including cancer, Alzheimer's disease, epilepsy, multiple sclerosis, problems associated with tissue grafts and organ transplants, psoriasis, restenosis, stomach ulcers, or tissue overgrowth after surgery, or an infection or infestation of parasites, bacteria, fungi or insects. In order to evaluate the efficacy of a particular novel polyamine for a particular medicinal application, the compounds can be first tested against appropriately chosen test cells in vitro. In a non-limiting example, polyamine analogs can be tested against tumor cells, for example, prostate tumor cells. On the basis of the unique nature of polyamine metabolism in the prostate gland, exemplary experiments can utilize cell lines capable of growing in culture as well as in vivo in athymic nude mice, such as LNCaP. Horoszewicz et al. (1983) *Cancer Res.* 43:1809–1818. Culturing and treatment of carcinoma cell lines, cell cycle and apoptosis determinations based on flow cytometry; enzyme assays including ODC, SAMDC and SSAT activities; and high pressure liquid chromatography detection and quantitation of natural polyamines and polyamine analogs are described in the art, for example, Mi et al. (1998) *Prostate* 34:51–60; Kramer et al. (1997) *Cancer Res.* 57:5521–27; and Kramer et al. (1995) *J. Biol. Chem.* 270:2124–2132. Evaluations can also be made of the effects of the novel polyamine analog on cell growth and polyamine-related metabolism. Analysis begins with $IC_{50}$ determinations based on dose-response curves ranging from 0.1 to 1000 µM performed at 72 hr. From these studies, conditions can be defined which produce about 50% growth inhibition and used to: (a) follow time-dependence of growth inhibition for up to 6 days, with particular attention to decreases in cell number, which may indicate drug-induced cell death; (b) characterize analog effects on cell cycle progression and apoptosis using flow cytometry (analysis to be performed on attached and detached cells); (c) examine analog effects on polyamine metabolic parameters, including the biosynthetic enzymes ODC, SAMDC, the catabolic enzyme SSAT and polyamine pools themselves. Analog effects can be normalized to intracellular concentrations (by HPLC analysis), which also provide an indication of their relative ability to penetrate cells. Marked differences in analog uptake can be further characterized by studying analog ability to utilize and regulate the polyamine transporter, as assessed by competition studies using radiolabeled spermidine, as previously described in Mi et al. (1998).

In vivo Testing of Polyamine Analogs and Porphyrin-polyamine Conjugates

Analogs and conjugates found to have potent or mechanism-based anti-proliferative activity in vitro towards cultured carcinoma cells can be evaluated in in vivo model systems. The first goal is to determine the relative toxicity of the analogs or conjugates in non-tumor-bearing animals, such as DBA/2 mice. Groups of three animals each can be injected intraperitoneally with increasing concentrations of a compound, beginning at, for example, 10 mg/kg. Toxicity as indicated by morbidity is closely monitored over the first 24 hr. A well-characterized polyamine analog, such as BE-333, can be used as an internal standard in these studies, since a data base has already been established regarding acute toxicity via a single dose treatment relative to chronic toxicity via a daily ×5 d schedule. Thus, in the case of new analogs, single dose toxicity relative to BE-333 is used to project the range of doses to be used on a daily ×5 d schedule.

After the highest tolerated dosage on a daily ×5 d schedule is deduced, antitumor activity is determined. Typically, tumors can be subcutaneously implanted into nude athymic mice by trocar and allowed to reach 100–200 $mm^3$ before initiating treatment by intraperitoneal injection daily ×5 d. Most analogs or conjugates can be given in a range between 10 and 200 mg/kg. Analogs or conjugates can be evaluated at three treatment dosages with 10–15 animals per group (a minimum of three from each can be used for pharmacodynamic studies, described below). Mice can be monitored and weighed twice weekly to determine tumor size and toxicity. Tumor size is determined by multi-directional measurement from which volume in $mm^3$ is calculated. Tumors can be followed until median tumor volume of each group reaches 1500 $mm^3$ (i.e., 20% of body weight), at which time the animals can be sacrificed. Although the initial anti-tumor studies focuses on a daily ×5 d schedule, constant infusion can be performed via Alzet pump delivery for 5 days since this schedule dramatically improves the anti-tumor activity of BE-333 against A549 human large cell hung carcinoma. Sharma et al. (1997) *Clin. Cancer Res.* 3:1239–1244. In addition to assessing anti-tumor activity, free analog levels or conjugate levels in tumor and normal tissues can be determined in test animals.

Methods of Administration of Polyamine Analogs and Porphyrin-polyamine Conjugates The polyamine analogs or porphyrin-polyamine conjugates of the present invention can be administered to an individual via any route known in the art, including, but not limited to, those disclosed herein. Preferably administration of the novel polyamine analogs or porphyrin-polyamine conjugates is by intravenous routes. Other methods of administration include but are not limited to, oral, intraarterial, intratumoral, intramuscular, subcutaneous, intraperitoneal, gastrointestinal, and directly to a specific or affected organ. The novel polyamine analogs and porphyrin-polyamine conjugates described herein are administratable in the form of tablets, pills, powder mixtures, capsules, injectables, solutions, suppositories, emulsions, dispersions, food premixes, and in other suitable forms. Additional methods of administration are known in the art. The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly (vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form can also contain non-toxic auxiliary substances such as emulsifying, preserving, or wetting agents, and the like. A suitable carrier is one which does not cause an intolerable side effect, but which allows the novel polyamine analogs or porphyrin-polyamine conjugates to retain its pharmacological activity in the body. Formulations for parenteral and nonparenteral drug delivery are known in the art and are set forth in *Remington's Pharmaceutical Sciences,* 18th Edition, Mack Publishing (1990). Solid forms, such as tablets, capsules and powders, can be fabricated using conventional tableting and capsule-filling machinery, which is well known in the art. Solid dosage forms can contain any number of additional non-active ingredients known to the art, including excipients, lubricants, dessicants, binders, colorants, disintegrating agents, dry flow modifiers, preservatives, and the like. Liquid forms for ingestion can be formulated using known liquid carriers, including aqueous and non-aqueous carriers, suspensions, oil-in-water and/or water-in-oil emulsions, and the like. Liquid formulations can also contain any number of additional non-active ingredients, including colorants, fragrance, flavorings, viscosity modifiers, preservatives, stabilizers, and the like. For parenteral administration, novel polyamine analogs or porphyrin-polyamine conjugates can be administered as injectable dosages of a solution or suspension of the compound in a physiologically acceptable diluent or sterile liquid carrier such as water or oil, with or without additional surfactants or adjuvants. An illustrative list of carrier oils would include animal and vegetable oils (peanut oil, soy bean oil), petroleum-derived oils (mineral oil), and synthetic oils. In general, for injectable unit doses, water, saline, aqueous dextrose and related sugar solutions, and ethanol and glycol solutions such as propylene glycol or polyethylene glycol are preferred liquid carriers. The pharmaceutical unit dosage chosen is preferably fabricated and administered to provide a final concentration of drug at the point of contact with the cancer cell of from 1 µM to 10 mM. More preferred is a concentration of from 1 to 100 µM. As with all pharmaceuticals, the optimal effective concentration of novel polyamine analogs or porphyrin-polyamine conjugates will need to be determined empirically and will depend on the type and severity of the disease, route of administration, disease progression and health and mass or body area of the patient. Such determinations are within the skill of one in the art. Polyamine analogs or porphyrin-polyamine conjugates can be administered as the sole active ingredient, or can be administered together, or in combination with another active ingredient, including, but not limited to, cytotoxic agents, antibiotics, antimetabolites, nitrosourea, vinca alkaloids, polypeptides, antibodies, cytokines, etc.

The following examples are provided to illustrate but not limit the invention.

EXAMPLES

Synthesis of Conformationally-Restricted Polyamine Analogs and of Porphyrin-polyamine Conjugates a) Spermine and Homospermine Analogs Containing a Conformational Restriction.

Scheme 2 exemplifies a $N^\alpha$, $N^\omega$-bisethyl homospermine analog 7 containing a central trans-unsaturated bond. Amide 4 was prepared as described in Scheme 1 by alkylation of amide 1 with bromobutyronitrile to give 2, followed by reduction of the nitrile to the amine 3 that was mesitylsulfonated to 4. Trans-allylic diester 5 was used to alkylate amide 4 and the tetramide 6 was obtained. Deprotection gave the trans-tetramide 7 (Scheme 2).

Introduction of a triple bond in the butane segment of homospermine also reduces its mobility. This was achieved by starting with the butyne diester 8 and following the sequence of reactions outlined above (Scheme 3). Schemes 15–20 are further examples of the synthesis of polyamine spermine and homospermine analogs of this type.

b) Synthesis of Pentamines with Conformational Restrictions.

Schemes 4–14 are outlines of the syntheses of conformationally restricted pentamines. Scheme 4 depicts the reaction of cis-1-chloro-4-phthalimido butene with amide 1 to give 11. Hydrazinolysis of 11 gave 12 which was amidated to 13. Reaction of the latter with 1,4-diiodobutane gave 14, while reaction with equimolar amounts of cis-1,4-dichlorobutene gave 15.

Amide 4 was alkylated with either 4-chlorobutyronitrile to give 16 or with cis-1,4-dichlorobutene to give 19. Nitrile 16 was reduced with hydrogen over Ni Raney to the amine 17 and the latter transformed in to the amide 18 (Scheme 5). Condensation of 18 with the chloroalkyl intermediate 15 gave the pentamide 20 that was deprotected to the pentamine 21 (Scheme 6). Condensation of 18 with the iodoalkyl derivative 14 gave 22 that was deprotected to the pentamine 23 (Scheme 7). Condensation of 18 and 19 gave pentamide 24 that was deprotected to the pentamine 25 (Scheme 8). Using 14 as the alkylating agent, mesitylenesulfonamide was dialkylated to give 26, and the latter deprotected to give 27 (Scheme 9). The analogous reaction carried out using 15 as alkylating agent, gave 28 and after deprotection led to the pentamine 29 (Scheme 10).

Alkylation of mesitylenesulfonamide with 19 gave the pentamide 30, which was deprotected to 31 (Scheme 11). When 19 was used to alkylate an equimolar amount of mesitylenesulfonamide then 32 was obtained. Alkylation of 32 with 14 gave 33, that was deprotected to give 34 (Scheme 12). When the chloroalkyl intermediate 15 was used to alkylate one equivalent of mesitylenesulfonamide, then the triamide 35 was obtained. Reaction of 35 with 14 gave 36 which was then deprotected to 37 (Scheme 13). Condensation of 35 and 19 gave the pentamide 38 that was deprotected to 39 (Scheme 14). The above mentioned Schemes describe the synthesis of cis-compounds. The same synthetic methodology can be used to obtain the trans-isomers, or cis and trans bonds in different segments within the same molecule.

c) Polyamine Analogs with Diamidine Substituents.

A new class of polyamine analogs is shown in Scheme 21. They derive from 1,4-dibenzylputrescine, 1,5-dibenzylcadaverine, and 1,6-dibenzylhexanediamine. They are diamidine derivatives, where the diamidine residues are carrier groups that have been shown to be efficient in the transport of drugs into different protozoa. The general procedure of synthessis was based on the condensation of 4-cyanobenzaldehyde with the diaminoalkanes to give the Schiff bases, followed by reduction in situ to the corresponding dinitriles 68. The latter were converted to the diamidines 69 through their iminoethers.

d) Synthesis of Oligoamines.

Scheme 22 describes the synthesis of a N-2 hydroxyethyl derivative of a pentamine such as 75. Starting wtih 18, alkylation with 4-bromobutyronitrile gave 70. Reduction of the nitrile of 70 and mesitylenesulfonylation of the resulting amino group gave 71. It was alkylated again with 4-bromobutyronitrile to give 72, and again reduced and mesitylsulfonylated to give 73. The latter was then alkylated with the benzyl ester of 2-bromoethanol to give 74. Treatment with hydrobromic acid in acetic acid cleaved both the mesitylene sulfonyl protecting groups and the benzyl ether residue to give 75.

Scheme 23 reports the synthesis of a trans-decamine 77 and of a cis-decamine 79. Starting with the pentamide 73

(Scheme 22) and by reaction with trans-diester 5 (Scheme 2) the decamide 76 was prepared, which on deprotection gave 77 as a decahydrochloride. In an analogous manner, by condensation of 73 with the cis-1,4-dimesityleneoxy-2-butene, the decamide 78 was prepared, which on deprotection gave 79 as a decahydrochloride.

Scheme 24 outlines the synthesis of a N-2 hydroxyethyl trans-decamine 92 and a cis-2-hydroxyethyl decamine 95. The procedure repeats almost all the procedures described in the foregoing schemes. The synthesis of 80 proceeded by alkylating BOC-mesitylenesulfonamide with the benzyl ester of 2-bromoethanol. Cleavage of the BOC protecting group leads to 81, alkylation with 4-bromobutyronitrile then gave 82, and after reduction of the nitrile group and reaction with mesitylene sulfonyl chloride the diamide 83 was obtained. Again, alkylation with 4-bromobutyronitrile led to 84, reduction and mesitylsulfonylation gave 85, alkylation of 85 gave 86, reduction and mesitylsulfonylation gave 87, and alkylation, reduction and mesitylsulfonylation performed on 87 gave 89. Alkylation of 73 with trans-1,4-dibromo-2-butene gave 90. Alkylation of 89 with 90 gave 91, which after deprotection gave the trans-ω-hydroxy-decamine 92. Alkylation of 73 with cis-1,4-dichloro-2-butene gave 93. Alkylation of 89 with 93 gave 94. Deprotection of 94 gave the cis-ω-hydroxy-decamine 95, isomeric with 92.

e) Synthesis of Porphyrin-polyamine Conjugates.

Scheme 25 outlines the synthesis of porphyrin-polyamine. Starting with the above mentioned amide 18 (Scheme 5), alkylation with the benzyl ether of 4-bromobutanol gave 96. Treatment with acid cleaved both the sulfonate and the benzyl protecting groups to give 97. Protection of the free amino residues with Boc followed by Mitsunobu reaction using phthalimide gave 99. Cleavage of the phthalyl protecting group with hydrazine hydrate gave polyamine 100. It was condensed with mesoporphyrin IX to give 101, and after cleavage of the Boc protecting group 102 (SL-11162) was obtained.

Scheme 26 outlines the synthesis of a porphyrin-bisethylpolyamine conjugate. The synthesis of the intermediate 105 follows the pattern described above. The primary alcohol is oxidized to the aldehyde 106 in Swern oxidation reaction. The aldehyde 106 was then condensed with ethylamine using a reductive alkylation reaction that gave 107. The latter was coupled with mesoporphyrin IX using amide forming procedures and the resulting 108 was deprotected in acid to 109 (SL-11184).

Scheme 27 illustrates on the preparation of a porphyrin-polyamine conjugate, where an amine group tethers the polyamine to the porphyrin. The amide derivative 111 was prepared as described above and was then reduced using metal hydrides and deprotected to yield 112. The synthesis of the porphyrin-polyamine 112 could also be achieved as shown in the Scheme 28. Reduction of the diester of mesoporphyrin IX under controlled conditions gave the dialdehyde 113. Reductive alkylation of 100 with 113 followed by deprotection also gave 112 (SL-11202).

Example 1

Synthesis Of Polyamine Compounds

Compound 2: NaH (80%, 1.08 g, 36 mmol) was added to a solution of amide 1 (6.81 g, 30 mmol) in DMF (50 ml) in an ice-water bath under $N_2$. The mixture was stirred for 1 h and a solution of 4-bromobutyronitrile (4.88 g, 33 mmol) in DMF (10 ml) was added in portions. The mixture was stirred over night at 75° C. The solvent was distilled off, the residue taken up in chloroform washed with a saturated solution of ammonium chloride, dried ($Na_2SO_4$) and evaporated. The residue was purifid by flash chromatography on silica gel (hexane/ethyl acetate 3:1) to yield 8.0 g (90%) of 2 as a colorless oil. $^1$H-NMR (CDCl$_3$) δ 1.05 (t, 3H), 1.90 (m, 2H), 2.30 (b, m, 5H), 2.60 (s, 6H), 3.20 (q, 2H), 3.35 (t, 2H), 6.95 (s, 2H); $^{13}$C-NMR (CDCl$_3$): δ 12.50, 20.61, 22.43, 23.60, 31.05, 36.12, 40.39, 43.78, 118.62, 131.79, 132.67, 139.71, 142.41. MS-EI (m/z) 294 (M$^+$).

Compound 4: Nitrile 2 (7.8 g, 27 mmol) was dissolved in a mixture of ethanol (150 ml) and concentrated hydrochloric acid (1.5 ml). PtO$_2$ was added (700 mg) and the mixture was hydrogenated at 50 psi over night. The catalyst was filtered off and the solvent evaporated. The residue (78 g, 98%) was used in the next step without further purification. The free base gave $^1$H-NMR (CDCl$_3$) δ 1.00 (t, 3H), 1.55 (m, 4H), 2.25 (s, 3H), 2.80 (t, 2H), 3.20 (m, 4H), 6.95 (s, 2H); $^{13}$C-NMR (CDCl$_3$): δ 12.54, 20.69, 22.53, 24.72, 27.65, 39.92, 40.29, 44.59, 131.71, 133.21, 139.82, 142.09. FAB-MS (m/z) 299 (M$^+$+1). Mesitylenesulfonyl chloride (8.8 g, 40.5 mmol) in dioxane (30 ml) was added dropwise to a stirred mixture of compound 3 (7.8 g, 27 mmol) dissolved in dioxane (60 ml) and 50% KOH (30 ml) at 0° C. The reaction mixture was allowed to reach 20° C. and then kept over night. An excess of water was added and the mixture was extracted with chloroform, dried ($Na_2SO_4$) and evaporated. The oily residue was crystallized from ethyl acetate/hexane yielding 4; 10.9 g (82%); mp 71.5–72° C. $^1$H-NMR (CDCl$_3$) δ 1.00 (t, 3H), 1.10–1.50 (m, 4H), 2.30 (s, 6H), 2.55, 2.60 (s, 12H), 2.85 (q, 2H), 3.15 (m, 4H), 4.70 (t, 1H), 6.95, 7.00 (s, 4H); $^{13}$C-NMR (CDCl$_3$): δ 12.70, 20.92, 21.04, 22.73, 22.92, 24.58, 26.68, 40.04, 42.02, 44.42, 131.91, 133.31, 133.64, 138.99, 140.05, 142.15, 142.35. MS-FAB (m/z) 480 (M$^+$).

Compound 5: (E)-2-Butene-1,4-diyl bis[mesitylenesulfonate]: (E)-2-Butene-1,4-diol (1.76 g, 20 mmol), and benzyltriethylammonium bromide (270 mg, 1 mmol) were dissolved in 30 ml of a 50% potassium hydroxide solution and 30 ml of dioxane. The mixture was stirred at 5° C. and mesitylenesulfonyl chloride (8.72 g, 40 mmol) dissolved in 30 ml of dioxane was added dropwise. When the addition was over, stirring was continued for 1 h, water was then added, and the white precipitate was filtered and crystallized from chloroform-hexane to yield 5; 7.0 g (77%); mp 119–120° C. $^1$H-NMR (CDCl$^3$): δ 2.35 (s, 6H), 2.60 (s, 12H), 4.45 (d, 4H), 5.75 (b, 2H), 6.95 (s, 4H); $^{13}$C-NMR (CDCl$_3$): δ 20.96, 22.52, 67.96, 127.67, 131.69, 131.74, 139.79, 143.45. MS-EI (m/z), 452 (M$^+$), 253, 200, 183. Anal. Calcd for $C_{22}H_{28}O_6S_2$: C, 58.40; H, 6.19. Found: C, 58.35; H, 6.22.

Compound 6 was synthesized from 5 according to a procedure described elsewhere (Reddy et al., *J. Med. Chem.* 41:4723 (1998)) in 56% yield. $^1$H-NMR (CDCl$_3$): δ 0.95 (t, J=7.15 Hz, 6H, CH$_3$), 1.34 (m, 8H, CH$_2$), 2.29 (s, 12H, CH$_3$), 2.55 (s, 24H, CH$_3$), 3.09 (m, 12H, NCH$_2$), 3.72 (d, J=4.53 Hz, 4H, NCH$_2$), 5.48 (t, J=4.31 Hz, 2H, CH═CH), 6.92 (s, 4H, Ph), 6.93 (s, 4H, Ph); $^{13}$C-NMR (CDCl$_3$): δ 12.71, 20.90, 22.71, 22.76, 24.74, 40.04, 42.21, 44.56, 45.69, 128.45, 131.88, 132.02, 140.05, 140.16, 142.20, 142.58. MS-FAB (m/z) 1012.8 (M$^+$, 100%), 828.7, 646.7, 561, 176.

Compound 7 was obtained from 6 as described elsewhere (Reddy et al., *J. Med. Chem.* 41:4723 (1998)) in 75% yield, mp>230° C. $^1$H-NMR (D$_2$O): δ 1.26 (t, J=12.5 Hz, 6H, 2CH$_3$), 1.79 (m, 8H, CH$_2$), 3.12 (m, 12H, NCH$_2$), 3.80 (d, J=7.16, 4H, NCH$_2$), 6.10 (m, 2H, CH═CH); $^{13}$C-NMR (D$_2$O): δ 12.79, 25.10, 45.19, 48.53, 48.62, 50.36, 130.66. MS-MALDI (m/z): 285.3 (MH$^+$, 100%).

Compound 8 was obtained from the commercially available butyne diol. Mesitylenesulfonyl chloride (19.5 g, 90 mmol) in dioxane (30 ml) was added dropwise to a stirred and cooled mixture of butyne diol (2.58 g, 30 mmol), 50% potassium hydroxide (30 ml) and triethylbenzyne ammonium bromide (405 mg, 1.5 mmol). Once the addition was over, the mixture was stirred at room temperature for an additional 3 h. An excess of water was added and the white precipitate was cooled over night, filtered off and dried. Recrystallization from ethyl acetate/hexane afforded 8.6 g (63%) of 8; mp 105–106° C.

$^1$H-NMR (CDCl$_3$): δ 2.30 (s, 6H), 2.60 (s, 12H), 4.50 (s, 4H), 6.95 (s, 4H); $^{13}$C-NMR (CDCl3): δ 20.93, 22.48, 56.13, 80.41, 130.65, 131.67, 139.98, 143.67. MS-EI (m/z) 450 (M$^+$).

Compound 9 was obtained following a procedure analogous to that described for compound 42 (see below). From 450 mg (1 mmol) of diester 8 and 1.05 g (2.2 mmol) of diamide 4, 570 mg (56%) of tetramide 9 was obtained. $^1$H-NMR (CDCl$_3$): δ 0.90 (t, 6H), 1.30 (bs, 8H), 2.20 (s, 12H), 2.45 (s, 24H), 3.05 (m, 12H), 3.75 (s, 4H), 6.87 (s, 8H); $^{13}$C-NMR (CDCl$_3$): δ 12.70, 20.78, 22.68, 34.65, 39.97, 44.46, 44.99, 78.62, 131.85, 131.98, 132.34, 140.14, 142.13, 142.55. MS-FAB (m/z) 1010 (M$^\oplus$).

Compound 10 was obtained following a procedure analogous to that described for compound 43 (see below). From 500 mg (0.49 mmol) of tetramide 9, 160 mg (76%) of the tetrahydrochloride 25 was obtained; mp>280° C. (decomp). $^1$H-NMR (D$_2$O): δ 1.30 (t, 6H), 1.80 (b, 8H), 2.90–3.25 (m, 12H), 4.05 (s, 4H); $^{13}$C-NMR (D$_2$O): δ 13.39, 25.64, 39.26, 45.72, 49.00, 49.20, 81.20. MS-MALDI 283 (M$^+$+1).

Compound 11: Mesitylenesulfonylethylamide 1 (3.1 g, 13.65 mmol) was dissolved in anhydrous DMF (30 ml) followed by the addition of NaH (85%, 0.423 g) in several portions. The mixture was stirred at room temperature for 1 h. N-(4-chloro-2-butenyl)-phthalimide (Aldrich, 3.06 g, 13 mmol) in 20 ml of DMF was added to the flask followed by stirring at 80° C. over night. The mixture was cooled to room temperature, quenched with H$_2$O (10 ml), and the solution was evaporated to dryness in vacuo. The solid residue was partitioned between 25 ml H$_2$O and 25 CHCl$_3$. The aqueous layer was extracted with CHCl$_3$ (3×25 ml), the organic layers were washed with brine (35 ml), dried (MgSO$_4$), the solvent was evaporated to afford a gum which solidified upon trituration with hexane to give 11. The $^1$H-NMR and $^{13}$C-NMR spectra showed that 11 was pure enough to be used in the next step without further purification, yield 4.75 g. $^1$H-NMR (CDCl$_3$): δ 1.16 (t, J=7.11 Hz, 3H, CH$_3$), 2.29 (s, 3H, CH$_3$), 2.63 (s, 6H, 2CH$_3$), 3.29 (q, J=7.11 Hz, 2H, CH$_2$), 4.06 (d, J=5.24 Hz, 2H, NCH$_2$), 4.26 (d, J=5.72 Hz, 2H, NCH$_2$), 5.59 (m, 2H, CH=CH), 6.95 (s, 2H, Ph), 7.71 (m, 2H, Ph), 7.83 (m, 2H, Ph); $^{13}$C-NMR (CDCl$_3$): δ 13.06, 20.89, 22.72, 34.35, 40.68, 42.01, 123.27, 126.69, 129.47, 131.90, 134.00, 140.24.

Compound 12: Amide 11 (20 g, 46.95 mmol) was dissolved in methanol, hydrazine monohydrate (5 ml, 98.52 mmol) was added and the solution stirred at 55° C. for 24 h. Initially it was a homogeneous solution; however, after several hours a white solid precipitated. The mixture was cooled to room temperature, 300 ml of conc. HCl were added slowly (exothermic reaction), and stirring at room temperature was continued for 12 h more. Methanol was evaporated, and the resulting solid was extracted with CHCl$_3$ (3×150 ml). The aqueous layer was neutralized with 50% NaOH, extracted again with CHCl$_3$ (3×100 ml), the combined organic layers were dried (MgSO$_4$); the solution was evaporated to afford a gum, which solidified under high vacuum to give 12; yield 9.0 g (65%). The compound was purified by column chromatography using hexane, ethyl acetate (7:3) as eluent; mp 167–169° C. $^1$H-NMR (CDCl$_3$): δ 1.0 (t, J=7.1 Hz, 3H, CH$_3$), 2.28 (s, 3H, CH$_3$), 2.56 (s, 6H, 2CH$_3$), 2.62 (br, NH$_2$), 3.12 (q, J=7.1 Hz, 2H, NCH$_2$), 3.73 (br, 2H, NCH$_2$), 3.94 (d, J=6.0 Hz, 2H, NCH$_2$), 5.80 (m, 2H, CH=CH), 6.92 (s, 2H, Ph); $^{13}$C-NMR (CDCl$_3$): δ 12.97, 20.93, 22.74, 36.43, 40.94, 42.08, 124.29, 131.89, 132.00, 132.62, 140.21, 142.67.

Compound 13 was obtained from 12 as described for 4 in 96% yield. It was purified by column chromatography using hexane and ethyl acetate (4:1.5) as eluants; mp 98–99° C.;

$^1$H-NMR (CDCl$_3$): δ 0.93 (t, J=5.85 Hz, 3H, CH$_3$), 2.23 (s, 3H, CH$_3$), 2.24 (s, 3H, CH$_3$), 2.50 (s, 6H, 2CH$_3$), 2.56 (s, 6H, 2CH$_3$), 3.06 (q, J=7.15 Hz, 2H, NCH$_2$), 3.48 (t, J=5.99 Hz, 2H, NCH$_2$), 3.68 (d, J=5.72 Hz, 2H, NCH$_2$), 4.58 (t, J=6.24 Hz, 1H, NH), 5.44 (m, 2H, CH=CH), 6.87 (s, 2H, Ph), 6.89 (s, 2H, Ph); $^{13}$C-NMR (CDCl$_3$): δ 12.80, 20.89, 22.64, 22.89, 39.01, 40.59, 41.41, 128.14, 128.46, 131.91, 131.96, 139.08, 140.19, 142.26, 142.54. MS-FAB (m/z) 479.2 (M$^+$, 65%), 296.2, 279.1, 267.2, 183.1.

Compound 15: Amide 13 (4.79 g, 10 mmol) was dissolved in anhydrous DMF (40 ml) followed by addition of NaH (0.37 g) in several portions, the mixture stirred at room temperature for 2 h, cis-1,4-dichloro-2-butene (7.5 g, 60 mmol) in 10 ml DMF was added at once, and stirring was continued at 50° C. over night. The mixture was cooled to room temperature, quenched with 10 ml H$_2$O, the solvents were evaporated, and the contents were partitioned between H$_2$O (50 ml) and CHCl$_3$ (50 ml). The aqueous layer was extracted with CHCl$_3$ (3×50 ml), the pooled organic layers were dried (MgSO$_4$), evaporated, and 15 was purified by column chromatography using hexane, ethyl acetate (8.5:1.5) as eluants; yield 5.5 g (97%), mp 106–108° C. $^1$H-NMR (CDCl$_3$): δ 1.03 (t, J=7.33 Hz, 3H, CH$_3$), 2.30 (s, 6H, 2CH$_3$), 2.57 (s, 12H, 4CH$_3$), 3.17 (q, 7.31 Hz, NCH$_2$), 3.71 (m, 4H, NCH$_2$), 3.81 (d, J=6.87 Hz, 2H, NCH$_2$), 3.95 (d, J=7.70 Hz, 2H, CHCl$_2$), 5.50 (m, 3H, CH=CH), 5.74 (m, 1H, CH=CH), 6.93 (s, 2H, Ph), 6.95 (s, 2H, Ph); $^{13}$C-NMR (CDCl$_3$): δ 12.91, 22.70, 22.74, 38.20, 40.45, 41.60, 42.11, 42.33, 128.17, 128.95, 129.34, 129.40, 131.94, 132.08, 140.23, 140.34, 142.91. MS-FAB (m/z) 566.7 (M$^+$, 100%), 153.4, 96.3.

Compound 14 was prepared from 13 and 1,4-diiodobutane as described above for 15. The product was purified by column chromatography using hexanes and ethyl acetate (4:1) as eluant; yield 79%. $^1$H-NMR (CDCl$_3$): δ 1.04 (t, J=7.10 Hz, 3H, CH$_3$), 1.63 (m, 4H, CH$_2$), 2.30 (s, 6H, 2CH$_3$), 2.58 (s, 12H, 4CH$_3$), 3.04 (t, J=6.50 Hz, 2H, CH$_2$I), 3.16 (m, 4H, NCH$_2$), 3.78 (d, J=5.14 Hz, 4H, NCH$_2$), 5.55 (m, 2H, CH=CH), 6.94 (s, 2H, Ph), 6.95 (s, 2H, Ph); $^{13}$C-NMR (CDCl$_3$): δ 5.69, 12.92, 20.95, 22.72, 22.78, 28.25, 30.36, 40.47, 41.59, 42.11, 44.71, 128.34, 129.00, 131.94, 132.06, 132.60, 132.89, 140.15, 140.21, 142.50, 142.71.

Compound 16 was prepared from 4 and 4-bromobutyronitrile as described above for Compound 2 in 94% yield. $^1$H NMR (CDCl$_3$): δ 0.97 (t, J=7.12 Hz, 3H, CH$_3$), 1.40 (m, 4H, 2CH$_2$), 1.85 (Pent., m, 2H, CH$_2$), 2.27 (t, J=7.17 Hz, 2H CH$_2$CN), 2.30 (s, 6H, 2CH$_3$), 2.57 (s, 6H, 2CH$_3$), 2.58 (s, 6H, 2CH$_3$), 3.13 (m, 6H, NCH$_2$), 3.28 (t, J=7.11 Hz, 2H, NCH$_2$), 6.94 (s, 2H, Ph), 6.96 (s, 2H, Ph); $^{13}$C NMR (CDCl$_3$): δ 12.55, 14.54, 20.84, 22.64, 22.73, 23.65, 24.43, 24.57, 39.88, 44.31, 44.54, 45.58, 118.69, 131.84, 132.05, 132.73, 133.36, 139.94, 142.20, 142.71.

Compound 17 was prepared from 16 as described above for Compound 3 in 93% yield.

$^1$H NMR (CDCl$_3$): δ 1.00 (t, J=6.92 Hz, 3H, CH$_3$), 1.40 (m, 10H, 4CH$_2$, NH$_2$), 2.29 (s, 6H, 2CH$_3$), 2.57 (b, 14H, 4CH$_3$, CH$_2$N), 3.13 (m, 8H, 4CH$_2$N), 6.93 (s, 4H, 2 Ph); $^{13}$C NMR (CDCl$_3$): 12.72, 20.90, 22.72, 22.78, 24.67, 24.80, 30.80, 40.02, 41.61, 44.56, 45.10, 45.38, 131.87, 140.04, 142.21, 142.28; MS-FAB(M/Z) 552.3(M$^+$, 100%), 368.2, 299.1, 183.0, 154.0.

Compound 18 was prepared from 17 as described above for Compound 4.

$^1$H NMR (CDCl$_3$): δ 0.96 (t, J=7.13 Hz, 3H, CH$_3$), 1.38 (m, 8H, 4CH$_2$), 2.29 (s, 9H, 3CH$_3$), 2.55 (s, 6H, 2CH$_3$), 2.56 (s, 6H, 2CH$_3$); 2.59 (s, 6H, 2CH$_3$), 2.80 (m, 2H, CH$_2$N), 3.10 (m, 8H, NCH$_2$), 4.67(t, J=6.6 Hz, 1H, NH), 6.93 (s, 6H, 3 Ph); $^{13}$C NMR (CDCl$_3$): δ 12.56, 20.87, 22.70, 22.74, 22.84, 24.40, 26.45, 24.67, 26.62, 39.87, 41.88, 44.45, 45.02, 45.09, 131.86, 131.90, 131.92, 133.12, 133.32, 133.68, 138.91, 139.97, 142.02, 142.21, 142.38; MS-FAB(M/Z): 756.9(M+23(Na), 100%) 572.8, 390.7, 333.6, 305.6

Compound 19 was prepared from 4 and 1,4-dichloro-2-butene as described above for 15 in 99% yield. $^1$H-NMR (CDCl$_3$): δ 1.01 (t, J=7.11 Hz, 3H, CH$_3$), 1.38 (m, 4H, CH$_2$), 2.29 (s,3H), 2.30 (s,3H), 2.57 (s, 6H), 2.61 (s, 6H), 3.11 (m, 4H, NCH$_2$), 3.16 (q, J=7.15 Hz, 2H, NCH$_2$), 3.81 (d, J=7.17 Hz, 2H, NCH$_2$), 3.98 (d, J=8.05 Hz, 2H, CH$_2$Cl), 5.51 (m, 1H, CH=CH), 5.77 (m, 1H, CH—CH), 6.93 (s, 2H, Ph), 6.95 (s, 2H, Ph); $^{13}$C-NMR (CDCl$_3$): δ 12.76, 20.91, 22.71, 22.76, 24.74, 38.12, 40.08, 41.85, 44.59, 45.54, 129.14, 129.25, 131.88, 132.02, 140.09, 140.19, 142.21, 142.63. MS-FAB (m/z) 569.3 (M$^+$, 20%), 385.2, 240.1, 203.3, 183.0, 119 (100%).

Compound 20 was prepared from 18 and 15 following the procedure described above for 15. It was purified by column chromatography using hexanes-ethyl acetate (7:3) as eluant (78% yield). $^1$H-NMR (CDCl$_3$): δ 0.97 (t, J=7.10 Hz, 3H, CH$_3$), 0.99 (t, J=7.0 Hz, 3H, CH$_3$), 1.29 (m, 8H, CH$_2$), 2.29 (s, 15H, CH$_3$), 2.54, 2.55, 2.59 (s, 30H, CH$_3$), 3.06 (m, 12H, NCH$_2$), 3.65 (m, 8H, NCH$_2$), 5.48 (m, 4H, CH=CH), 6.92 (s, 1OH, Ph); $^{13}$C-NMR (CDCl$_3$): δ 12.70, 12.83, 20.88, 20.91, 22.65, 22.68, 22.72, 22.74, 24.48, 24.72, 40.04, 40.47, 41.53, 42.07, 42.22, 42.34, 44.54, 44.96, 127.94, 128.27, 128.57, 129.20, 131.92, 132.05, 139.96, 140.00, 140.12, 140.16, 140.27, 142.19, 142.25, 142.47, 142.58, 142.87. MS-FAB (m/z) 1263.81 (M$^+$, 100%), 1080.01, 898.11, 714.81, 563.

Compound 21: Pentamide 20 (0.93 g, 0.735 mmol) was dissolved in 20 ml anhydrous CH$_2$Cl$_2$, phenol (3.46 g, 36.77 mmol) was added, followed by HBr in acetic acid (30%, 17.62 ml) and the mixture was stirred over night at 25° C. Water (10 ml) was added to the flask, the aqueous layer was separated, the organic layer was extracted with 5 ml H$_2$O, and the combined aqueous layers were washed with CH$_2$Cl$_2$ (6×15 ml). Water was evaporated under vacuum to afford a solid which was dissolved in 1 ml 1N NaOH followed by 1 ml of 50% KOH. This solution was extracted with CHCl$_3$ (10×5 ml). The combined organic layers were dried (MgSO$_4$), CHCl$_3$ was evaporated, and the residue dissolved in anhydrous diethyl ether. Anhydrous HCl gas was passed into the solution while cooling at 0° C. A white solid precipitated which was filtered and washed with ether. It was 21 (84%). $^1$H-NMR (D$_2$O): δ 1.29 (t, J=7.32 Hz, 3H, CH$_3$), 1.31 (t, J=7.24 Hz, 3H, CH$_3$), 1.79 (m, 8H, CH$_2$), 3.12 (m, 12H, NCH$_2$), 3.87 (m, 8H, NCH$_2$), 5.98 (m, 4H, CH=CH); $^{13}$C-NMR (D$_2$O): δ 13.36, 13.46, 25.66, 25.77, 45.44, 45.74, 46.24, 46.41, 46.84, 49.09, 49.41, 49.70, 129.02, 129.16, 129.47, 129.66. MS-MALDI (m/z) 354.36 (MH$^+$, 100%).

Compound 22 was prepared in 51% yield from 18 and 14 as described above for compound 15. $^1$H-NMR (CDCl$_3$): δ 0.97 (t, J=6.59 H, 3H, CH$_3$), 0.99 (t, J=7.02 Hz, 3H, CH$_3$), 1.29 (m, 12H, CH$_2$), 2.29 (s, 15H, CH$_3$), 2.55 (s), 2.56 (s), 2.57 (s), 3.10 (m, 16H, NCH$_2$), 3.70 (m, 4H, NCH$_2$), 5.47 (m, 2H, CH=CH), 6.93 (s, 10H, Ph); $^{13}$C-NMR (CDCl$_3$): δ 12.69, 12.83, 20.91, 22.69, 22.71, 22.76, 24.43, 24.70, 40.48, 41.11, 41.48, 44.50, 44.91, 128.13, 128.90, 131.88, 131.94, 132.01, 133.29, 139.95, 140.00, 140.15, 142.22, 142.29, 142.60. MS-FAB (m/z) 1265.91 (M$^+$, 100%), 1082.01, 900.11, 716.91, 563.81.

Compound 23 was prepared from 22 in 79% yield as described above for 21. $^1$H-NMR (D$_2$O): δ 1.29 (t, J=7.29 Hz, 3H, CH$_3$), 1.30 (t, J=7.30 Hz, 3H, CH$_3$), 1.78 (m, 12H, CH$_2$), 3.12 (m, 16H, NCH$_2$), 3.83 (m, 4H, NCH$_2$), 5.96 (m, 2H, CH=CH); $^{13}$C-NMR (D$_2$O): δ 13.31, 13.42, 25.62, 25.75, 45.38, 45.71, 46.18, 46.76, 49.07, 49.32, 49.69, 129.11, 129.39. MS-MALDI (m/z) 356.38 (MH$^+$, 100%).

Compound 24 was prepared from 18 (52% yield) as described. $^1$H-NMR (CDCl$_3$): δ 0.95 (m, 6H, 2CH$_3$), 1.32 (m, 12H, CH$_2$), 2.29 (s, 15H, CH$_3$), 2.55 (s, 30H, CH$_3$), 3.06 (m, 16H, NCH$_2$), 3.70 (m, 4H, NCH$_2$), 5.47 (m, 2H, CH=CH), 6.92 (s, 10H, Ph); $^{13}$C-NMR (CDCl$_3$): δ 12.67, 20.90, 22.71, 22.76, 24.43, 24.68, 39.97, 42.08, 44.48, 44.90, 45.61, 128.28, 128.45, 131.87, 131.93, 132.01, 139.96, 140.00, 140.12, 142.21, 142.28, 142.58. MS-FAB (m/z) 1265.91 (M$^+$, 100%), 1082.01, 900.11.

Compound 25 was prepared from 24 in 96% yield as described above for 21. $^1$H-NMR (D$_2$O): δ 1.28 (t, J-7.29 Hz, 6H, 2CH$_3$), 1.78 (m, 12H, CH$_2$), 3.09 (m, 16H, NCH$_2$), 3.84 (m, 4H, NCH$_2$), 5.96 (m, 2H, CH=CH); $^{13}$C-NMR (D$_2$O): δ 13.31, 25.61, 25.73, 45.70, 46.79, 49.05, 49.36, 49.65, 129.19. MS-MALDI (m/z) 356.4 (MH$^+$).

Compound 26: A mixture of KOH (0.25 g), K$_2$CO$_3$ (0.25 g) and tetra-n-butyl-ammonium hydrogen bromide (0.05 g) were suspended in 15 ml benzene. Mesitylenesulfonylamide (0.199 g, 1 mmol) was added to the suspension and the mixture was heated to 50° C. Iodide 14 (1.98 g, 3 mmol) in 10 ml benzene was added to the flask, the mixture heated under reflux over night, then cooled to room temperature; the inorganic solids were filtered off and washed with benzene (2×20 ml). The combined organic layers were washed several times with water until the washings were neutral. The benzene was dried (MgSO$_4$), evaporated and the residue purified by column chromatography using hexanes and ethyl acetate (7.5:2.5) as eluant; 25% yield (0.948 g).

$^1$H-NMR (CDCl$_3$): δ 1.00 (t, J=7.18 Hz, 6H, CH$_3$), 1.28 (m, 8H, CH$_2$), 2.29 (s, 15H, CH$_3$), 2.53 (s), 2.55 (s), 2.57 (s), 3.03 (m, 8H, NCH$_2$), 3.12 (q, J=7.13 Hz, 4H, NCH$_2$), 3.70 (m, 8H, NCH$_2$), 5.47 (m, 4H, CH=CH), 6.93 (s, 10H, Ph); $^{13}$C-NMR (CDCl$_3$): δ 12.78, 20.85, 22.63, 22.69, 24.32, 24.58, 40.41, 41.43, 42.00, 44.76, 45.43, 128.08, 128.83, 131.88, 131.95, 132.77, 132.85, 133.23, 139.90, 140.04, 140.08, 142.22, 142.43, 142.53. MS-FAB (m/z) 1263.81 (M$^+$, 100%), 1081, 898.11, 815.01, 561.81, 418.81.

Compound 27 was prepared from 26 in 57% yield as described above for 21. $^1$H-NMR (D$_2$O): δ 1.31 (t, J=7.31 Hz, 6H, CH$_3$), 1.78 (m, 8H, CH$_2$), 3.15 (m, 12H, NCH$_2$), 3.83 (m, 8H, NCH$_2$), 5.96 (m, 4H, CH=CH); $^{13}$C-NMR (CDCl$_3$): δ 13.43, 25.64, 25.76, 45.39, 46.19, 46.77, 49.35, 49.72, 129.11, 129.41. MS-MALDI (m/z) 354.3 (MH$^+$, 100%).

Compound 28 was prepared from 15 and mesitylenesulfonylamide in 24% yield as described above for 26; mp 57.7° C. $^{13}$H-NMR (CDCl$_3$): δ 0.99 (t, J=7.09 Hz, 6H, CH$_3$), 2.29 (s, 15H, CH$_3$), 2.53 (s), 2.55 (s), 3.12 (q, J=7.09 Hz, 4H, NCH₂), 3.63 (m, 16H), NCH₂), 5.49 (m, 8H, CH=CH), 6.93 (s, 10H, Ph); $^{13}$C-NMR (CDCl₃): δ 12.85, 20.89, 20.92, 22.66, 40.47, 41.53, 42.19, 128.00, 128.47, 128.58, 129.11, 131.92, 132.05, 140.17, 140.30, 142.46, 142.87. MS-FAB (m/z) 1259.81 (M⁺, 60%), 1075.91, 894.01, 306.51, 153.4 (100%).

Compound 29 was prepared from 28 in 81% yield as described above for 21. $^1$H-NMR (D₂O): δ 1.31 (t, J=7.29 Hz, 6H, CH₃), 3.15 (q, J=7.31 Hz, 4H, NCH₂), 3.84 (m, 4H, NCH₂), 3.90 (m, 12H, NCH₂), 5.98 (m, 8H, CH=CH); $^{13}$C-NMR (D₂O): δ 13.42, 45.41, 46.22, 46.44, 129.07, 129.37, 129.42, 129.58. MS-MALDI (m/z) 350.31 (MH⁺).

Compound 30 was prepared from 19 in 25% yield as described above for 26; mp 62.3° C.

$^1$H-NMR (CDCl₃): δ 0.95 (5, J=7.17 Hz, 6H, CH₃), 1.33 (m, 8H, CH₂), 2.29 (s, 15H, CH₃), 2.54 (s), 2.55 (s), 3.07 (m, 12H, NCH₂), 3.65 (m, 8H, NCH₂), 5.48 (m, 4H, CH=CH), 6.92 (s, 10H, Ph); $^{13}$C-NMR (CDCl₃): δ 12.69, 20.90, 22.69, 22.73, 24.70, 40.03, 42.13, 42.30, 44.53, 45.59, 128.11, 128.79, 131.87, 132.00, 140.02, 140.14, 140.28, 142.17, 142.58, 142.85. MS-FAB (m/z) 1263.81 (M⁺, 100%), 1080.01, 898.11, 714.01, 153.

Compound 31 was prepared from 30 in 87% yield as described above for 21. $^1$H-NMR (D₂O): δ 1.28 (t, J=7.32 Hz, 6H, CH₃), 1.79 (m, 8H, CH₂), 3.10 (m, 12H, NCH₂), 3.87 (m, 8H, NCH₂), 5.98 (m, 4H, CH=CH), $^{13}$C-NMR (D₂O): δ 12.70, 25.00, 25.13, 45.10, 45.81, 46.21, 48.44, 48.78, 128.44, 128.85. MS-MALDI (m/z) 354.3 (MH⁺).

Compound 32: Mesitylenesulfonylamide (1.47 g, 7.38 mmol) was dissolved in 50 ml anhydrous DMF, and NaH (85%, 0.3 g) was added to it under a nitrogen atmosphere. The mixture was stirred at room temperature and 19 (1.40 g, 2.46 mmol) in 25 ml DMF were added. Heating at 65° C. continued over night. The mixture was cooled to room temperature, and 10 ml of H₂O were added. The solvents were evaporated and the solid residue was partitioned between 40 ml H₂O and 40 ml CHCl₃. The aqueous layer was extracted with CHCl₃ (2×30 ml), the combined organic layers were washed with H₂O (3×50 ml), dried (MgSO₄), and evaporated. The residue was purified by column chromatography using hexanes-ethyl acetate (7.5:2.5). 1.7 g (97%) of 32 as a white solid was obtained. $^1$H-NMR (CDCl₃): δ 0.94 (t, J=7.10 Hz, 3H, CH₃), 1.30 (m, 4H, CH₂), 2.29 (s), 2.30 (s), 2.55 (s, 12H, CH₃), 2.65 (s, 6H, CH₃), 3.11 (m, 6H, NCH₂), 3.52 (m, 1H, NCH), 3.65 (m, 2H, NCH₂), 3.71 (m, 1H, NCH₂), 4.82 (br, 1H, NH), 5.47 (m, 2H, CH=CH), 6.93 (s, 4H, Ph), 6.96 (s, 2H, Ph); $^{13}$C-NMR (CDCl₃): δ 12.50, 20.91, 22.71, 22.76, 22.83, 22.91, 24.66, 38.98, 39.85, 42.15, 42.26, 44.50, 128.06, 128.51, 131.86, 131.91, 138.18, 140.00, 140.14, 140.28, 142.17, 142.65.

Compound 33 was prepared from 32 and 14 in 51% yield as described above for 22. $^1$H-NMR (CDCl₃): δ 0.99 (5, J=7.19 Hz, 6H, CH₃), 1.33 (m, 8H, CH₂), 2.29 (s, 15H, CH₃), 2.55 (s), 2.57 (s), 3.10 (m, 12H, NCH₂), 3.70 (m, 4H, NCH₂), 3.77 (m, 4H, NCH₂), 5.42 (m, 4H, CH=CH), 6.93 (s, 10H, Ph); $^{13}$C-NMR (CDCl₃): δ 12.70, 12.71, 20.89, 22.66, 22.72, 22.78, 22.81, 24.60, 26.53, 40.39, 41.37, 41.87, 42.20, 45.47, 128.26, 128.62, 131.78, 131.84, 131.86, 131.92, 132.77, 138.92, 139.96, 140.09, 140.17, 142.57, 142.63.

Compound 34 was prepared from 33 as described above for 21 in 40% yield.

Compound 35 was prepared from 15 in 94% yield as described above for 32.

Compound 36 was prepared from 35 and 14 in 82% yield as described above for 33. $^1$H-NMR (CDCl₃): δ 0.99 (t, J=7.11 Hz, 6H, CH₃), 1.33 (m, 4H, CH₂), 2.29 (s, 15H, CH₃), 2.55 (s), 2.57 (s), 3.07 (m, 8H, NCH₂), 3.70 (m, 12H, NCH₂), 5.46 (m, 6H, CH=CH), 6.92 (s, 10H, Ph); $^{13}$C-NMR (CDCl₃): δ 12.69, 12.80, 20.84, 22.62, 22.68, 22.73, 22.77, 24.58, 26.55, 40.44, 41.51, 41.86, 42.04, 42.24, 45.49, 128.10, 128.25, 128.52, 128.62, 128.82, 131.89, 131.95, 132.79, 138.89, 140.07, 140.14, 140.23, 141.94, 142.44, 142.53, 142.82. MS-FAB (m/z) 1262.8 (M⁺, 75%), 1080.01, 896, 119 (100%).

Compound 37 was prepared from 36 in 65% yield as described above for 21. $^1$H-NMR (D₂O): δ 1.31 (t, J=6.97 Hz, 6H, CH₃), 1.79 (m, 4H, CH₂), 3.12 (m, 8H, NCH₂), 3.83 (m, 12H, NCH₂), 5.96 (m, 6H, CH=CH); 13C-NMR (D₂O): δ 13.48, 25.69, 26.76, 41.67, 45.44, 46.24, 46.45, 46.80, 49.41, 129.00, 129.12, 129.45, 129.71. MS-MALDI (m/z) 352.3 (MH⁺).

Compound 38 was prepared from 35 and 19 in 89% yield as described. $^1$H-NMR (CDCl₃): δ 0.95 (m, 6H, CH₃), 1.33 (m, 4H, CH₂), 2.29 (s, 15H, CH₃), 2.54 (s), 2.55 (s), 2.57 (s), 3.09 (m, 8H, NCH₂), 3.66 (m, 12H, NCH₂), 5.48 (m, 6H, CH=CH), 6.93 (s, 10H, Ph); $^{13}$C-NMR (CDCl₃): δ 12.51, 12.63, 20.84, 20.86, 22.63, 22.65, 22.84, 24.61, 38.92, 40.40, 41.40, 42.11, 42.18, 44.44, 45.48, 127.95, 128.07, 128.49, 128.62, 128.80, 131.76, 131.83, 131.85, 131.88, 132.01, 138.05, 139.01, 140.07, 140.13, 140.24, 142.15, 142.21, 142.87. MS-FAB (m/z) 1263.1 (M⁺, 90%), 1080.1, 896.01, 119 (100%).

Compound 39 was prepared from 38 in 54% yield as described above for 21; mp 270° C. (dec.). $^1$H-NMR (D₂O): δ 1.31 (m, 6H, CH₃), 1.80 (m, 4H, CH₂), 3.10 (m, 8H, NCH₂), 3.86 (m, 12H, NCH₂), 5.98 (m, 6H, CH=CH); $^{13}$C-NMR (D₂O): δ 13.30, 13.42, 25.58, 25.70, 45.69, 46.21, 46.43, 46.81, 49.02, 49.37, 129.00, 129.15, 129.37, 129.59. MS-MALDI (m/z): 352.343 (MH⁺).

Compound 42: NaH (80%, 132 mg, 4.4 mmol) was added to a solution of diamide 41 (1.98 g, 4.4 mmol) in DMF (10 ml). The mixture was stirred at 20° C. for 30 minutes and a solution of the diester 40 (Reddy et al. (1998) J. Med Chem., 41:4723) (960 mg, 2 mmol) in DMF (10 ml) was added dropwise. The mixture was stirred at 75° C. for 2 h, the solvent was distilled off, the residue was taken in chloroform, washed with a saturated solution of ammonium chloride, dried (Na₂SO₄) and evaporated to dryness. The crude oil was purified by column chromatography using hexane-ethyl acetate (8:2) as running solvent. 1.4 g (70%) was obtained as a glassy oil. $^{13}$C-NMR (CDCl₃): δ 20.58, 22.63, 22.80, 32.42, 33.86, 43.16, 45.42, 46.26, 132.75, 133.21, 139.82, 142.40. MS-FAB 984 (M⁺), Compound 43: Phenol (1.86 g, 19.7 mmol) and 30% HBr in glacial acetic acid (35 ml) were added in that order to a solution of 42 (600 mg, 0.6 mmol) in CH₂Cl₂ (35 ml) at room temperature. The solution was stirred for 24 h, water (30 ml) was added, followed by extraction with methylene chloride (3×20 ml). The aqueous layer was evaporated under reduced pressure and the residue was taken up in 2N NaOH (2 ml) and then 50% KOH (2 ml) followed by extraction with chloroform (6×10 ml). After removal of chloroform, the residue was taken up in ethanol (15 ml) and acidified with concentrated hydrochloric acid (0.4 ml). The product 43 (230 mg, 93%) was recrystallized from aqueous ethanol; mp>270° C. (decomp). $^1$H-NMR (D₂O): δ 1.95 (m, 2H), 2.05–2.25 (m, 6H), 2.75 (s, 6H), 2.90 (b, 2H), 3.10–3.35 (m, 12H); $^{13}$C-NMR (D₂O): δ 25.21, 25.24, 35.60, 35.64, 47.41, 48.58, 50.87. MS-MALDI (m/z) 240 (M⁺+1).

Compound 47: NaH (80%, 132 mg, 4.4 mmol) was added to a solution of diamide 46 (1.98 g, 4.4 mmol) in DMF (10 ml). The mixture was stirred at 20° C. for 30 min and a solution of the diester 8 (900 mg, 2 mmol) in DMF (10 ml)

was added dropwise. The mixture was stirred at 75° C. for 2 h. The solvent was distilled off, the residue was taken up in chloroform, washed with a saturated solution of ammonium chloride, dried (NaSO$_4$) and evaporated to dryness. The oily residue was crystallized from ethyl acetate/hexane 1.2 g (61%); mp 165–166° C. $^1$H-NMR (CDCl$_3$): δ 1.08 (t, 3H), 1.75 (m 4H), 2.28 (s, 12H), 2.55 (bs, 24H), 3.10 (m, 12H), 3.98 (s, 4H), 6.95 (m, 8H); $^{13}$C-NMR (CDCl$_3$): δ 12.70, 20.86, 22.64, 25.14, 34.85, 40.22, 42.62, 43.37, 78.80, 131.99, 132.26, 133.21, 140.26, 142.28, 142.71. MS-FAB (m/z) 982 (M$^+$).

Compound 48 was obtained as described for 47. From 1.2 g (1.22 mmol) of tetramide 47, 420 mg (86%) of the tetrahydrochloride 48 was obtained; mp>270° C. (decomp). $^1$H-NMR (D$_2$O): δ 1.29 (t, 6H), 2.13 (m, 4H), 3.14 (m, 12H), 4.06 (s, 4H); $^{13}$C-NMR (D$_2$O): δ 13.34, 25.52, 39.45, 45.90, 45.64, 46.71, 81.32. MS-MALDI (m/z) 255 (M$^+$+1).

Compound 44 was obtained as described for 47. From 450 mg (1 mmol) of diester 8 and 994 mg (2.2 mmol) of diamide 41, 500 mg (52%) of the tetramide 44 was obtained and crystallized from ethyl acetate-hexane; mp 155–156° C.

Compound 45 was obtained as described for 43. From 500 mg (0.52 mmol) of tetramide 44, 160 mg (82%) of the tetrahydrochloride 45 was obtained; mp>270° C. (decomp). $^1$H-NMR (D$_2$O): δ 2.15 (m, 4H), 2.73 (s, 3H), 3.05–3.40 (m, 8H), 4.10 (s, 4H); $^{13}$C-NMR (D$_2$O): δ 25.59, 35.66, 45.90, 46.57, 48.61.

Compound 51 is a mixture of cis/trans-isomers. $^1$H-NMR (D$_2$O): δ 1.15–2.10 (m, 7H), 2.90 (q, 1H), 3.30–3.80 (b, 2H); $^{13}$-NMR (D$_2$O): δ 24.16, 24.97, 28.44, 30.42, 36.58, 37.14, 48.24, 52.27, 55.19, 57.45, 64.55, 67.26.

Compound 52: Mesitylenesulfonylchloride (6.5 g, 30 mmol) in dioxane (10 ml) was added dropwise to a stirred and cooled mixture of amine alcohol 51 (1.15 g, 10 mmol), triethylbenzyl ammonium bromide (135 mg, 0.5 mmol), 50% KOH (10 ml) and dioxane (10 ml). The reaction mixture was left over night at 20 ° C. with magnetic stirring. An excess of water was added, the solution was extracted with chloroform (3×30 ml), dried (Na$_2$SO$_4$) and evaporated to dryness. The oily residue was chromatographed on a silica-gel column using hexane:ethyl acetate (8:2) as eluants. Crystallization from ethyl acetate-hexane afforded 1.2 g (25%) of pure 52; mp 167–168° C. $^1$H-NMR (CDCl$_3$): δ 1.35–1.90 (6H), 1.90–2.15 (m, 1H), 2.30, 2.35 (s, 6H), 2.65 (s, 12H), 3.20 (m, 1H), 3.70 (m, 1H), 3.90 (m, 1H), 5.15 (d, 1H), 6.90, 7.00 (s, 4H); $^{13}$C-NMR (CDCl$_3$): δ 20.73, 20.85, 22.15, 22.37, 22.70, 26.94, 32.75, 45.34, 56.09, 70.38, 130.22, 131.57, 133.98, 138.68, 139.64, 142.02, 143.10. MS-EI (m/z) 479 (M$^+$), 280 (M$^⊕$–199).

Compound 54: NaH (105 mg, 3.5 mmol) was added to a solution of compound 52 (1.7 g, 3.5 mmol) in DMF (10 ml). The mixture was stirred at 20° C. for 30 min and a solution of compound 53 (1.34 g, 3.85 mmol) in DMF (5 ml) was added in small portions. The mixture was stirred at 75° C. for 2 h. The solvent was distilled off, the residue was taken up in chloroform, washed with a saturated solution of ammonium chloride, dried (Na$_2$SO$_4$) and evaporated. The oily residue was purified by column chromatography (hexane-ethyl acetate 8:2) which gave compound 54 (1.22 g, 47%). $^1$H-NMR (CDCl$_3$): δ 1.98 (t, 3H), 1.20–2.05 (9H), 2.20 (s, 6H), 2.55, 2.65 (s, 12H), 2.70–3.55 (9H), 6.85 (s, 4H); $^{13}$C-NMR (CDCl$_3$): δ 12.49, 20.80, 21.64, 21.87, 22.88, 28.72, 33.16, 36.13, 39.96, 43.80, 47.95, 57.77, 61.26, 131.83, 132.94, 133.14, 138.82, 139.90, 142.07, 142.63. MS-FAB (m/z) 628 (M$^+$+1), 546 (M$^+$–81).

Compound 55 was obtained following the procedure described for compound 42. From 1.22 g (1.6 mmol) of bromoderivative 54 and 820 mg (1.76 mmol) of diamide 46, 1.26 g (77%) of tetramide 55 was obtained as a glassy oil. $^1$H-NMR (CDCl$_3$): δ 0.80 (t, 6H), 1.20–1.75 (6H), 1.90 (m, 1H), 2.15 (s, 12H), 2.35–2.60 (s, 24H), 2.65–3.40 (15H), 6.85 (b, 8H); $^{13}$C-NMR (CDCl$_3$): δ 12.38, 20.71, 22.52, 22.66, 24.72, 27.55, 28.04, 39.19, 39.71, 41.02, 42.33, 42.62, 43.37, 48.81, 61.44, 131.76, 131.88, 133.10, 133.89, 138.66, 139.93, 142.17, 142.33, 142.57. MS-FAB (m/z) 1012 (M$^+$), 828 (M$^+$–184).

Compound 56 was obtained following the procedure described for compound 43. From 1.26 g (1.24 mmol) of tetramide 55, 300 mg (56%) of the tetrahydrochloride 56 was obtained; mp>270° C. (decomp). $^1$H-NMR (D$_2$O): δ 1.35 (t, 6H), 1.60 (m, 1H), 1.80 (b, 3H), 2.15 (b, 6H), 2.50 (b, 1H), 3.20 (m, 13H), 3.45 (m, 2H); $^{13}$C-NMR (D$_2$O): δ 13.23, 25.48, 25.73, 25.79, 31.69, 31.99, 43.40, 45.91, 46.43, 46.71, 48.07, 53.20, 75.28. MS-MALDI (m/z) 285 (M$^+$+1).

Compound 57: NaH (80%, 150 mg, 5 mmol) and NaBr (2.5 g, 25 mmol) were added to a solution of compound 52 (2.35 g, 4.9 mmol) in DMF (15 ml). The mixture was stirred at 20° C. for 30 min and a solution of 1-bromoethane (2.2 g, 25 mmol) in DMF (10 ml) was added in small portions. The mixture was stirred at 90° C. for 3 h. The solvent was distilled off, the residue taken up in chloroform, washed with a saturated solution of ammonium chloride, dried (Na$_2$SO$_4$) and evaporated. The product was purified by silica gel chromatography (hexane/ethyl acetate 9:1). The oily residue (1.5 g, 79%) crystallized on standing; mp 68–69° C. $^1$H-NMR (CDCl$_3$): δ 1.10 (t, 3H), 1.30–2.10 (6H), 2.25 (b, 4H), 2.60 (s, 6H), 3.20 (m, 2H), 3.35 (m, 2H), 3.60 (m, 2H), 6.95 (s, 2H); $^{13}$C-NMR (CDCl$_3$): δ 16.35, 20.93, 21.79, 22.89, 29.32, 29.37, 36.54, 38.12, 44.13, 61.40, 131.99, 132.80, 140.20, 142.52. MS-FAB 389 (M$^+$+1), 308 (M$^+$–80).

Compound 59 was obtained following the procedure described for compound 42. From 700 mg (1.80 mmol) of compound 57 and 394 mg (0.9 mmol) of diamide 58, 400 mg (37%) of tetramide 59 were obtained. $^1$H-NMR (CDCl$_3$): δ 0.90 (t,6H), 1.25–1.80 (m,8H), 1.80–2.10 (m,8H), 2.15 (s, 12H), 2.40, 2.50 (s, 24H), 2.60–3.35 (m,6H), 2.85, 2.90 (s, 8H); $^{13}$C-NMR (CDCl$_3$): δ 16.14, 20.85, 21.95, 21.99, 22.55, 25.49, 28.78, 28.88, 31.49, 37.87, 40.50, 40.83, 43.85, 44.06, 49.30, 61.42, 131.86, 131.96, 133.09, 133.40, 139.93, 139.98, 142.27, 142.40. MS-FAB (m/z) 1052 (M$^⊕$), 891 (M$^+$–184).

Compound 60 was obtained following the procedure described for compound 43. From 400 mg (0.38 mmol) of tetramide 59, 95 mg (53%) of the tetrahydrochloride derivative were obtained; mp>270° C. (decomp.) $^1$H-NMR (D$_2$O): δ 1.30 (t, 6H), 1.60 (m, 2H), 1.80 (m, 6H), 1.95–2.35 (6H), 2.45 (m, 2H), 3.20 (m, 10H), 3.40 (m, 4H); $^{13}$C-NMR (D$_2$O): δ 13.59, 25.34, 25.71, 31.75, 32.00, 43.34, 44.83, 48.02, 53.24, 64.52. MS-MALDI (m/z) 325 (M$^+$+1).

Compound 62: Mesitylenesulfonylchloride (3.27 g, 15 mmol) in dioxane (20 ml) was added dropwise to a stirred solution of 61 (1.3 g, 10 mmol) in dioxane (20 ml) and 50% KOH (15 ml) at 0° C. When addition was completed, the mixture was left over night at 20° C. Excess water was added, the solution cooled and the precipitate filtered off. Crystallization from ethylacetate-hexane gave compound 62 (2 g, 80%); mp 115–116° C.

$^1$H-NMR (CDCl$_3$): δ 2.35 (s, 3H), 2.55 (t, 2H), 2.65 (s, 6H), 3.25 (q, 2H), 5.15 (t, 1H), 7.0 (s, 2H); $^{13}$C-NMR (CDCl$_3$): δ 19.07, 20.82, 22.78, 38.37, 117.56, 132.07, 133.0, 138.99, 142.67. MS-EI (m/z) 252 (M$^+$).

Compound 63: NaH (80%, 330 mg, 11 mmol) was added to a solution of compound 62 (2.52 g, 10 mmol) in DMF (20 ml) under $N_2$. The mixture was stirred for 30 min and a solution of compound 53 (3.82 g, 11 mmol) in DMF (10 ml) was added in small portions. The mixture was stirred at 70° C. for 2 h. The solvent was distilled off, the residue taken up in chloroform, washed with a saturated solution of ammonium chloride, dried ($Na_2SO_4$) and evaporated to dryness. The product was purified by silica-gel chromatography (hexane-ethyl acetate 8:2). The oily residue (3.0 g, 57%) crystallized on standing; mp 105–106° C. $^1$H-NMR ($CDCl_3$): δ 1.00 (t, 3H), 1.75 (m, 2H), 2.35 (s, 6H), 2.60 (14H), 3.10 (m, 6H), 3.45 (t, 3H), 6.90, 6.95 (s, 4H); $^{13}$C-NMR ($CDCl_3$): δ 12.63, 16.94, 20.89, 22.67, 25.73, 40.27, 42.19, 42.51, 44.72, 117.36, 131.95, 132.22, 140.06, 140.34, 142.52, 143.33. MS-EI (m/z) 519 ($M^+$), 429 ($M^+$–HCN).

Compound 65: The nitrile 63 (3.0 g, 5.7 mmol) was dissolved in a mixture of ethanol (150 ml) and concentrated hydrochloric acid (1.5 ml). $PtO_2$ was added (300 mg), the mixture was hydrogenated at 50 psi over night, the catalyst was filtered off and the solvent evaporated to afford an oily residue of compound 64, which was used in the next step without further purification. Free base $^1$H-NMR ($CDCl_3$): δ 1.00 (t, 3H), 1.55 (m, 2H), 1.75 (m, 2H), 2.30 (s, 6H), 2.55 (14 H), 2.90–3.30 (8H), 6.95 (s, 4H); $^{13}$C-NMR ($CDCl_3$): δ 12.64, 20.87, 22.69, 25.35, 30.93, 39.04, 40.12, 42.65, 43.11, 131.86, 133.10, 140.04, 142.43. MS-FAB (m/z) 524 ($M^+$+1).

Mesitylenesulfonylchloride (1.86 g, 8.55 mmol) in dioxane (15 ml) was added dropwise to a stirred mixture of 64 (3.0 g, 5.7 mmol) dissolved in dioxane (30 ml) and 50% KOH (15 ml) at 0° C. The reaction mixture was allowed to reach room temperature and was kept for further 2 h. An excess of water was added and the mixture was extracted with chloroform, dried ($Na_2SO_4$) and evaporated to dryness. Purification was achieved by silica gel column chromatography using hexane-ethyl acetate (8:2) as eluant; 2.79 g (69%) of 65 were obtained. $^1$H-NMR ($CDCl_3$): δ 0.95 (t, 3H), 1.60 (m, 4H), 2.30 (s, 9H), 2.50 (s, 12H), 2.65 (s, 6H), 2.85 (m, 2H), 3.05 (6H), 3.20 (t, 2H), 5.00 (t, 1H), 6.95 (6H); $^{13}$C-NMR ($CDCl_3$): δ 12.45, 20.81, 22.73, 25.23, 27.46, 39.19, 33.99, 42.49, 42.92, 43.17, 131.84, 133.05, 133.82, 138.80, 139.90, 141.92, 142.36, 142.64. MS-FAB (m/z) 705 ($M^\oplus$).

Compound 66 was obtained following the procedure described for compound 42. From 705 mg (1 mmol) of 65 and 426 mg (1.1 mmol) of 57, 470 mg (46%) of tetramide 66 was obtained as a glassy product. $^1$H-NMR ($CDCl_3$): δ 0.85–1.10 (t, 6H), 1.35–2.10 (m,11H), 2.30 (s, 12H), 2.40–2.65 (m, 24H), 2.75–3.55 (m, 13H), 6.95 (m, 8H); $^{13}$C-NMR ($CDCl_3$): δ 12.64, 16.11, 20.91, 22.08, 22.75, 24.81, 25.09, 28.83, 29.07, 37.93, 40.08, 40.84, 42.50, 42.81, 43.11, 43.42, 49.11, 61.43. MS-FAB (m/z) 1013 ($M^+$+1).

Compound 67 was obtained following the procedure described for compound 43. From 470 mg (0.46 mmol) of tetramide 66, 142 mg (71%) of the tetrahydrochloride derivative was obtained; mp>250° C. (decomp.). $^1$H-NMR ($D_2O$): δ 1.30 (t, 6H), 1.60 (m, 1H), 1.85 (b,s, 3H), 2.15 (m, 6H), 2.45 (m, 1H), 3.15 (m, 13H), 3.45 (m, 2H); $^{13}$C-NMR ($D_2O$): δ 13.29, 13.57, 25.34, 25.44, 25.64, 31.68, 31.94, 43.27, 44.80, 45.86, 46.62, 47.42, 47.97, 53.19, 64.50. MS-MALDI 285 ($M^+$+1), 286 ($M^+$+2).

Compound 68a: 4-Cyanobenzaldehyde (Aldrich, 1.31 g, 10 mmol) was dissolved in 30 ml anhydrous MeOH followed by the addition of $MgSO_4$ (anhydrous, 1.5 g) and 1,4-diaminobutane (Aldrich, 0.44 g, 5 mmol) and the mixture was stirred under argon over night. The suspension was cooled in an ice bath and $NaBH_4$ (2.0 g) was added in portions and stirring continued for 2 h at 0° C. The methanol was evaporated under vacuum and the resulting solid was partitioned between 35 ml $H_2O$ and 50 ml $CHCl_3$. Some of the solid was not soluble in either the $H_2O$ or the $CHCl_3$ and was filtered off and the aqueous layer was extracted with $CHCl_3$ (2×25 ml). The pooled organic layers were dried ($MgSO_4$), evaporated and the solid was recrystallized from ethyl acetate-hexane, yield 1.1 g (35%); mp 90.6–90.8° C. $^1$H-NMR ($CDCl_3$): δ 1.43 (broad, 2H, NH), 1.55 (m, 4H, $CH_2$), 2.63 (m, 4H, $NCH_2$), 3.85 (s, 4H, benzylic $CH_2$), 7.44 (m, 4H, Ph), 7.60 (m, 4H, Ph); $^{13}$C-NMR ($CDCl_3$): δ 27.78, 49.28, 53.44, 110.65, 118.88, 128.52, 132.12, 146.21. MS (m/z) 318 ($M^+$), 185, 145, 131, 116 (100%), 70.

Compound 68b was prepared from 4-cyano-benzaldehyde and 1,5-diaminopentane as described above for 68a; 42% yield; mp 92.9–93.0° C. $^1$H-NMR ($CDCl_3$): δ 1.40 (m, 4H, NH, $CH_2$), 1.50 (m, 4H, $CH_2$), 2.59 (m, 4H, $NCH_2$), 3.83 (s, 4H, benzylic $CH_2$), 7.45 (m, 4H, Ph), 7.59 (m, 4H, Ph); $^{13}$C-NMR ($CDCl_3$): δ 24.86, 29.87, 49.29, 53.40, 110.50, 118.85, 128.48, 132.04, 146.19. MS (m/z) 332 ($M^+$), 216, 199, 145,116 (100%), 84.

Compound 68c was prepared from 4-cyanobenzyldehyde and 1,6-diaminohexane as described above for 68a; 45% yield; mp 95.6–95.8° C. $^1$H-NMR ($CDCl_3$): δ 1.35 (m, 4H, $CH_2$), 1.50 (m, 6H, NH, $CH_2$), 2.60 (t, J=6.92 Hz, 4H, $NCH_2$), 3.84 (s, 4H, benzylic $CH_2$), 7.44 (m, 4H, Ph), 7.60 (m, 4H, Ph); $^{13}$C-NMR ($CDCl_3$): δ 27.17, 30.02, 49.42, 53.50, 110.65, 118.92, 128.55, 132.14, 146.27. MS (m/z) 346 ($M^+$), 230, 213, 145, 116 (100%) 98.

Compound 69a: Dinitrile 68a (0.75 g, 2.36 mmol) was dissolved in anhydrous THF, lithium bis(trimethylsilyl)amide (9.43 ml of a 1 m solution in THF) was added slowly under argon atmosphere. The mixture was stirred at room temperature for 2 h; then cooled in an ice bath, followed by the addition of 4 equivalents of 6N HCl in ether. A white solid precipitated immediately and was filtered after 12 h. The solid was recrystallized from ethanol-ether to afford 1.19 g of compound 69a (93%). $^1$H-NMR ($D_2O$): δ 1.87 (m, 4H, $CH_2$), 3.22 (m, 4H, $CH_2N$), 4.40 (s, 4H, benzylic $CH_2$), 7.74 (m, 4H, Ph), 7.91 (m, 4H, Ph); $^{13}$C-NMR (DMSO-$d_6$): δ 22.68, 46.09, 49.28, 128.10, 128.47, 130.69, 138.15, 165.44. MS-ESI (m/z) 353.2 ($M^+$), 177.2 (100%).

Compound 69b was prepared from 68b in 92% yield as described above for 69a. $^1$H-NMR ($D_2O$): δ 1.52 (m, 2H, $CH_2$), 1.80 (m, 4H, $CH_2$), 3.19 (m, 4H, $NCH_2$); 4.40 (s, 4H), benzylic $CH_2$), 7.75 (m, 4H, Ph), 7.91 (m, 4H, Ph); $^{13}$C-NMR (DMSO-$d_6$): δ 24.90, 26.91, 48.96, 51.88, 130.29, 130.46, 132.43, 139.51, 167.52. MS-ESI (m/z) 367.2 ($M^+$), 350.2 (100%), 301.2.

Compound 69c was prepared from 68c as described above for 69a in 96% yield. $^1$H-NMR ($D_2O$): δ 1.46 (m, 4H, $CH_2$), 1.78 (m, 4H, $CH_2$), 3.16 (m, 4H, $NCH_2$), 4.39 (s, 4H), benzylic $CH_2$), 7.74 (m, 4H, Ph), 7.91 (m, 4H, Ph); $^{13}$C-NMR (DMSO-$d_6$): δ 25.24, 25.82, 46.73, 49.44, 128.35, 128.56, 130.81, 138.38, 165.58. MS-ESI (m/z) 381.2 ($M^+$), 191.2 (100%), 150, 116.

Compound 70: Triamide 18 (4.3 g, 5.8 mmol) was dissolved in 30 ml of DMF and 80% NaH (208 mg, 6.9 mmol) was added. The mixture was stirred under a $N_2$ atmosphere for 1 h and 1.12 g (7.5 mmol) of bromobutyronitrile dissolved in 3 ml of DMF were added all at once. The reaction mixture was heated for 3 h at 90° C. The solvent was distilled-off and the residue was dissolved in chloroform and washed twice with a saturated solution of ammonium chloride;

dried (NaSO$_4$) and evaporated to dryness. Flash chromatography of the residue using hexane-ethyl acetate (6:4) as eluant gave the yellow oil 70 (3.7 g, 77%). $^1$H-NMR (CDCl$_3$): δ 0.95 (t, 3H), 1.35 (m, 8H), 1.85 (m, 2H), 2.20 (t, 2H), 2.30 (s, 9H), 2.55 (s, 18H), 3.10 (m, 10H), 3.25 (t, 2H), 6.95 (s, 6H). MS-FAB (m/z) 823 (M$^+$+Na), 639, 457.

Compound 71: Nitrile 70 (3.7 g, 4.6 mmol) was dissolved in 20 ml of chloroform and 150 ml of ethanol were added. The mixture was reduced over 0.35 g of PtO$_2$ at 50 psi over night. The catalyst was filtered-off and the solvent evaporated to dryness. The oily residue was dried in vacuo for 2 h and dissolved in 50 ml of Cl$_3$CH and 12 ml 2N NaOH. The mixture was cooled in an icewater bath with efficient magnetic stirring and 1.50 g (6.9 mmol) of mesitylene chloride dissolved in 10 ml of chloroform were added all at once. After 2 h the organic layer was separated, washed twice with a saturated solution of amonium chloride, dried (NaSO$_4$) and evaporated to dryness. Flash chromatography of the residue using hexane-ethyl acetate (7:3) as eluant provided the tetramide 71 as a colorless oil (3.3 g, 73% over two steps). $^1$H-NMR (CDCl$_3$): δ 0.95 (t, 3H), 1.40 (m, 12H), 2.30 (s, 12H), 2.60 (s, 24H), 2.80 (b, 2H), 3.10 (m, 12H), 4.70 (b, 1H), 6.90 (s, 8H). MS-FAB (m/z) 1010 (M$^+$+1+Na), 826, 643.

Compound 72: The tetramide 71 (6.28 g, 6.3 mmol) was dissolved in 40 ml of DMF and 80% NaH (230 mg, 7.6 mmol) was added. The mixture was stirred under a N$_2$ atmosphere for 1 h and 1.30 g (8.8 mmol) of bromobutyronitrile dissolved in 3 ml of DMF were added all at once. The reaction mixture was heated for 3 h at 90° C., the solvent was distilled-off and the residue was extracted into chloroform and washed twice with a saturated solution of amonium chloride; dried (NaSO$_4$) and evaporated to dryness. Flash chromatography of the residue with hexane-ethyl acetate (7:3) as eluant provided the nitrile 72 (5.0 g, 74%). $^1$H-NMR (CDCl$_3$): δ 0.95 (t, 3H), 1.35 (m, 12H), 1.80 (m, 2H), 2.25 (t, 2H), 2.35 (s, 12H), 2.70 (s, 24H), 3.10 (m, 14H), 3.25 (t, 2H), 7.0 (s, 8H). MS-FAB (m/z) 1077 (M$^+$+1+Na), 893, 711,586.

Compound 73: Nitrile 72 (6.0 g, 5.6 mmol) was dissolved in 20 ml of chloroform and 150 ml of ethanol were added. The mixture was reduced over 600 mg of PtO$_2$ at 50 psi overnight. The catalyst was filtered-off and the solvent evaporated to dryness. The oily residue was dried in vacuo for 2 h and dissolved in 100 ml of chloroform and 15 ml 2N NaOH. The mixture was cooled in an icewater bath with efficient magnetic stirring, and 1.80 g (8.4 mmol) of mesitylene chloride dissolved in 10 ml of Cl$_3$CH was added all at once. After 2 h the organic layer was separated, washed twice with a saturated solution of amonium chloride, dried (Na$_2$SO$_4$) and evaporated to dryness. Flash chromatography of the residue using hexane-ethyl acetate (7:3) as eluant gave the pentamide 73 as a colorless oil (5.0 g, 71% over two steps). $^1$H-NMR (CDCl$_3$): δ 0.95 (t, 3H), 1.35 (m, 16H), 2.30 (s, 15H), 2.55 (s, 30H), 2.75 (bs, 2H), 3.05 (m, 16H), 4.70 (b, 1H), 6.90 (s, 10H). MS-FAB (m/z) 1261 (M$^+$-1+Na), 1077, 895.

Compound 74: Pentamide 73 (3.4 g, 2.7 mmol) was dissolved in 30 ml of DMF and 60% NaH (162 mg, 4.05 mmol) was added. The mixture was stirred under a N$_2$ atmosphere for 0.5 h and 2.3 g (10.8 mmol) of 2-bromoethanol benzylether dissolved in 3 ml of DMF were added all at once. The reaction mixture was heated for 2 h at 80° C., the solvent was distilled-off and the residue was dissolved in chloroform and washed twice with a saturated solution of amonium chloride, dried (NaSO$_4$) and evaporated to dryness. Flash chromatography of the residue using hexane-ethyl acetate (7:3) as eluant provided the product 74 (2.6 g, 70%). $^1$H-NMR (CDCl$_3$): δ 0.95 (t, 3H), 1.30 (m, 16H), 2.30 (s, 15H), 2.50 (s, 30H), 2.90–3.20 (m, 18H), 3.25 (t, 2H), 2.35 (t, 2H), 4.35 (s, 2H), 6.95 (s, 10H), 7.20–7.35 (m, 5H). $^{13}$C NMR (CDCl$_3$): δ 12.65, 20.84, 22.67, 22.71, 24.41, 24.66, 39.97, 44.48, 44.88, 46.59, 68.01, 72.95, 127.46, 127.57, 128.25, 131.83, 131.89, 133.28, 139.88, 139.95, 140.04, 142.16, 142.23. MS-FAB (m/z) 1394 (M$^+$-2+Na) 1030.

Compound 75: Pentamide 74 (1.2 g, 0.87 mmol) was dissolved in 12 ml of methylene chloride followed by the addition of 30% HBr/acetic acid (16 ml) and phenol (3.0 g, 32 mmol). The mixture was stirred at room temperature overnight, water (16 ml) was added, followed by extraction with methylene chloride (3×10 ml). The aqueous layer was evaporated in vacuo. The residue was dissolved in 2N NaOH (4 ml) and 50% KOH (4 ml) followed by extraction with chloroform (4×10 ml). After removal of the solvent the residue was dissolved in ethanol (20 ml) and acidified with concentrated hydrochloric acid (0.5 ml). The white precipitate (75) was recrystallized from aqueous ethanol (440 mg, 90%); mp above 270° C. (decomp). $^1$H-NMR (D$_2$O): δ 1.30 (t, 3H), 1.75 (b, 16H), 2.90–3.30 (m, 20H), 2.85 (t, 2H). $^{13}$C NMR (D$_2$O): δ 13.29, 25.48, 25.59, 45.70, 49.04, 49.49, 49.67, 51.88, 59.39. MS-MALDI (m/z) 374 (M$^+$+1).

Compound 76: Pentamide 73 (850 mg, 0.68 mmol) was dissovled in DMF (15 ml) and 80% NaH (30 mg, 1 mmol) was added. The mixture was stirred under a N$_2$ atmosphere at room temperature for 0.5 h and 137 mg (0.30 mmol) of 73 dissolved in 5 ml of DMF were slowly added. The reaction mixture was heated for 2 h at 80° C., the solvent was distilled-off and the residue was dissolved in chloroform and washed twice with a saturated solution of amonium chloride, dried (NaSO$_4$) and evaporated to dryness. Flash chromatography of the residue using hexane-ethyl acetate-methanol (6:4:0.1) as eluant afforded the product 76 (590 mg, 77%). $^1$H-NMR (CDCl$_3$): δ 0.95 (t, 6H), 1.15–1.40 (m, 32H), 2.30 (s, 30H), 2.55 (s, 60H), 2.90–3.25 (m, 36H), 3.60 (d, 4H), 5.40 (t, 2H), 6.95 (s, 20H). MS-FAB 2553 (M$^+$+Na).

Compound 77 was obtained following the procedure described for compound 75. From 650 mg (0.25 mmol) of decamide 76, 225 mg (81%) of decahydrochloride 77 was obtained; mp>270° C. (decomp). $^1$H-NMR (D$_2$O): δ 1.30 (t, 6H), 1.75 (b, 32H), 3.10 (b, 36H), 3.75 (b, 4H), 6.05 (b, 2H); $^{13}$C NMR (D$_2$O): δ 13.28, 25.57, 45.66, 49.00, 49.13, 49.64, 50.86, 131.15. MS-ESI 711 (M$^+$+1).

Compound 78 was obtained following the procedure described for compound 76. From 850 mg of 73, 360 mg (47%) of decamide 78 were obtained. $^1$H-NMR (CDCl$_3$): δ 0.95 (t, 6H), 1.15–1.45 (m, 32H), 2.30 (s, 30H), 2.55 (s, 60H), 2.90–3.20 (b, 36H), 3.65 (d, 4H), 5.40 (t, 2H), 6.90 (s, 20H). MS-FAB (m/z) 2553 (M$^+$+Na).

Compound 79 was obtained following the procedure described for compound 75. From 330 mg (0.13 mmol) of decamide 78, 127 mg (90%) of decahydrochloride 79 was obtained; mp>270° C. (decomp). $^1$H-NMR (D$_2$O): δ 1.30 (t, 6H), 1.80 (b, s, 32H), 3.10 (b, 36H), 3.85 (d, 4H), 6.0 (t, 2H). $^{13}$C NMR (D$_2$O): δ 13.31, 25.59, 45.71, 46.83, 49.05, 49.39, 49.69, 129.21. MS-ESI (m/z) 512 (M$^+$+2).

Compound 96: A suspension of NaH (60% in mineral oil, 336 mg, 14 mmol) in DMF (50 ml) was slowly added to a stirred solution of benzyl-4-bromobuty ether (3.645 g, 15 mmol) and mesitylenesulfonamide 18 (7.33g, 10 mmol) in DMF (180 ml) at 0° C. The reaction mixture was stirred for 10 h at 50° C., quenched with 15 ml of H$_2$O at 0° C., acidified to pH=7 with 5% HCl, extracted with Et$_2$O, washed with brine, dried (Na$_2$SO$_4$), and purified on a column (SiO$_2$, EtOAc/Hexane=3:7); yield 6.9 g, (77%). $^1$H-NMR (CDCl$_3$): δ 0.98 (t, J=7.1 Hz, 3H, CH$_3$), 1.25–1.30 (m, 12H, CH$_2$), 2.27 (s, 3H, CH$_3$), 2.29 (s, 6H, CH$_3$), 2.55 (s, 18H, CH$_3$), 3.0–3.2 (m, 12H, CH$_2$), 3.31 (t, J=6.0 Hz, CH$_2$), 4.41 (s, 2H, CH$_2$), 6.91 (s, 2H, Ph), 6.92 (s, 4H, Ph), 7.2–7.4 (m, 5H, Ph).

Compound 97: A solution of HBr 30% in AcOH (45 ml) was added to a stirred solution of 96 (2 g, 2.24 mmol) and phenole (6.324 g, 67.2 mmol) in CH$_2$Cl$_2$ (23 ml) at 0° C. The cooling bath was removed and the reaction mixture was stirred for 24 h at 20° C. The reaction mixture was quenched with H$_2$O (45 ml), washed with CH$_2$Cl$_2$, and concentrated to dryness in vacuo. The residue was cooled to 0° C., basified with 2N NaOH (5 ml), followed by 50% KOH (5 ml). The product was extracted with CHCl$_3$ (7×10 ml); yield 475 mg (81%). $^1$H-NMR (D$_2$O): δ 1.10 (t, J=7 Hz, 3H, CH$_3$), 1.45–1.70 (m, 12H, CH$_2$), 2.55–2.70 (m, 12H, CH$_2$), 3.57 (t, J=5.0 Hz, CH$_2$).

Compound 98: A solution of Na$_2$CO$_3$ (10%, 26 ml) was added to triamine 97 (830 mg, 3.20 mmol) in dioxane (21 ml). Di-tert-butyl dicarbonate (3.25 g, 24 mmol) solution in dioxane (21 ml) was added into the reaction mixture at 0° and stirred for 10 h at 20° C. The reaction mixture was diluted with CHCl$_3$ (200 ml), washed with H$_2$O, brine, dried (Na$_2$SO$_4$), concentrated and purified on a column (SiO$_2$, EtOAc/hexane=4:6); yield 1.7 g, (96%). $^1$H-NMR (CDCl$_3$): δ 1.09 (t, J=7.1 Hz, 3H, CH$_3$), 1.45–1.65 (m, 39H, CH$_2$, CH$_3$), 3.1–3.3 (m, 12H, CH$_2$), 3.67 (t, J=6 Hz, CH$_2$).

Compound 99: Diethyl azodicarboxylate (196 mg, 1.13 mmol) in THF (0.6 ml) was added to a cold mixture of 98 (630 mg, 1.127 mmol), triphenylphosphine (296 mg, 1.13 mmol) and phthalimide (166 mg, 1.13 mmol) in THF (1.2 ml), stirred for 10 h, concentrated in vacuo, and purified on a column (SiO$_2$, EtOAc/hexane=3:7); yield 835 mg (97%). $^1$H-NMR (CDCl$_3$): δ 1.09 (t, J=7, 3H, CH$_3$), 1.35–1.80 (m, 39H, CH$_2$, CH$_3$), 3.1–3.35 (m, 12H, CH$_2$), 3.70 (t, J=6.7 Hz, 2H, CH$_2$), 7.68–7.80 (m, 2H, Phth), 7.80–7.87 (m, 2H, Phth).

Compound 100: A mixture of 99 (275 mg, 0.4 mmol), hydrazine monohydrate (98%, 43.5 μl, 0.85 mmol) in EtOH were heated at 80° C. for 45 min. The precipitate was filtered and washed with cold EtOH, filtrate was combined with washings, concentrated and dried in vacuo; yield 220 mg (99%). $^1$H-NMR (CDCl$_3$): δ 1.09 (t, J=7.0 Hz, 3H, CH$_3$), 1.25–1.57 (m 39H, CH$_2$, CH$_3$), 2.71 (t, J=6.7 Hz, 2H, CH$_2$), 3.1–3.3 (m, 12H, CH$_2$), Compound 101 Mesoporphyrin IX dihydrochloride (70 mg, 0.11 mmol) was dissolved in DMF (1 ml), combined with HBTU (83 mg, 0.22 mmol) and diisopropylethyl amine (174 μl, 1 mmol). The mixture was stirred for 5 min, combined with 100 (167 mg, 0.3 mmol), stirred for 10 h, quenched with H$_2$O, concentrated in vacuo, dissolved in CHCl$_3$, washed with H$_2$O (5 times), 2% KHSO$_4$, NaHCO$_3$ solution, dried (Na$_2$SO$_4$), and purified by a column chromatography (SiO$_2$, MeOH/CHCl$_3$=1:20); yield 177 mg (98%). $^1$H-NMR (CDCl$_3$): δ 1.06 (t, J=6.9, 6H, CH$_3$), 1.1–1.5 (m, 78H, CH$_2$, CH$_3$), 1.86 (t, J=6.6 Hz, 6H, CH$_3$), 2.9–3.25 (m, 28H, CH$_2$), 3.62 (s, 3H, CH$_3$), 3.63 (s, 3H, CH$_3$), 3.64 (s, 3H, CH$_3$), 3.65 (s, 3H, CH$_3$), 4.07 (q, J=7.5 Hz, 4H, CH$_2$), 4.43 (t, J=7Hz, 4H, CH$_2$), 10.07 (s, 3H, CH), 10.27 (s, 1H).

Compound 102: Trifluoroacetate (1 ml) was added to a solution of 101 (165 mg, 0.1 mmol) in CH$_2$Cl$_2$ (2 ml) at 0° C., stirred for 1.5 h, and concentrated in vacuo at 20° C. The product was dried in vacuo for 3 h, dissolved in 10 ml of 10% HCl, washed with CHCl$_3$, and the aqueous part was concentrated and dried in vacuo at 20° C.; yield 100 mg (75%), purple solid, mp>200° C. Purity 96% (HPLC). $^1$H-NMR (D$_2$O): δ 0.7–1.0 (m), 1.0–1.2 (m), 1.29 (t, J=7.3 Hz), 1.4–1.7 (m), 2.6–2.35 (m), 2.72 (t, J=7.2 Hz), 2.9–3.2 (m), 3.6–3.75 (m), 3.76 (s), 3.79 (s), 4.29 (q, J=7.6 Hz), 4.4–4.7 (m). MS-MALDI (m/z): 1193 (M$^+$+4 HCl), 1156 (M$^+$+3 HCl), 1119 (M$^+$+2 HCl), 1083 (M$^+$+HCl), 1048 (M$^+$+1).

Compound 103 was prepared from 71 in 85% yield as described above for 96. $^1$H-NMR (CDCl$_3$): δ 0.97 (t, J=7 Hz, 3H, CH$_3$), 1.3–1.55 (m, 16H, CH$_2$), 2.27 (s, 3H, CH$_3$), 2.29 (s, 9H, CH$_3$), 2.55 (s, 24H, CH$_3$), 3.0–3.25 (m, 16H, CH$_2$), 3.31 (t, J=5.8 Hz, 2H, CH$_2$), 4.41 (s, 2H, CH$_2$), 6.90 (s, 2H, Ph), 6.92 (s, 6H, Ph).

Compound 104 was prepared from 103 in 80% yield as described for 97. $^1$H-NMR (CDCl$_3$): δ 1.10 (t, J=7.2 Hz, 3H, CH$_3$), 1.5–1.8 (m, 16H, CH$_2$), 2.5–2.75 (m, 16H, CH$_2$), 3.57 (t, J=5.5 Hz, 2H, CH$_2$). $^{13}$C-NMR (CDCl$_3$): δ 15.23, 27.55, 27.92, 28.58, 32.35, 44.02, 49.35, 49.66, 49.80, 62.32.

Compound 105 was prepared from 104 in 98% yield as described for 98. $^1$H-NMR (CDCl$_3$): δ 1.09 (t, J=7.1 Hz, 3H, CH$_3$), 1.4–1.7 (m, 52 H, CH$_2$, CH$_3$), 3.05–3.3 (m, 16H, CH$_2$), 3.67 (t, J=5.8 Hz, 2H, CH$_2$).

Compound 106: Oxalyl chloride (2N solution in CH$_2$Cl$_2$, 0.821 μl, 1.642 mmol) was diluted with anhydrous CH$_2$Cl$_2$ (6 ml) at −60° C. DMSO (223 μl, 2.59 mmol) in CH$_2$Cl$_2$ (3 ml) was added to the mixture, the latter stirred for 5 min at −60° C., and 105 (1.115 g, 1.525 mmol) in CH$_2$Cl$_2$ (9 ml) was introduced into the reaction. After 30 min of stirring at −60° C. triethylamine (1.06 ml, 14.46 mmol) was added into the reaction mixture and the temperature was allowed to rise to 20° C. (ca. 1.5 h). The reaction mixture was diluted with CH$_2$Cl$_2$, washed with H$_2$O, NaHCO$_3$, and brine. The product was concentrated to dryness in vacuo and purified by column chromatography (SiO$_2$, EtOAc/Hexane=3:7); yield 989 mg (89%). $^1$H-NMR (CDCl$_3$): δ 1.09 (t, J=7.0 Hz, 3H, CH$_3$), 1.4–1.6 (m, 48H, CH$_2$, CH$_3$), 1.84 (m, 2H, CH$_2$), 2.45 (t, J=6.8, 2H, CH$_2$), 3.05–3.3 (m, 16H, CH$_2$), 9.78 (s, 1H, CHO).

Compound 107: Platinum oxide (100 mg) was reduced in methanol (30 ml) in the hydrogen atmosphere at 30 psi. for 15 min. Product 106 (989 mg, 1.36 mmol) was dissolved in a 2M solution of ethylamine in EtOH (7 ml), added to the hydrogenation flask, and hydrogenated for 10 h at 50 psi. The catalyst was removed by filtration through Celite and the filtrate was concentrated to dryness in vacuo; yield 1.0 g (99%). $^1$H-NMR (CDCl$_3$): δ 1.09 (t, J=7.6 Hz, 3H, CH$_3$), 1.12 (t, J=7.2 Hz, 3H, CH$_3$), 1.3–1.65 (m, 50H, CH$_2$, CH$_3$), 1.66 (m, 2H, CH$_2$), 2.71 (m, 2H, CH$_2$), 3.1–3.3 (m, 18H, CH$_2$). MS-MALDI (m/z):758.8 (M$^+$, 100%), 744 (30%).

Compound 108 was prepared from 107 in 98% yield as described above for 101. $^1$H-NMR (CDCl$_3$): δ 0.8–1.8 (m), 1.87 (t, J=7.3 Hz, 6H, CH$_3$), 2.5–3.5 (m), 3.65 (s, 6H, CH$_3$), 3.67 (s, 6H, CH$_3$), 4.10 (q, J=7.5, 4H, CH$_2$), 4.46 (t, J=6.8, 4H, CH$_2$), 10.11 (bs, 4H, porph. core).

Compound 109 was prepared from 108 in 75% yield as described above for 102; purple solid, mp>200° C. Purity 96% (HPLC). $^1$H-NMR (D$_2$O): δ 0.25–0.5 (m), 0.6–0.8 (m), 1.1–1.5 (m), 1.5–2.0 (m), 1.32 (t), 2.6–3.4 (m), 3.6–3.9 (m), 3.78 (s), 3.82 (s), 4.2–4.6 (m). MS-MALDI (m/z): 1246.22 (M$^+$+1), 623.82 (M$^{2+}$).

Compound 111: Nitrile 70 (274 mg, 0.343 mmol) was hydrogenated in a 5% solution of CHCl$_3$ in EtOH (20 ml) in the presence of PtO$_2$ (60 mg) at 50 psi for 15 h. The reaction mixture was filtered through Celite and concentrated to dryness in vacuo to yield 110 (288 mg, 100%). Amine 110 was utilized without further purification. Mesoporphyrin IX dihydrochloride (100 mg, 0.156 mmol) was dissolved in DMF (4 ml), HBTU (118 mg, 0.312 mmol) and DIEA (174 μl, 2 mmol) were added to the solution, the latter stirred for 5 min, combined with 110, and kept for 15 h. The reaction mixture was quenched with 0.5 ml of $H_2O$, concentrated in vacuo, dissolved in $CHCl_3$, washed with 3% HCl solution, brine, dried ($Na_2SO_4$), and purified on a column ($SiO_2$, $CHCl_3$/MeOH=15:4); yield 327 mg (98%). $^1$H NMR ($CDCl_3$): δ 0.5–0.8 (m), 0.8–1.1 (m), 0.87 (t, J=7 Hz), 1.1–1.3 (m), 1.5–1.8 (m), 1.88(q, J=5 Hz), 2.0–2.3 (m), 2.10 (s, $CH_3$-Mes), 2.13 (s, $CH_3$-Mes), 2.16 (s, $CH_3$-Mes), 2.18 (s, $CH_3$-Mes), 2.43 (s, $CH_3$-Mes), 2.49 (s, $CH_3$-Mes), 2.7–2.9 (m), 2.9–3.2 (m), 3.64 (s, porph), 3.66 (s, porph), 4.1 (q, porph.), 4.4 (t, porph.), 6.69 (s, NH), 6.80 (s, NH), 6.85 (s, NH), 6.93 (s, NH), 10.07 (s, porph), 10.09 (s, porph), 10.22 (s, porph.). MALDI (m/z): 2141.03 ($M^+$+1), 1071.22 ($M^{2+}$).

Compound 112: Porphyrin 111 (350 mg, 0.163 mmol) was stirred in a suspension of $LiAlH_4$ (12.4 mg, 0.326 mmol) in THF (1 ml) for 24 h at 50° C. The reaction mixture was cooled to 0° C., quenched with $H_2O$ (0.1 ml), basified with 2N NaOH (0.5 ml), then diluted with $CH_2Cl_2$, filtered through Celite, washed with $H_2O$, dried ($Na_2SO_4$), and concentrated in vacuo. The product was stirred in a mixture of phenol (920 mg, 9.4 mmol) in $CH_2Cl_2$ (8 ml), and 30% solution of HBr in AcOH (7 ml) for 15 h. The reaction mixture was cooled to 0° C., diluted with 10 ml of $H_2O$ and the aqueous layer was filtered and washed with $CH_2Cl_2$. Following drying in vacuo of the aqueous solution, the residue was basified with 2N NaOH (1 ml) and 16 N NaOH (1 ml) and the reaction product was extracted with $CHCl_3$. The product 112 was purified by HPLC and converted to its hydrochloride by dissolution in 10% HCl and evaporation of the acid in vacuo; purple solid, mp 200° C. Purity 96% (HPLC). $^1$H NMR ($D_2O$): δ 1.32 (t, J=7.3 Hz, 6H, $CH_3$), 1.25–1.35 (m, 30H, $CH_2$), 2.5–2.65 (m, 4H, $CH_2$), 3.0–3.3 (m, 32H, $CH_2$), 3.4–3.5 (m, 4H, $CH_2$), 3.55–3.65 (m, 6H, $CH_3$), 3.73 (s, 3H, $CH_3$), 3.75 (s, 3H, $CH_3$), 4.0–4.25 (m, 4H, $CH_2$), 4.3–4.5 (m, 4H). MALDI (m/z): 1073.8 ($M^+$+$NH_4Cl$), 1020.0 ($M^+$+1), 510.62 ($M^{2+}$), 340.82 ($M^{3+}$).

Compound 113: Diisobutylaluminum hydrate (1.16 ml of 1.5 M solution in toluene, 1.74 mmol) was added into a solution of mesoporphyrin IX dimethyl ester (500 mg, 84 mmol) in $CH_2Cl_2$ (10 ml) at −78° C., stirred at this temperature for 1 h, quenched with saturated solution of $NH_4Cl$ (1 ml), followed by 3.7% solution of HCl (2 ml). The temperature of the reaction mixture was allowed to rise to 20° C., the product was extracted with $CH_2Cl_2$, dried ($Na_2SO_4$), and purified on a column ($SiO_2$, EtOAc/Hexane=3:7), yield 330 mg (73%). $^1$H-NMR ($CDCl_3$): δ 1.86 (t, J=7.6 Hz, 6H, $CH_3$), 3.39 (t, J=7.4 Hz, 6H, $CH_3$), 3.60 (s, 6H, $CH_3$), 3.62 (s, 6H, $CH_3$), 4.0–4.2 (m, 4H, $CH_2$), 4.25–4.45 (m, 4H, $CH_2$), 9.97 (s, 1H), 10.04 (s, 1H), 10.05 (s, 1H), 10.058 (s, 1H), 10.062 (s, 1H), 10.07 (s, 1H).

TABLE 1

Polyamine analogs

| Compound | Structure |
|---|---|
| SL-11090 | 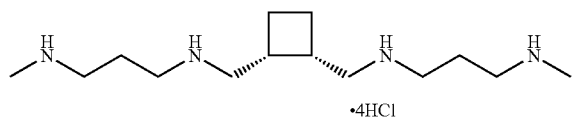 ·4HCl |
| SL-11091 | 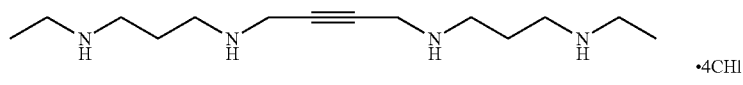 ·4CHl |
| SL-11092 | 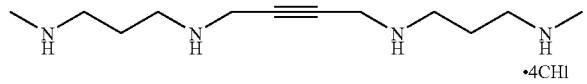 ·4CHl |
| SL-11101 | 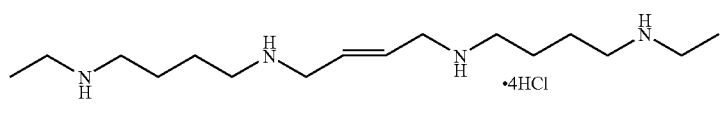 ·4HCl |
| SL-11103 |  ·4CHl |
| SL-11114 | 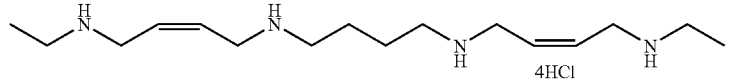 4HCl |
| SL-11118 | 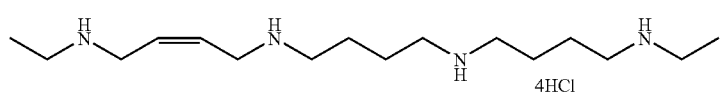 4HCl |

TABLE 1-continued

Polyamine analogs

| Compound | Structure |
| --- | --- |
| SL-11121 | Et-NH-(CH₂)₃-NH-(CH₂)₃-NH-(CH₂)₃-NH-CH₂-CH=CH-CH₂-NH-Et · 5HCl |
| SL-11122 | Et-NH-(CH₂)₃-NH-(CH₂)₃-NH-CH₂-CH=CH-CH₂-NH-(CH₂)₄-NH-Et · 5HCl |
| SL-11123 | Et-NH-(CH₂)₄-NH-CH₂-CH=CH-CH₂-NH-CH₂-CH=CH-CH₂-NH-(CH₂)₄-NH-Et · 5HCl |
| SL-11124 | (2-ethylaminocyclopentyl)methyl-NH-(CH₂)₃-NH-methyl(2-ethylaminocyclopentyl) · 4HCl |
| SL-11126 | Et-NH-CH₂-CH=CH-CH₂-NH-CH₂-CH=CH-CH₂-NH-CH₂-CH=CH-CH₂-NH-CH₂-CH=CH-CH₂-NH-Et · 5HCl |
| SL-11127 | Et-NH-(CH₂)₃-NH-(CH₂)₄-NH-CH₂-CH=CH-CH₂-NH-CH₂-CH=CH-CH₂-NH-Et · 5HCl |
| SL-11128 | Et-NH-CH₂-CH=CH-CH₂-NH-(CH₂)₄-NH-(CH₂)₄-NH-CH₂-CH=CH-CH₂-NH-Et · 5HCl |
| SL-11129 | Et-NH-CH₂-CH=CH-CH₂-NH-CH₂-CH=CH-CH₂-NH-(CH₂)₄-NH-CH₂-CH=CH-CH₂-NH-Et · 5HCl |
| SL-11130 | Et-NH-CH₂-CH=CH-CH₂-NH-CH₂-CH=CH-CH₂-NH-CH₂-CH=CH-CH₂-NH-(CH₂)₄-NH-Et · 5HCl |
| SL-11132 | (2-ethylaminocyclopentyl)methyl-NH-(CH₂)₃-NH-(CH₂)₃-NH-Et · 4HCl |
| SL-11133 | Et-NH-(CH₂)₃-NH-CH₂-CH=CH-CH₂-NH-(CH₂)₃-NH-CH₂-CH=CH-CH₂-NH-Et · 5HCl |
| SL-11134 | (4-amidinophenyl)methyl-NH-(CH₂)₄-NH-methyl(4-amidinophenyl) · 4HCl |

TABLE 1-continued
Polyamine analogs
| Compound | Structure |
|---|---|
| SL-11136 | 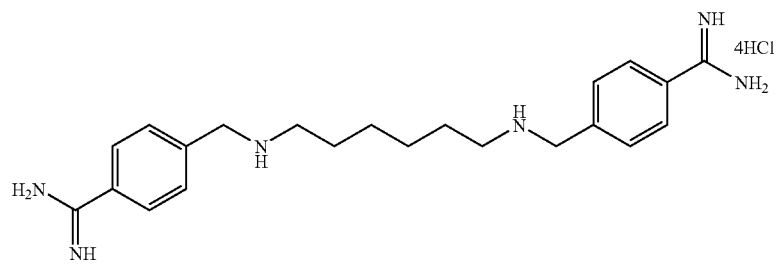 |
| SL-11137 | 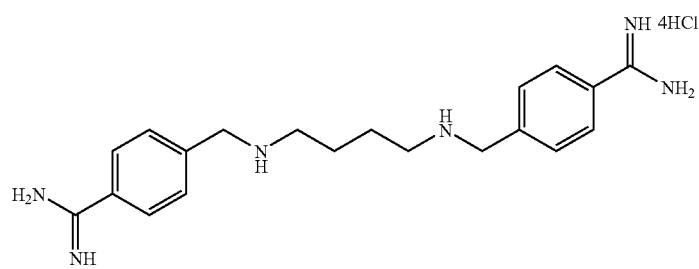 |
| SL-11141 | 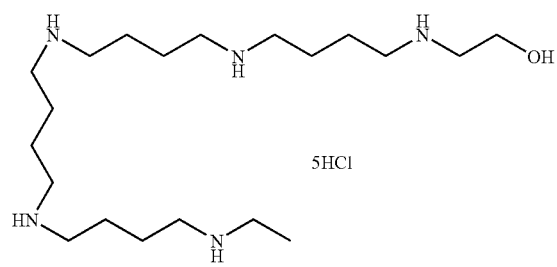 |
| SL-11144 | 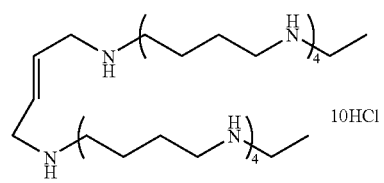 |
| SL-11150 | 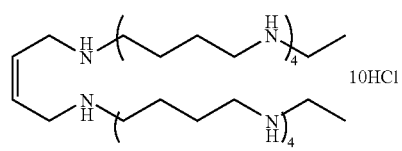 |
| SL-11201 | 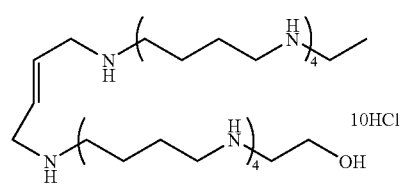 |
| SL-11202 | 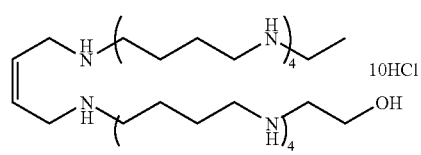 |

TABLE 2
Polyamine-porphyrin conjugates
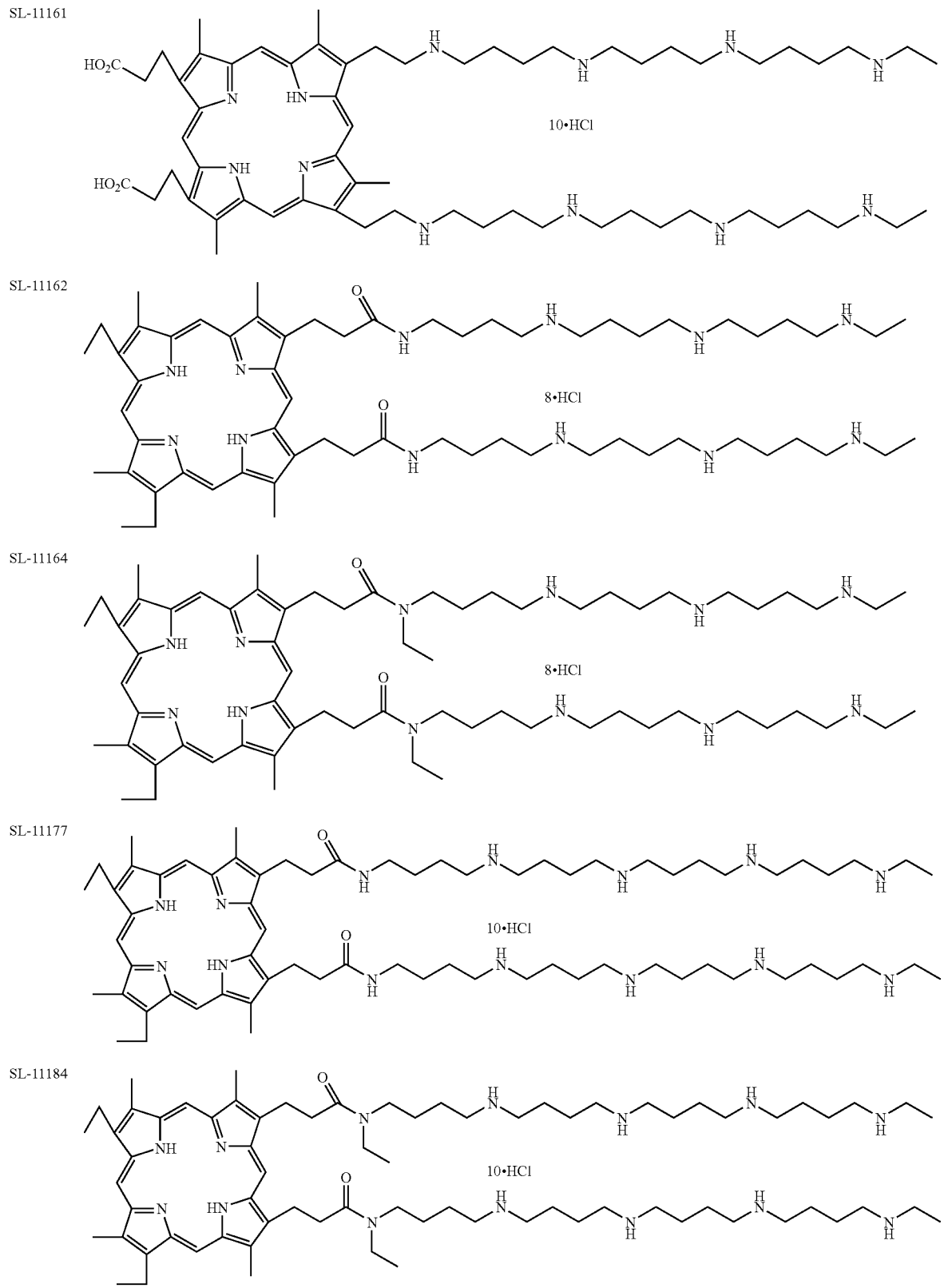

TABLE 2-continued

Polyamine-porphyrin conjugates

SL-11202

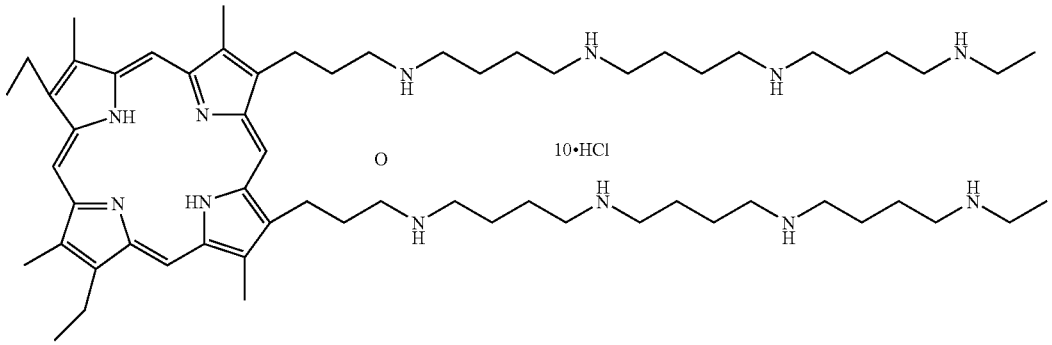

Example 2

In vitro Testing of the Efficacy of Novel Polyamine Analogs Against Tumor Cell Lines These experiments are designed to evaluate the newly synthesized compounds described above against cultured human carcinoma cell lines for their effects on cell growth, cell-cycle regulation and polyamine regulatory responses. Additional methods for testing compounds are described in U.S. Pat. No. 5,889,061.

As shown in Table 3 and FIGS. 1–32, several novel conformationally restricted polyamine analogs were tested for anti-proliferative properties against cancer cells. Table 3 illustrates the concentration in μM of the various novel polyamine analogs needed for 50% growth inhibition ($ID_{50}$) values for human cancer cell lines LNCaP, PC-3, DuPro (all three human prostate cancer cell lines), HT-29 (colon cancer cell line), A549 (lung cancer cell line), MCF7 (breast cancer cell line), and U251 MG-NCI (brain cancer cell line). FIGS. 1–32 show a representative plot of the effects of some of these novel analogs on the growth of human tumor cell lines, as determined by MTT (methyl thiazol tetrazolium) assay; known anti-proliferative polyamine analogs BE-333, BE-343, BE-444, and BE-4444 were used for comparative purposes.

Cell Lines and Media

Human breast cancer cell line MCF7 was grown in Richter's Improved Modified Eagle's Medium supplemented with 10% fetal bovine serum (FBS) and 2.2 g/L sodium bicarbonate. Human brain tumor cell line U251 MG-NCI was grown in Dulbecco's Modified Eagle's Medium supplemented with 10% FBS. Human lung cancer cell line A549 was grown in Ham's F-12K medium (Cellgro, Mediatech, Inc., VA), supplemented with 10% FBS and 2 mM L-glutamine. Human colon cancer cell line HT29 was cultured in McCoy's 5A medium (Gibco, BRL, Gaithersburg, Md.) supplemented with 10% FBS. Human prostate cancer cell lines PC-3, LNCAP and DuPro were grown in RPMI 1640 Medium (Cellgro, Mediatech, Inc., VA) supplemented with 10% FBS. Another human prostate cancer cell line DU145 was grown in Dulbecco's Modified Eagle's Medium (Gibco, BRL, Gaithersburg, Md.) supplemented with 5% FBS. The A549, MCF7, PC3, LNCAP and DuPro cell lines were cultured in 100 units/mL penicillin and 100 μg/mL streptomycin. HT29 and U251MG cell lines were grown in 50 μg/mL gentamycin (Gibco, BRL, Gaithersburg, Md.). DU145 cell line was maintained in 1% antibiticantimycotic solution (Sigma, St. Louis, Mo.). The cell cultures were maintained at 37° C. in 5% $CO_2$/95% humidified air. DuPro cells were obtained from M. Eileen Dolan, University of Chicago. All other cells are available from the American Type Culture Collection, Rockville, Md.

MTT Assay

A conventional MTT assay was used to evaluate percent cell survival. Exponentially growing monolayer cells were plated in 96-well plates at a density of 500 cells per well and allowed to grow for 24 hours. Serial dilutions of the drugs were added to the wells. Six days after drug treatment, 25 μl of MTT solution (5 mg/ml) was added to each well and incubated for 4 hours at 37° C. Then 100 μl of lysis buffer (20% sodium dodecyl sulfate, 50% DMF, and 0.8% acetic acid, pH 4.7) was added to each well and incubated for an additional 22 hours. A microplate reader ("EMAX"-brand, Molecular Devices, Sunnyvale, Calif.) set at 570 nm was used to determine the optical density of the cultures. Results are expressed as a ratio of the optical density in drug-treated wells to the optical density in wells treated with vehicle only.

TABLE 3

|  | PC-3 | DU-145 | DUPRO | HT-29 | A549 | MCF7 | U251MG |
|---|---|---|---|---|---|---|---|
| BE-4444 | 0.54 | 0.07 | 0.2 | 0.8 | 0.4 | >31.25 | NT |
| SL-11029 | 24.5 | 0.32 | NT | >31.25 | >31.25 | >31.25 | >31.25 |
| SL-11090 | >31.25 | >31.25 | NT | >31.25 | >31.25 | >31.25 | >31.25 |
| SL-11091 | >31.25 | 1.33 | NT | >31.25 | >31.25 | >31.25 | >31.25 |
| SL- | >31.25 | 1.7 | NT | >31.25 | >31.25 | >31.25 | >31.25 |

TABLE 3-continued

| | PC-3 | DU-145 | DUPRO | HT-29 | A549 | MCF7 | U251MG |
|---|---|---|---|---|---|---|---|
| SL-11092 | 14.3 | 0.01 | 0.06 | 0.40 | 0.26 | 0.66 | NT |
| SL-11093 | >31.25 | 12.6 | NT | 28.8 | >31.25 | >31.25 | >31.25 |
| SL-11094 | 1.4 | 0.018 | 0.08 | 0.40 | 0.51 | >31.25 | 0.10 |
| SL-11098 | 2.5 | 0.014 | 0.08 | 1.00 | 0.65 | 26.3 | 0.11 |
| SL-11099 | 4.7 | 0.021 | 0.29 | 2.00 | 2.20 | >31.25 | 0.22 |
| SL-11100 | 7.7 | 0.218 | 0.85 | 5.20 | 0.15 | >31.25 | 1.70 |
| SL-11101 | >31.25 | 0.027 | 0.15 | 0.73 | 12.40 | >31.25 | 0.15 |
| SL-11102 | >31.25 | 2.8 | NT | 29.4 | >31.25 | >31.25 | 9.50 |
| SL-11103 | >31.25 | 9.4 | NT | 25.8 | 0.43 | >31.25 | 14.71 |
| SL-11104 | >31.25 | 1.6 | >31.25 | 25.2 | >31.25 | >31.25 | 25.9 |
| SL-11105 | 2.2 | 0.13 | 0.98 | 2.00 | >31.25 | >31.25 | 2.00 |
| SL-11108 | 0.70 | 0.135 | 0.64 | 3.6 | >31.25 | NT | NT |
| SL-11114 | 1.65 | 0.05 | 0.25 | 0.98 | 0.21 | NT | NT |
| SL-11118 | >31.25 | 0.08 | 0.44 | 0.97 | NT | NT | NT |
| SL-11119 | 0.52 | 0.08 | 0.40 | 0.80 | >31.25 | 17.0 | NT |
| SL-11121 | >31.25 | 0.80 | 0.56 | 0.80 | >31.25 | >31.25 | NT |
| SL-11122 | >31.25 | 0.51 | >31.25 | 10.42 | >31.25 | >31.25 | NT |
| SL-11123 | >31.25 | >31.25 | >31.25 | >31.25 | >31.25 | >31.25 | NT |
| SL-11124 | 0.20 | 0.51 | 1.10 | 1.50 | >31.25 | 0.70 | NT |
| SL-11126 | >31.25 | 0.22 | 1.3 | 2.91 | NT | NT | NT |
| SL-11127 | 0.50 | 0.14 | 1.25 | 1.35 | NT | NT | NT |
| SL-11128 | 1.70 | 0.32 | NT | NT | NT | NT | NT |
| SL-11129 | >31.25 | 0.43 | NT | NT | NT | NT | NT |
| SL-11130 | | | | | | | |

NT indicates not tested.

Example 3

In vivo Testing of Anti-tumor Activity of Polyamine Analogs

Analogs found to have potent or mechanism-based antiproliferative activity in vitro towards cultured carcinoma cells are evaluated in in vivo model systems. The first goal is to determine the relative toxicity of the analogs in non-tumor-bearing animals, such as DBA/2 mice. Groups of three animals each are injected intraperitoneally with increasing concentrations of an analog, beginning at 10 mg/kg. Toxicity, as indicated by morbidity, is closely monitored over the first 24 hr. A well-characterized polyamine analog, such as BE-333, is used as an internal standard in these studies, since a data base has already been established regarding acute toxicity via a single dose treatment relative to chronic toxicity via a daily×5 d schedule. Thus, in the case of new analogs, single dose toxicity relative to BE-333 is used to project the range of doses to be used on a daily×5 d schedule.

After the highest tolerated dosage on a daily×5 d schedule is deduced, antitumor activity is determined. Tumors are subcutaneously implanted into nude athymic mice by trocar and allowed to reach 100–200 mm$^3$ before initiating treatment by intraperitoneal injection daily×5 d. Analogs are given in a range between 10 and 200 mg/kg. Analogs are evaluated at three treatment dosages with 10–15 animals per group (a minimum of three from each are used for pharmacodynamic studies, described below). Mice are monitored and weighed twice weekly to determine tumor size and toxicity. Tumor size is determined by multi-directional measurement from which volume in mm$^3$ is calculated. Tumors are followed until median tumor volume of each group reaches 1500 mm$^3$ (i.e., 20% of body weight), at which time the animals are sacrificed. Although the initial anti-tumor studies focused on a daily×5 d schedule, constant infusion is performed via Alzet pump delivery for 5 days since this schedule dramatically improves the anti-tumor activity of BE-333 against A549 human large cell lung carcinoma. Sharma et al. (1997) *Clin. Cancer Res.* 3:1239–1244. In addition to assessing anti-tumor activity, free analog levels in tumor and normal tissues are determined in test animals.

Example 4

In vitro Testing of Porphyrin-polyamine Conjugates

Using the protocols of Example 2, the porphyrin-polyamine conjugates were tested for activity in vitro in various cancer cell lines. The results are shown in Table 4 and FIGS. 45–49.

TABLE 4

Effect of Polyamine Porphyrin Complexes on the Growth of Human Prostate Cell Lines by MTT Assay.

| | $IC_{50}$ (μM) in different cell lines | | | |
|---|---|---|---|---|
| Compounds | PC3 | DUPRO | LNCAP | DU145 |
| SL-11162 | 2.8 | 1.9 | 4.8 | |
| SL-11177 | 0.9 | 0.7 | 4.8 | |
| SL-11184 | 1.4 | 1.5 | | 8.4 |
| SL-11202 | 1.15 | 1.3 | | 4.6 |

Example 5

In Vivo Testing of Porphyrin-polyamine Conjugates

Conjugates found to have potent or mechanism-based anti-proliferative activity in vitro towards cultured carcinoma cells are evaluated in in vivo model systems. The first goal is to determine the relative toxicity of the conjugates in non-tumor-bearing animals, such as DBA/2 mice. Groups of three animals each are injected intraperitoneally with increasing concentrations of an conjugate, beginning at 10 mg/kg. Toxicity, as indicated by morbidity, is closely monitored over the first 24 hr. A well-characterized compound, such as BE-333, is used as an internal standard in these studies, since a data base has already been established regarding acute toxicity via a single dose treatment relative to chronic toxicity via a daily×5 d schedule. Thus, in the case of new conjugates, single dose toxicity relative to BE-333 is used to project the range of doses to be used on a daily×5 d schedule.

After the highest tolerated dosage on a daily×5 d schedule is deduced, antitumor activity is determined. Tumors are subcutaneously implanted into nude athymic mice by trocar and allowed to reach 100–200 mm³ before initiating treatment by intraperitoneal injection daily×5 d. Conjugates are given in a range between 10 and 200 mg/kg. Conjugates are evaluated at three treatment dosages with 10–15 animals per group (a minimum of three from each are used for pharmacodynamic studies, described below). Mice are monitored and weighed twice weekly to determine tumor size and toxicity. Tumor size is determined by multi-directional measurement from which volume in mm³ is calculated. Tumors are followed until median tumor volume of each group reaches 1500 mm³ (i.e., 20% of body weight), at which time the animals are sacrificed. Although the initial anti-tumor studies focused on a daily×5 d schedule, constant infusion is performed via Alzet pump delivery for 5 days since this schedule dramatically improves the anti-tumor activity of BE-333 against A549 human large cell lung carcinoma. Sharma et al. (1997) *Clin. Cancer Res.* 3:1239–1244. In addition to assessing anti-tumor activity, free conjugate levels in tumor and normal tissues are determined in test animals.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention, which is delineated by the appended claims. All references disclosed herein, including U.S. Pat. No. 5,889,061, are hereby incorporated by reference in their entirety.

What is claimed is:

1. A composition comprising a porphyrin-polyamine conjugate or porphyrin-polyamine analog conjugate, wherein the conjugate comprises a polyamine compound or polyamine analog compound covalently linked to a porphyrin compound, and a pharmaceutically acceptable carrier, wherein the composition comprises a therapeutic amount of the porphyrin-polyamine conjugate or porphyrin-polyamine analog conjugate for treatment of cancer or uncontrolled cell proliferation, and with the proviso that the polyamine or polyamine analog is not spermine, and the proviso that the polyamine or polyamine analog does not have a tertiary amino group.

2. The composition of claim 1, wherein the covalent link is an amide bond or a amine bond.

3. A porphyrin-polyamine conjugate or porphyrin-polyamine analog conjugate of the formula

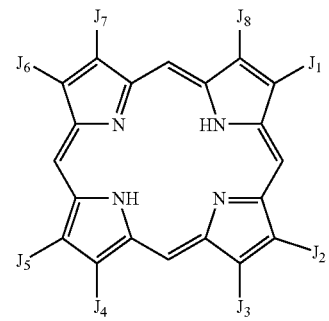

wherein at least one of $J_1$–$J_8$ is independently selected from the group consisting of -$K_1$-G-L-(N(P)-A)$_n$-$K_2$ where $K_1$ is independently selected from the group consisting of $C_1$–$C_8$ alkyl and where the valence to the left of $K_1$ attaches to the porphyrin ring;

G is —O—, —(C=O)—, —C(=O)—O—, —O—(C=O)—, —O—(C=O)—O—, —O—(C=O)—N—, —N—(C=O)—O—, or a nonentity;

L is $C_1$–$C_8$ alkyl, $C_3$–$C_8$ cycloalkyl, $C_3$–$C_8$ cycloaryl, $C_1$–$C_8$ alkoxy, $C_1$–$C_8$ alkyl-$C_3$–$C_8$ cycloalkyl, $C_1$–$C_8$ alkyl-$C_3$–$C_8$ cycloaryl, $C_1$–$C_8$ alkoxy-$C_3$–$C_8$ cycloaryl, $C_3$–$C_8$ cycloalkyl-$C_3$–$C_8$ cycloaryl, $C_3$–$C_8$ cycloalkyl-$C_1$–$C_8$ alkyl, $C_3$–$C_8$ cycloaryl-$C_1$–$C_8$ alkyl, $C_3$–$C_8$ cycloaryl-$C_1$–$C_8$ alkoxy, $C_3$–$C_8$ cycloaryl-$C_3$–$C_8$ cycloalkyl, or a nonentity;

each A is independently selected from the group consisting of $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, and $C_3$–$C_8$ cycloalkynyl;

P is independently selected from the group consisting of H and $C_1$–$C_8$ alkyl;

n is an integer from 2 to 8;

and $K_2$ is independently selected from the group consisting of H, $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, $C_3C_8$ cycloalkynyl, $C_1$–$C_8$ alkanol, $C_3$–$C_8$ cycloalkanol, and $C_3$–$C_8$ hydroxyaryl;

where the remainder of the groups $J_1$–$J_8$ are each independently selected from the group consisting of H, $K_3$, or $K_4$-COOH, where $K_3$ is independently selected from the group consisting of $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, $C_3$–$C_8$ cycloalkynyl, $C_1$–$C_8$ alkanol, $C_3$–$C_8$ cycloalkanol, and $C_3$–$C_8$ hydroxyaryl; and $K_4$ is independently selected from the group consisting of $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, and $C_3$–$C_8$ cycloalkynyl;

or any salt or stereoisomer thereof.

4. The composition of claim 3, wherein $K_1$ and each A are independently selected from the group consisting of $C_1$–$C_8$ alkyl, $K_2$ is independently selected from the group consisting of H and $C_1$–$C_8$ alkyl, and the remainder of the groups $J_1$–$J_8$ are each independently selected from the group consisting of H, $K_3$, or $K_4$-COOH, where $K_3$ and $K_4$ are independently selected from the group consisting of $C_1$–$C_8$ alkyl.

5. The composition of claim 4, wherein $K_1$ is —$CH_2$—$CH_2$— or —$CH_2$—$CH_2$—$CH_2$—.

6. The composition of claim 4, wherein n is 4.

7. The composition of claim 4, wherein $J_3$, $J_4$, $J_7$ and $J_8$ are independently selected from the group consisting of $C_1$–$C_3$ alkyl;

$J_5$ and $J_6$ are independently selected from the group consisting of $C_1$–$C_3$ alkyl and $C_1$–$C_3$ alkyl-COOH;

and $J_1$ and $J_2$ are independently selected from the group consisting of $C_1$–$C_3$ alkyl-G-N($P_1$)-A-(NH-A)$_{n1}$-$K_5$;

wherein G is —(C=O)— or a nonentity;

$P_1$ is independently selected from H or $C_1$–$C_3$ alkyl;

each A is independently selected from the group consisting of $C_1$–$C_8$ alkyl;

$n_1$ is 3 or 4;

and $K_5$ is independently selected from the group consisting of H and $C_1$–$C_8$ alkyl.

8. A method of treating aberrant cell growth in an individual comprising the step of administering to the individual a therapeutic amount of the composition of claim 1.

9. A method of inhibiting proliferation of diseased cells in an individual comprising the step of administering to the individual a therapeutic amount of the composition of claim 1.

10. The method of claim 8, wherein the aberrant cell growth is cancer.

11. The composition of claim 3 wherein the porphyrin-polyamine conjugate or porphyrin-polyamine analog conjugate is of the formula:

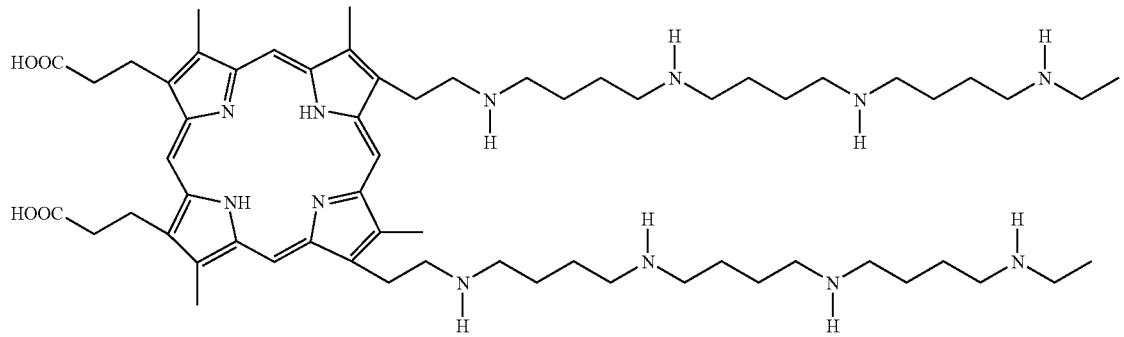

or any salt or stereoisomer thereof.

12. The composition of claim 3 wherein the porphyrin-polyamine conjugate or porphyrin-polyamine analog conjugate is of the formula:

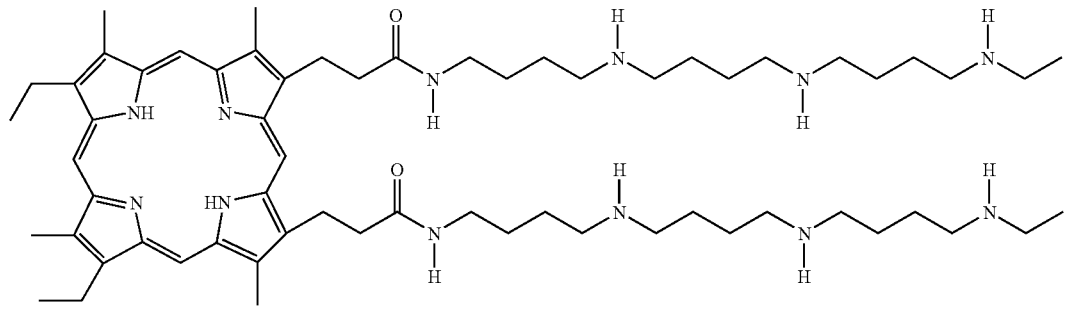

or any salt or stereoisomer thereof.

13. The composition of claim 3 wherein the porphyrin-polyamine conjugate or porphyrin-polyamine analog conjugate is of the formula:

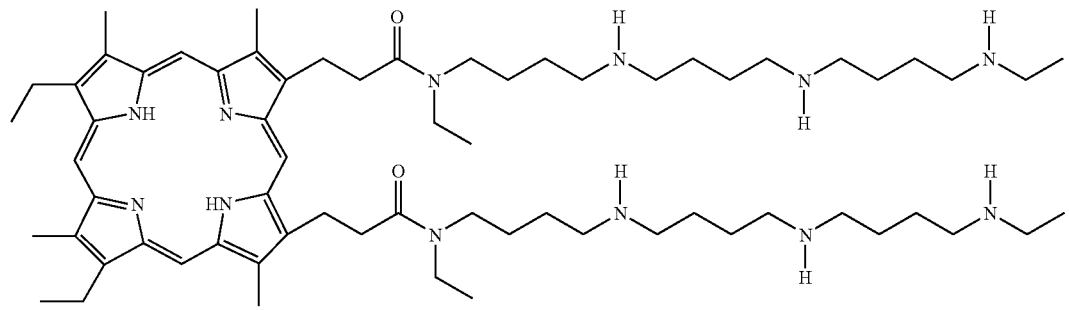

or any salt or stereoisomer thereof.

14. The composition of claim 3 wherein the porphyrin-polyamine conjugate or porphyrin-polyamine analog conjugate is of the formula:

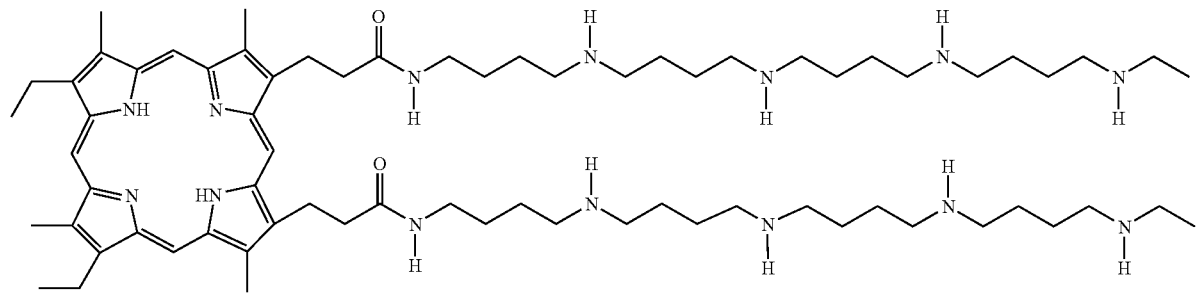

or any salt or stereoisomer thereof.

15. The composition of claim 3 wherein the porphyrin-polyamine conjugate or porphyrin-polyamine analog conjugate is of the formula:

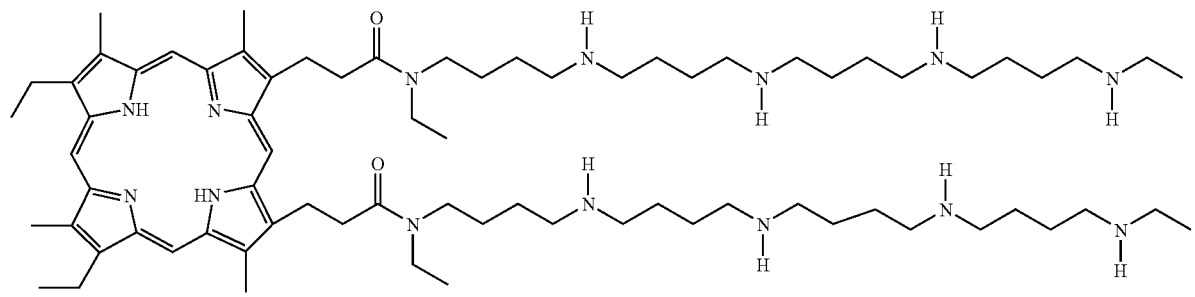

or any salt or stereoisomer thereof.

16. The composition of claim 3 wherein the porphyrin-polyamine conjugate or porphyrin-polyamine analog conjugate is of the formula:

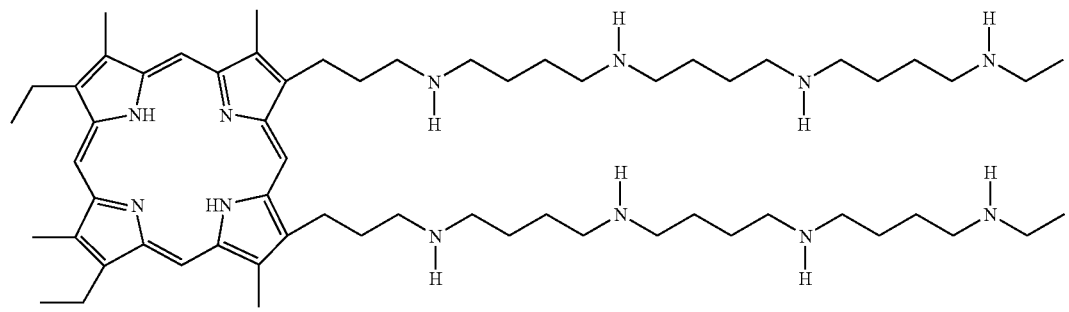

or any salt or stereoisomer thereof.

17. A method of treating aberrant cell growth in an individual comprising the step of administering to the individual a therapeutic amount of the composition of claim 3.

18. A method of inhibiting proliferation of diseased cells in an individual comprising the step of administering to the individual a therapeutic amount of the composition of claim 3.

19. A composition comprising a porphyrin-polyamine analog conjugate, wherein the conjugate comprises a polyamine analog compound covalently linked to a porphyrin compound, and a pharmaceutically acceptable carrier, wherein the composition comprises a therapeutic amount of the porphyrin-polyamine analog conjugate for treatment of cancer or uncontrolled cell proliferation, and with the proviso that the polyamine analog is conformationally restricted.

20. The composition of claim 19, wherein the covalent link is an amide bond or a amine bond.

* * * * *